US009868949B2

(12) United States Patent
Bettencourt et al.

(10) Patent No.: US 9,868,949 B2
(45) Date of Patent: Jan. 16, 2018

(54) ORGANIC COMPOSITIONS TO TREAT EPAS1-RELATED DISEASES

(71) Applicant: Arrowhead Research Corporation, Pasadena, CA (US)

(72) Inventors: Brian Bettencourt, Cambridge, MA (US); Shanthi Ganesh, East Hanover, NJ (US); Elizabeth George, Cambridge, MA (US); Dieter Heusken, Basel (CH); Stuart Milstein, Cambridge, MA (US); Jonathan Solomon, Cambridge, MA (US); Emily Thomas, Cambridge, MA (US); Ivanka Toudjarska, Cambridge, MA (US); Jennifer Tullai, Cambridge, MA (US); Jan Weiler, Cambridge, MA (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

(21) Appl. No.: 14/770,765

(22) PCT Filed: Feb. 27, 2014

(86) PCT No.: PCT/US2014/018873
§ 371 (c)(1),
(2) Date: Aug. 26, 2015

(87) PCT Pub. No.: WO2014/134255
PCT Pub. Date: Sep. 4, 2014

(65) Prior Publication Data

US 2016/0010089 A1 Jan. 14, 2016

Related U.S. Application Data

(60) Provisional application No. 61/770,713, filed on Feb. 28, 2013.

(51) Int. Cl.

| | |
|---|---|
| ***A61K 31/712*** | (2006.01) |
| ***A61K 31/7125*** | (2006.01) |
| ***C12N 15/113*** | (2010.01) |
| ***A61K 45/06*** | (2006.01) |
| ***A61K 31/7105*** | (2006.01) |
| ***A61K 31/7115*** | (2006.01) |
| ***A61K 31/713*** | (2006.01) |

(52) U.S. Cl.
CPC .......... *C12N 15/113* (2013.01); *A61K 31/712* (2013.01); *A61K 31/713* (2013.01); *A61K 31/7105* (2013.01); *A61K 31/7115* (2013.01); *A61K 31/7125* (2013.01); *A61K 45/06* (2013.01); *C12N 2310/14* (2013.01); *C12N 2310/315* (2013.01); *C12N 2310/321* (2013.01); *C12N 2310/342* (2013.01); *C12N 2310/351* (2013.01); *C12N 2320/30* (2013.01)

(58) Field of Classification Search
USPC ........... 435/6.1, 6.11, 6.12, 91.1, 91.31, 455, 435/458; 514/44; 536/23.1, 24.5
See application file for complete search history.

(56) References Cited

U.S. PATENT DOCUMENTS

| | | | | |
|---|---|---|---|---|
| 5,030,453 | A | 7/1991 | Lenk et al. | |
| 5,962,016 | A | 10/1999 | Willis | |
| 6,680,068 | B2 | 1/2004 | Campbell et al. | |
| 8,084,600 | B2 | 12/2011 | Natt et al. | |
| 8,097,716 | B2 | 1/2012 | Weiler et al. | |
| 8,114,983 | B2 * | 2/2012 | Davis .................. | C12N 15/113 536/24.5 |
| 8,344,128 | B2 | 1/2013 | Natt et al. | |
| 2003/0012812 | A1 | 1/2003 | Tormo et al. | |
| 2003/0036787 | A1 | 2/2003 | Vladimir et al. | |
| 2004/0038921 | A1 | 2/2004 | Kreutzer et al. | |
| 2004/0204377 | A1 | 10/2004 | Rana | |
| 2004/0208921 | A1 | 10/2004 | Ho et al. | |
| 2006/0240093 | A1 | 10/2006 | MacLachlan et al. | |
| 2007/0039072 | A1 | 2/2007 | Khvorova et al. | |
| 2007/0135372 | A1 | 6/2007 | MacLachlan et al. | |
| 2008/0113351 | A1 | 5/2008 | Naito et al. | |

(Continued)

FOREIGN PATENT DOCUMENTS

| | | |
|---|---|---|
| EP | 2213738 A2 | 4/2010 |
| WO | 2000044914 A1 | 8/2000 |

(Continued)

OTHER PUBLICATIONS

Office Action for corresponding Chinese Application No. 201480011225.5 (dated Feb. 15, 2017).
Bangoura et al. 2004 World J. Gastroenterol. 10: 525-530.
Bernstein, et al. 2001 Nature 409:363-366.
Burgin et al.1996 Biochem. 35: 14090-14097.
Caplen et al. 2001 Proc. Natl. Acad. Sci. (USA), 98: 9742-9747.
Chu and Rana 2008 RNA 14: 1714-1719.
Cleven et al. 2007 Analyt. Cell. Path. 29: 229-240.
Covello et al. 2006 Genes Dev. 20: 557-570.
Donze, O. and Picard, D, 2002 Nucleic Acids Research, Vo. 30, No. 10 e46.
Dowler et al. 2006 Nucl. Acids Res. 34: 1669-1675.
Duxbury et al., 2004 Surgery, 261-269.
Elbashir et al. 2001 Nature 411: 494-498.

(Continued)

*Primary Examiner* — Jane Zara
(74) *Attorney, Agent, or Firm* — Robert Michael Teigen

(57) ABSTRACT

The present disclosure relates to methods of treating EPAS1-related diseases such as cancer, metastases, astrocytoma, bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, non-small cell lung cancer, melanoma, multiple myeloma, ovarian cancer, rectal cancer, renal cancer, clear cell renal cell carcinoma (and metastases of this and other cancers), gingivitis, psoriasis, Kaposi's sarcoma-associated herpesvirus, preemclampsia, inflammation, chronic inflammation, neovascular diseases, and rheumatoid arthritis, using a therapeutically effective amount of a RNAi agent to EPAS1.

20 Claims, 1 Drawing Sheet

(56) References Cited

U.S. PATENT DOCUMENTS

| | | | |
|---|---|---|---|
| 2009/0209626 | A1 | 8/2009 | Khvorova et al. |
| 2014/0303232 | A1 | 10/2014 | Baryza et al. |

FOREIGN PATENT DOCUMENTS

| | | | |
|---|---|---|---|
| WO | 2001068836 | A2 | 9/2001 |
| WO | 2002100435 | A1 | 12/2002 |
| WO | 2003015757 | A1 | 2/2003 |
| WO | 2004002453 | A1 | 1/2004 |
| WO | 2004029213 | A2 | 4/2004 |
| WO | 2005021749 | A1 | 3/2005 |
| WO | 2007107162 | A2 | 9/2007 |
| WO | 2007128477 | A2 | 11/2007 |
| WO | 2008147824 | A2 | 12/2008 |
| WO | 2009082817 | A1 | 7/2009 |
| WO | 2009114836 | A1 | 9/2009 |
| WO | 2009123764 | A2 | 10/2009 |
| WO | 2011076807 | A2 | 6/2011 |

OTHER PUBLICATIONS

Elbashir et al. 2001 EMBO J. 20: 6877-6888.
Elbashir, et al. 2001 Genes Dev. 15:188-200.
Ema et al. 1997 Proc. Natl. Acad. Sci. USA 94: 4273-4278.
Farhood et al. 1995 Biochimica et Biophysica Acta 1235: 289-295.
Flamme et al. 1997 Mech. Dev.63: 51-60.
Florczyk et al. 2011 Free Radie. Biol. Med. 51: 1882-92.
Gautier et al. 1987 Nucleic Acids. Res. 15: 6625-6641.
Giatromanolaki et al. 2003 Melanoma Res. 13: 493-501.
Giatromanolaki et al. 2006 App. Imm. Mol. Morph. 14: 78-82.
Giatromanolaki et al. 2012 Clin. Exp. Metastasis 29: 11-7.
Griffiths et al. 2008 Br. J. Cancer 98: 965-973.
Guo et al. J. Kanazawa Med. U. 31: 10-16.
Henschel et al. 2004, "DEQOR: a web-based tool for the design and quality control of siRNAs." Nucleic Acids Research, vol. 32 (Web Server Issue): W113-W120.
Hogenesch et al. 1997 J. Biol. Chem. 272: 8581-8593.
Holmquist-Mengelbier et al. 2006 Cancer Cell 10: 413-23.
Hutvagner et al. 2001 Science 293: 834-838.
Inoue et al. 1987 Nucleic Acids Res. 15: 6131-6148.
Inoue et al. 1987 FEBS Lett. 215: 327-330.
Ioachim et al. 2006 Urol. Int. 77: 255-263.
Ke et al. Zhonghua Yi Xue Yi Chuan Xue Za Zhi. Oct. 2011; 28(5):583-8; PMID: 21983741.
Jiang, et al. 1996 J. Biol. Chem. 271: 17771-17778.
Gambling, et al. 2 Kidney Ints. 65: 1774-1781.
Koh et al. 2011 cancer Res. 71:4015-4027.
Kondo et al. 2002. Cancer Cell 1 :237-246.
Kondo et al. 2003. PLoS Biology 1 :439-444.
Kraynack et al. 2006 RNA 12: 163-176.
Loakes 2001 Nucl. Acids Res. 29: 2437-2447.
Maynard et al. 2007 Cell. Mol. Life Sci. 64: 2170-2180.
McCaffrey et al. Nature 418: 38-39.
Miller et al. 1998 Biochemistry 37: 12875-12883.
Mutter et al. 2008 Microvascular Research 75: 1-8.
Nesbit et al. 1999 Oncogene 18: 3004-3016.
Nykanen, et al. 2001 Cell 107:309-321.
Osada et al. 2007 Human Pathol. 38: 1310-1320.
Ovcharenko (2005) "Efficient delivery of siRNAs to human primary cells." Ambion TechNotes.
Parrish et al. 2000 Molecular Cell 6: 1077-1087.
Pelengaris et al. 2002 Nat. Re. Cancer 2: 764-776.
Rasheed et al. 2009 Br. J. Cancer 100: 1666-1673.
Roda, Julie, et al: "Hypoxia-inducible factor-2[alpha] regulates GM-CSF-derived soluble vascular endothelial growth factor receptor 1 production from macrophages and inhibits tumor growth and angiogenesis.", Journal of Immunology (Baltimore, MD.: 1950) Aug. 15, 2011, vol. 187, No. 4, Aug. 15, 2011, pp. 1970-1976.
Schiffelers et al. 2004 Nucl. Acids Res. 32: el49, 1-10.
Scortegagna et al. Nat. Genet. 35: 331-340.
Sharp et al. 2001 Genes Dev. 15:485-490.
Sioud and Sorensen 2003, Biochemical and Biophysical Research Communications 312, 1220-1225.
Sioud 2005 J. Mol. Biol. 348:1079-1090.
Smith et al. 2008 Br. J. Haematol. 141: 325-34.
Song et al.(Nat Med. published online (Feb. 10, 2003) doi: 10.1038/nm828), 347-351.
Song et al. 2005 Nat Biotech. 23:709-717.
Sun et al. 2008 Nature Biotech. 26: 1379-1382.
Tian et al. 1998 Genes Dev. 12:3320-3324.
Usman et al. 1992 TIBS 17:334-339.
Usman et al. 1994 Nucl. Acids Symp. Ser. 31: 163-164.
van Patot et al. 2011 High Alt. Med. Biol. 12: 157-67.
Veeranna et al. 2012 J. Virol. 86: 1097-1108.
Wang et al. 1995 Proc. Natl. Acad. Sci. USA 92: 5510-14.
Xu et al. 2012 Oncogene 31: 1065-72.
Yamato et al. 2011 cancer Gene Ther. 18: 587-597.
Zimmer et al. 2004. Molecular Cancer Research 2:89-95.
Pelengaris et al. 1999 Mol. Cell 3(5): 565-577.
International Search Report and the Written Opinion for corresponding Application PCT/US2014/018873.

* cited by examiner

U002
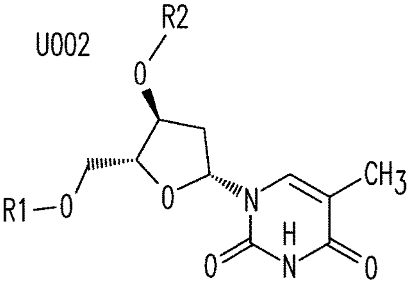
U003
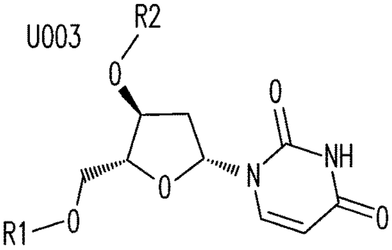
U004
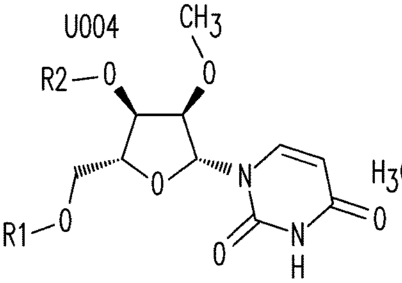
U005
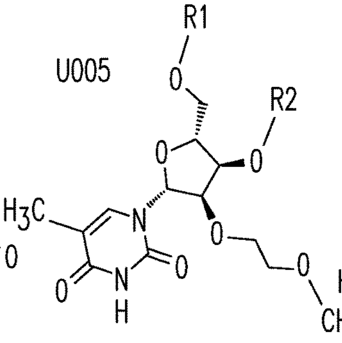
C004
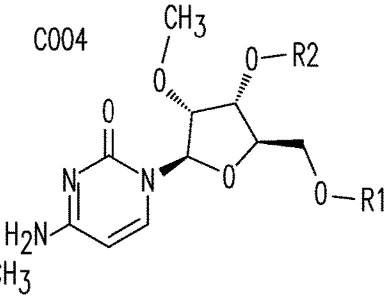
C005
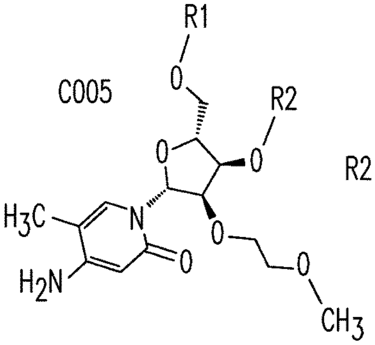
A004
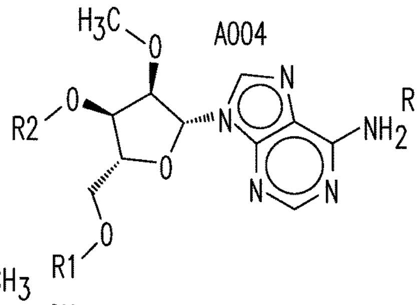
A005
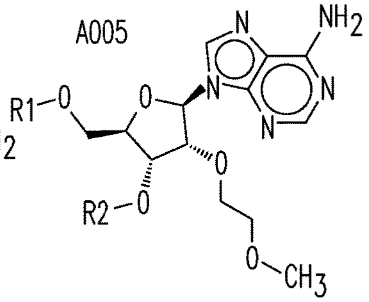
G004
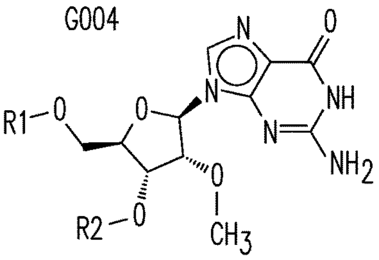
G005
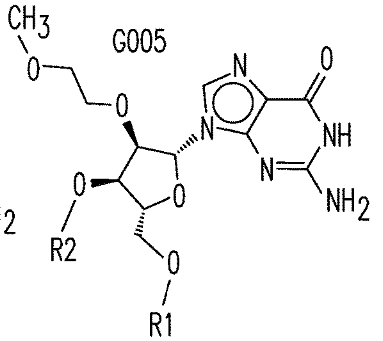

ORGANIC COMPOSITIONS TO TREAT EPAS1-RELATED DISEASES

PRIORITY

This application is a 371 U.S. National Application of PCT/US2014/018873, filed on Feb. 27, 2014, which claims priority to U.S. Provisional Application No. 61/770,713, filed on Feb. 28, 2013, the entire contents of both of which are incorporated herein by reference.

SEQUENCE LISTING

This application contains a Sequence Listing which has been submitted electronically in ASCII format. The ASCII copy, created on Apr. 20, 2015, is named "N054421-WO1_SequenceListing.txt" and is 95.5 kb in size.

BACKGROUND OF THE INVENTION

EPAS1 is a member of the HIF (hypoxia inducible factor) gene family. Also known as Hif2 alpha, EPAS1 encodes half of a transcription factor involved in the induction of genes regulated by oxygen, and which is induced as oxygen levels fall (a condition known as hypoxia).

Certain variants of this gene provide protection for people living at high altitude. However, at low altitude, over-expression of wild-type (WT) EPAS1 is associated with increased hypertension and stroke, and with symptoms similar to mountain sickness. Mutations in this gene are also associated with erythrocytosis familial type 4 and pulmonary hypertension. EPAS1 can also cause excessive production of red blood cells, leading to inhibited reproductive abilities or even death.

EPAS1 is also required for or enhances the expression of various genes involved in an assortment of diseases, including tumor progression. For example, EPAS1 plays an important role in the progression of uveal melanomas, possibly by promoting the autocrine loop VEGF-pVEGFR2/KDR, and by enhancing the expression of LDHA, thus conferring a growth advantage.

EPAS1 is also involved in or upregulates expression of many factors, including: c-Myc (which favors cell proliferation, transformation, neoplasia and tumorigenesis, and which is highly expressed in most cancers); Interleukin 8 (a proinflammatory mediator, e.g., in gingivitis and psoriasis); SP-1 (a transcription factor involved in IL-8 regulation and a coactivator of c-Myc); LDH5 (which is linked with tumor necrosis and increased tumor size); and LANA (Latency Associated Nuclear Antigen, which is associated with Kaposi's sarcoma-associated Herpesvirus). In addition, HIF (hypoxia induced factor) activity is involved in angiogensis required for cancer tumor growth. EPAS1 is also involved in several other diseases, including inflammation, including chronic inflammation, neovascular diseases, rheumatoid arthritis, renal cancer, clear cell renal cell carcinoma (and metastases of this and other cancers), melanoma, uveal melanoma, chondrosarcoma, and multiple myeloma.

There thus exists the need for treatments related to these and other EPAS1-related diseases.

BRIEF SUMMARY OF THE INVENTION

The present disclosure encompasses RNAi agents to EPAS1 (Hif2 alpha), for inhibition of EPAS1, and which are useful in treatment of EPAS1-related diseases, such as cancer, metastases, astrocytoma, bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, non-small cell lung cancer, melanoma, multiple myeloma, ovarian cancer, rectal cancer, renal cancer, clear cell renal cell carcinoma (and metastases of this and other cancers), gingivitis, psoriasis, Kaposi's sarcoma-associated herpesvirus, preemclampsia, inflammation, chronic inflammation, neovascular diseases, and rheumatoid arthritis.

The present disclosure also encompasses a method of treating a human subject having a pathological state mediated at least in part by EPAS1 expression, the method comprising the step of administering to the subject a therapeutically effective amount of a RNAi agent to EPAS1.

The method also optionally further comprises the step of administering a second agent. In some aspects, this second agent is another RNAi agent to EPAS1 (e.g., a RNAi agent which targets a different sequence within the EPAS1 target). In other aspects, the second agent is another treatment, such as one directed to another target, which is also hyper-active, mutated and/or over-expressed in the pathological state.

The present disclosure provides specific RNAi agents for inhibition of EPAS1, and methods that are useful in reducing EPAS1 levels in a subject, e.g., a mammal, such as a human. The present disclosure specifically provides double-stranded RNAi agents comprising at least 15 or 19 or more contiguous nucleotides of EPAS1. In particular, the present disclosure provides agents comprising sequences of 15 or more contiguous nucleotides differing by 0, 1, 2 or 3 from those of any of the RNAi agents provided, e.g., in any table herein, such as Tables 1 to 5 (including all parts of Table 5, from Table 5A to 5E). The RNAi agents particularly can in one aspect comprise less than 30 nucleotides per strand, e.g., such as 17-23 nucleotides, 15-19, 18-22, and/or 19-21 nucleotides, and/or such as those provided, e.g., in Tables 1 to 5, and modified and unmodified variants thereof (e.g., wherein the sense and/or anti-sense or first and/or second strand are modified or unmodified). The present disclosure also provides agents comprising a sense strand and an anti-sense strand, wherein the sense and/or the anti-sense strand comprise sequences of 19 or more contiguous nucleotides differing by 0, 1, 2 or 3 from those of the RNAi agents provided, e.g., in Tables 1 to 5, and modified or unmodified variants thereof. The sense and anti-sense strand can be contiguous, or physically connected, e.g., by covalently bonds, a loop or linker.

The double-stranded RNAi agents can have 0, 1 or 2 blunt ends, and/or overhangs of 1, 2, 3 or 4 nucleotides (i.e., 1 to 4 nt) from one or both 3' and/or 5' ends. The double-stranded RNAi agents can also optionally comprise one or two 3' caps and/or one or more modified nucleotides. Modified variants of sequences as provided herein include those that are otherwise identical but contain substitutions of a naturally-occurring nucleotide for a corresponding modified nucleotide.

Furthermore, the RNAi agent can either contain only naturally-occurring ribonucleotide subunits, or one or more modifications to the sugar, phosphate or base of one or more of the replacement nucleotide subunits, whether they comprise ribonucleotide subunits or deoxyribonucleotide subunits. In one aspect, modified variants of the disclosed RNAi agents have a thymidine (as RNA, or, preferably, DNA) replacing a uridine, or have an inosine base. In some aspects, the modified variants of the disclosed RNAi agents can have a nick in the passenger strand, mismatches between the guide and passenger strand, DNA replacing the RNA of a portion of both the guide and passenger strand (e.g., the seed region), and/or a shortened passenger strand (e.g., 13, 14, 15, 16, 17 or 18 nt). Once a functional guide strand is identified, modifications and variants of the RNAi agent can be readily made. Any two or more modifications which are not mutually exclusive can be combined (e.g., the combination of base modifications with shortened passenger strand; or nicked passenger strand and base modifications; or DNA replacing part or all of the seed region and base modifications in the remaining RNA; etc.). Any sequence or any portion thereof (e.g., 19 [or more] contiguous nt; 15 [or more] contiguous nt; 15 [or more] contiguous nt differing by 0, 1, 2 or 3 nt) disclosed herein can be used with any modification or modification scheme disclosed herein, provided they are not mutually exclusive (e.g., refer to different lengths of strands). The sequences (and any portions thereof) of RNAi agents can be used with any modification, set of modifications (e.g., modification scheme), vehicle, composition, method, treatment, etc., described herein, provided they are not mutually exclusive.

In one aspect, modified variants of the disclosed RNAi agents include RNAi agents with the same sequence (e.g., the same sequence of bases) as any RNAi agent disclosed in any of Tables 1 to 5, but with one or more modifications to one or more of the sugar or phosphate of one or more of the nucleotide subunits. In one aspect, the modifications improve efficacy, stability (e.g., against nucleases in, for example, blood serum or intestinal fluid), and/or reduce immunogenicity of the RNAi agent. One aspect of the present disclosure relates to a double-stranded oligonucleotide comprising at least one non-natural nucleobase. These include universal base analogues, e.g., those described by Loakes 2001 Nucl. Acids Res. 29: 2437-2447. In certain aspects, the non-natural nucleobase is difluorotolyl, nitroindolyl, nitropyrrolyl, or nitroimidazolyl. In a particular aspect, the non-natural nucleobase is difluorotolyl. In certain aspects, only one of the two oligonucleotide strands contains a non-natural nucleobase. In certain aspects, both of the oligonucleotide strands contain a non-natural nucleobase.

The RNAi agent(s) can optionally be attached to a ligand selected to improve one or more characteristic, such as, e.g., stability, distribution and/or cellular uptake of the agent, e.g., cholesterol or a derivative thereof. The RNAi agent(s) can be isolated or be part of a pharmaceutical composition used for the methods described herein. Particularly, the pharmaceutical composition can be formulated for delivery to specific tissues (e.g., those afflicted with a EPAS1-related disease) or formulated for parenteral administration. The pharmaceutical composition can optionally comprise two or more RNAi agents, each one directed to the same, overlapping or a different segment of the EPAS1 mRNA. Optionally, the pharmaceutical composition can further comprise or be used in conjunction with any known treatment for any EPAS1-related disease.

The present disclosure further provides methods for reducing the level of EPAS1 mRNA in a cell, particularly in the case of a disease characterized by over-expression or hyper-activity of EPAS1. Cells comprising an alteration such as a mutation, over-expression and/or hyperactivity of EPAS1 are termed "EPAS1-defective" cells. Such methods comprise the step of administering one or more of the RNAi agents of the present disclosure to an EPAS1-defective cell, as further described below. The present methods utilize the cellular mechanisms involved in RNA interference to selectively degrade the target RNA in a cell and are comprised of the step of contacting a cell with one of the RNAi agents of the present disclosure.

The present disclosure also encompasses a method of treating a human subject having a pathological state mediated at least in part by EPAS1 expression, the method comprising the step of administering to the subject a therapeutically effective amount of a RNAi agent EPAS1. Additional methods involve preventing, treating, modulating and/or ameliorating a pathological state wherein disease progression (e.g., tumor growth) requires EPAS1, although EPAS1 is not amplified or over-expressed. Such methods comprise the step of administering one of the RNAi agents of the present disclosure to a subject, as further described below. Such methods can be performed directly on a cell or can be performed on a mammalian subject by administering to a subject one of the RNAi agents/pharmaceutical compositions of the present disclosure. Reduction of target EPAS1 RNA in a cell results in a reduction in the amount of encoded EPAS1 protein produced. In an organism, this can result in restoration of balance in a pathway involving EPAS1, and/or prevention of EPAS1 accumulation, and/or a reduction in EPAS1 activity and/or expression, and/or prevention of EPAS1-mediated activation of other genes, and/or amelioration, treatment and/or prevention of a EPAS1-related disease. In one aspect, a reduction in EPAS1 expression, level or activity can limit tumor growth.

The methods and compositions of the present disclosure, e.g., the methods and EPAS1 RNAi agent compositions, can be used in any appropriate dosage and/or formulation described herein or known in the art, as well as with any suitable route of administration described herein or known in the art.

The details of one or more aspects of the present disclosure are set forth in the accompanying drawings and the description below. Elements of the various aspects (e.g., sequences or portions thereof [e.g., 15 or more contiguous nt differing by 0, 1, 2 or 3 nt], lengths, modifications, terminal dinucleotides, endcaps, combinations of RNAi agents, combination therapy involving a EPAS1 RNAi agent and another agent, conjugation with other components, compositions or methods or techniques for delivery, disease treatment, etc.) disclosed herein or known in the art which are not mutually exclusive can be combined with each other, provided that the agent or agents are still capable of mediating RNA interference. For example, any RNAi agent sequence disclosed herein can be combined with any set of modifications or endcaps disclosed herein. Similarly, any combination of modifications, 5' end caps, and/or 3' end caps can be used with any RNAi agent sequence disclosed herein. Any RNAi agent disclosed herein (with any combination of modifications or endcaps or without either modifications or endcaps) can be combined with any other RNAi agent or other treatment composition or method disclosed herein.

Other features, objects, and advantages of the present disclosure will be apparent from this description, the drawings, and from the claims.

BRIEF DESCRIPTION OF THE FIGURE

FIG. 1 illustrates various example modified nucleotides which have been or can be used in modified variants of EPAS1 RNAi agents: U002, U003, U004, U005, C004, C005, A004, A005, G005, and G004, which can be used in the RNAi agents disclosed herein. U002 indicates a 2'-deoxy-thymidine which is DNA. U003 indicates 2'-deoxy uridine. U004 indicates a nucleotide with a Uridine ("U") base with a 2'-O-methyl modification. U005 indicates a U base with a 2'-O-methoxyethyl (MOE) modification. C004 indicates a Cytosine ("C") base with a 2'-O-methyl modification. C005 indicates a C base with 2'-O-methoxyethyl modification. A004 indicates an Adenosine ("A") base with a 2'-O-methyl modification. A005 indicates an A base with 2'-O-methoxyethyl modification. G005 indicates a Guanosine ("G") base with a 2'O-methyl modification. G004 indicates a G base with a 2'O-methyl modification.

DETAILED DESCRIPTION OF THE INVENTION

The present disclosure encompasses RNAi agents to EPAS1, for targeting and inhibition of EPAS1, which are useful in treatment of EPAS1-related diseases (e.g., diseases associated with mutations in and/or altered expression, level and/or activity of EPAS1, diseases requiring EPAS1, diseases affected by a factor whose expression, over-expression, or hyper-activity is directly or indirectly affected by EPAS1, and/or diseases treatable by modulating the expression, level and/or activity of EPAS1). Such EPAS1-related diseases include: cancer, metastases, astrocytoma, bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, non-small cell lung cancer, melanoma, multiple myeloma, ovarian cancer, rectal cancer, renal cancer, clear cell renal cell carcinoma (and metastases of this and other cancers), gingivitis, psoriasis, Kaposi's sarcoma-associated herpesvirus, preemclampsia, inflammation, chronic inflammation, neovascular diseases, and rheumatoid arthritis. The present disclosure also provides methods of treating a human subject having a pathological state mediated at least in part by EPAS1 expression or over-expression or hyper-activity, or requiring EPAS1, the method comprising the step of administering to the subject a therapeutically effective amount of a RNAi agent to EPAS1.

Various Aspects of the Disclosure Include the Following.

An RNAi Agent Comprising an Antisense Strand of an RNAi Agent Described Herein.

In one aspect, an aspect of the present disclosure relates to a composition comprising an RNAi agent comprising an antisense strand, wherein the antisense strand comprises at least 15 contiguous nucleotides (nt) differing by 0, 1, 2, or 3 nucleotides from the antisense strand of an RNAi agent to EPAS1 selected from any sequence provided herein (e.g., in any one or more of Tables 1 to 5, etc.). In another aspect, the present disclosure relates to a composition comprising an RNAi agent comprising a first strand and a second strand, wherein the first strand comprises at least 15 contiguous nucleotides differing by 0, 1, 2, or 3 nucleotides from the first strand of an RNAi agent to EPAS1 from any sequence provided herein. In another aspect, the present disclosure relates to a composition comprising an RNAi agent comprising a sense strand and an antisense strand, wherein the sense strand comprises at least 15 contiguous nucleotides differing by 0, 1, 2, or 3 nucleotides from the sense strand and the antisense strand comprises at least 15 contiguous nucleotides differing by 0, 1, 2, or 3 nucleotides from the antisense strand of an RNAi agent to EPAS1 listed immediately above. In another aspect, the present disclosure relates to a composition comprising an RNAi agent comprising a first strand and a second strand, wherein the sequence of the first strand comprises the sequence of the first strand of any sequence provided herein. In another aspect, the present disclosure relates to a composition comprising an RNAi agent comprising a first strand and a second strand, wherein the sequence of the first strand is the sequence of the first strand of any sequence provided herein. In various aspects, the first and second strands are the anti-sense and sense strand, respectively, of any RNAi agent disclosed herein. In various aspects, the first and second strands are the sense and anti-sense strand, respectively, of any RNAi agent disclosed herein.

Particular duplexes include the unmodified (e.g., "generic") and example modified variants listed in Table 1; additional sequences and data for these RNAi agents are presented in the subsequent Tables. In addition to the described example modifications, other modified variants can be made using the nucleotide sequences provided. In various aspects, the first and/or second strand are modified or unmodified.

Tables

Provided in Table 1 are the names of EPAS1 RNAi agents (derived from their position in the human EPAS1 gene sequence NM 001430), along with the SEQ ID NOs. representing the DNA sequence, unmodified sequence, and example modified sequences (with both A51 S26 and A85 S26 example modified sequences). Both sense and antisense (AS) sequences are presented in these Tables.

Table 2 provides the DNA sequences.

Table 3 provides the unmodified sequences of the RNAi agents.

Table 4 indicates whether or not particular RNAi agent sequences (which are derived from human) also correspond to those from mouse (Mu or mm), rat (Ra or rn), and Rhesus [mmu or *Macaca mulatta]*.

Table 5 (comprising Tables 5A to 5E) list example modified RNAi agent sequences.

Tables 6 to 8 show efficacy of various EPAS1 RNAi agents in vitro and in vivo.

Table 9 shows overlapping groups of these EPAS1 RNAi agents.

TABLE 1

SEQ ID NOs for various EPAS1 RNAi agents. Presented are the SEQ ID NOs. representing the DNA sequence, unmodified sequence, and example modified sequences (with both A51 S26 and A85 S26 example modified sequences).

| | DNA | | Unmodified RNAi agent | | Example Modified (A51 S26) | | Example Modified (A85 S26) | |
|---|---|---|---|---|---|---|---|---|
| Name Position NM 001430 | Sense SEQ ID NO: | AS SEQ ID NO: | Sense SEQ ID NO: | Antisense SEQ ID NO: | SENSE SEQ ID NO: | AS SEQ ID NO: | Sense SEQ ID NO: | AS SEQ ID NO: |
| 842 | 1 | 20 | 39 | 58 | 145 | 126 | 77 | 96 |
| 2802 | 2 | 21 | 40 | 59 | 146 | 127 | 78 | 97 |
| 3040 | 3 | 22 | 41 | 60 | 147 | 128 | 79 | 98 |
| 3304 | 4 | 23 | 42 | 61 | 148 | 129 | 80 | 99 |
| 3310 | 5 | 24 | 43 | 62 | 149 | 130 | 81 | 100 |
| 3345 | 6 | 25 | 44 | 63 | 150 | 131 | 82 | 101 |
| 3354 | 7 | 26 | 45 | 64 | 151 | 132 | 83 | 102 |
| 3735 | 8 | 27 | 46 | 65 | 152 | 133 | 84 | 103 |
| 3739 | 9 | 28 | 47 | 66 | 153 | 134 | 85 | 104 |
| 3875 | 10 | 29 | 48 | 67 | 154 | 135 | 86 | 105 |
| 4153 | 11 | 30 | 49 | 68 | 155 | 136 | 87 | 106 |
| 4157 | 12 | 31 | 50 | 69 | 156 | 137 | 88 | 107 |
| 5049 | 13 | 32 | 51 | 70 | 157 | 138 | 89 | 108 |
| 5057 | 14 | 33 | 52 | 71 | 158 | 139 | 90 | 109 |
| 5058 | 15 | 34 | 53 | 72 | 159 | 140 | 91 | 110 |
| 5059 | 16 | 35 | 54 | 73 | 160 | 141 | 92 | 111 |
| 5108 | 17 | 36 | 55 | 74 | 161 | 142 | 93 | 112 |
| 5144 | 18 | 37 | 56 | 75 | 162 | 143 | 94 | 113 |
| 5149 | 19 | 38 | 57 | 76 | 163 | 144 | 95 | 114 |

Additional modified variants of EPAS1 RNAi agents are shown in Tables 5C to 5E.

Table 1 thus presents the SEQ ID NO identifiers of the sense and anti-sense strands of unmodified and an example modified EPAS1 RNAi agents. For example, in this Table, the unmodified sense and anti-sense sequences of RNAi agent 842 are represented by SEQ ID NOs.: 39 and 58, respectively. A modified variant of this RNAi agent is represented by SEQ ID NOs: 145 and 126; another example modified variant is represented by SEQ ID NOs: 77 and 96. Also note that the name (e.g., 842) is derived from the position number in the human EPAS1 gene sequence NM 001430. These names are sometimes prefixed with "EPAS1" or "EPAS1_" (e.g., "EPAS1 842" or "EPAS1_842"). Also note that the prefix "AD" is on occasion replaced by "ND". The name of the RNAi agent also sometimes has a suffix, such as 0.1. This indicates a particular variant. Thus, "842" and "EPAS1_842" and the like all indicate RNAi agents of the same sequence, although they may differ in modifications.

In the sequences in Tables 5, lower-case letters (e.g., c, u) indicate modified nucleotides while upper case letters (e.g., C, U, A, G) indicate unmodified nucleotides. In this Table, example modified versions of each of the sequences are shown. However, the present disclosure also contemplates and encompasses unmodified versions of these sequences and other versions which comprise additional or alternative modifications.

In the sequences in the Tables, the modified and unmodified variants can optionally further comprise the sequence "TT", "dTdT", "dTsdT" or "UU" as a single-stranded overhang at the 3' end, also termed herein a terminal dinucleotide or 3' terminal dinucleotide. dT is 2'-deoxy-thymidine-5'-phosphate and sdT is 2'-deoxy Thymidine 5'-phosphorothioate. In the disclosed sequences, terminal dinucleotide "UU" is UU or 2'-OMe-U 2'-OMe-U, and the terminal TT and the terminal UU can be in the inverted/reverse orientation. The terminal dinucleotide (e.g., UU) is not part of the EPAS1 target sequence, but is a modified variant of the dithymidine dinucleotide commonly placed as an overhang to protect the ends of siRNAs from nucleases (see, for example, Elbashir et al. 2001 Nature 411: 494-498; Elbashir et al. 2001 EMBO J. 20: 6877-6888; and Kraynack et al. 2006 RNA 12:163-176). A terminal dinucleotide is known from these references to enhance nuclease resistance but not contribute to target recognition. Thus, the present disclosure also encompasses any modified or any unmodified variant disclosed herein, wherein the modified variant comprises a terminal TT, dTdT, sdT, dTsdT, sdTsdT, sdTdT, or the like which may be in either the inverted/reverse orientation or in the same 5' to 3' orientation as the EPAS1 specific sequence in the duplex. In addition, terminology used herein referring to "the EPAS1 portion of a RNAi agent sequence" and the like indicate the portion of the sequence of a RNAi agent which is derived from EPAS1 (thus "the EPAS1 portion of a RNAi agent sequence" does not include, for example, a terminal dTdT, TT, UU, U (2'-OMe) dT, U (2'-OMe) U (2'-OMe), T(2'-OMe) T (2'-OMe), T(2'-OMe) dT, or the like, but does include the portion of the RNAi agent that corresponds to or is complementary to a portion of the EPAS1 gene sequence or mRNA sequence. In one aspect, the composition comprises a RNAi agent comprising a first and an second strand, wherein the sequence of the first strand and the sequence of the second strand are the sequences of the first and second strand, respectively, of any RNAi agent provided herein, further comprising a 3' terminal dinucleotide (a single-stranded overhang comprising 2 nt at the 3' end). In one aspect, the composition comprises a RNAi agent comprising a first and an second strand, wherein the sequence of the first strand and the sequence of the second strand are the sequences of the first and second strand, respectively, of any RNAi agent provided herein, further comprising a 3' terminal dinucleotide selected from TT, UU, U (2'-OMe) dT, U (2'-OMe) U (2'-OMe), T(2'-OMe) T (2'-OMe), T(2'-OMe) dT, dTdT, sdT, dTsdT, sdTsdT, and sdTdT. In one aspect, the composition comprises a RNAi agent comprising a first and an second strand, wherein the sequence of the first strand and the sequence of the second strand are the sequences of the first and second strand, respectively, of any RNAi agent provided herein, further comprising a 3' terminal UU dinucleotide.

On any modified or unmodified variant, a 3' end cap, as is known in the art, can be used instead of or in addition to a terminal dinucleotide to stabilize the end from nuclease degradation provided that the 3' end cap is able to both stabilize the RNAi agent (e.g., against nucleases) and not interfere excessively with siRNA activity. Thus, the present disclosure also encompasses any modified or any unmodified variant disclosed herein, wherein the modified variant further comprises a terminal 3' end cap.

An RNAi Agent Comprising an Antisense Strand of an RNAi Agent Described Herein.

In one particular specific aspect, the present disclosure relates to a composition comprising an RNAi agent comprising an antisense strand, wherein the antisense strand comprises at least 15 contiguous nucleotides differing by 0, 1, 2, or 3 nucleotides from the antisense strand of an RNAi agent to EPAS1 selected from those antisense strands in the specific duplexes provided above and as listed in Table 1.

Various particular specific aspects of this aspect are described below.

In one aspect, the composition further comprises a second RNAi agent to EPAS1. In various aspects, the second RNAi agent is physically separate from the first, or the two are physically connected (e.g., covalently linked or otherwise conjugated).

In one aspect, the composition comprises a RNAi agent comprising a first and an second strand, wherein the sequence of the first strand and the sequence of the second strand are the sequences of the first and second strand, respectively, of any RNAi agent provided herein. In one aspect, the composition comprises a RNAi agent comprising a first and an second strand, wherein the sequence of the first strand and the sequence of the second strand are the sequences of the first and second strand, respectively, of any RNAi agent provided herein, further comprising an additional about 6 to 20 nucleotides on one or both strands (e.g., about 6, 7, 8, 9, 10, 11, 12, 13, 14, 15, 16, 17, 18, 19 or 20 nt). In one aspect, the composition comprises a RNAi agent comprising a first and an second strand, wherein the sequence of the first strand and the sequence of the second strand are the sequences of the first and second strand, respectively, of any RNAi agent provided herein, further comprising a 3' terminal dinucleotide. In one aspect, the composition comprises a RNAi agent comprising a first and an second strand, wherein the sequence of the first strand and the sequence of the second strand are the sequences of the first and second strand, respectively, of any RNAi agent provided herein, further comprising a 3'terminal dinucleotide selected from TT, UU, U (2'-OMe) dT, U (2'-OMe) U (2'-OMe), T(2'-OMe) T (2'-OMe), T(2'-OMe) dT, dTdT, sdT, dTsdT, sdTsdT, and sdTdT. In one aspect, the composition comprises a RNAi agent comprising a first and an second strand, wherein the sequence of the first strand and the sequence of the second strand are the sequences of the first and second strand, respectively, of any RNAi agent provided herein, further comprising a 3'terminal UU dinucleotide. In various aspects, the first and second strands are the sense and anti-sense strands listed in the Tables herein, respectively. In various aspects, the first and second strands are the anti-sense and sense strands listed in the Tables herein, respectively.

In one aspect, the sense strand is about 30 or fewer nucleotides (nt) in length.

In one aspect, the antisense strand is about 30 or fewer nucleotides in length.

In one aspect, the antisense strand forms a duplex region with a sense strand, wherein the duplex region is about 15 to 30 nucleotide pairs in length.

In one aspect, the antisense strand is about 15 to about 30 nucleotides in length, including about 19 to about 23 nucleotides in length. In one aspect, the antisense strand has at least the length selected from about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides and 30 nucleotides.

In one aspect, the RNAi agent comprises a modification that causes the RNAi agent to have increased stability in a biological sample or environment (e.g., cytoplasm, interstitial fluid, blood serum, or lung or intestinal lavage).

In one aspect, the RNAi agent comprises at least one sugar backbone modification (e.g., phosphorothioate linkage) or at least one 2'-modified nucleotide.

In one aspect, the RNAi agent comprises: at least one 5'-uridine-adenine-3' (5'-ua-3') dinucleotide, wherein the uridine is a 2'-modified nucleotide; at least one 5'-uridine-guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; or at least one 5'-uridine-uridine-3' (5'-uu-3') dinucleotide, wherein the 5'-uridine is a 2'-modified nucleotide. These dinucleotide motifs are particularly prone to serum nuclease degradation (e.g. RNase A). Chemical modification at the 2'-position of the first pyrimidine nucleotide in the motif prevents or slows down such cleavage. This modification recipe is also known under the term ‘endo light’.

In one aspect, the RNAi agent comprises a 2'-modification selected from the group consisting of: 2'-deoxy, 2'-deoxy-2'-fluoro, 2'-O-methyl (2'-OMe or 2' OMe), 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA). In one aspect, all pyrimidines (uridine and cytidine) are 2' O-methyl-modified nucleosides.

In another aspect, the RNAi agent comprises a 2'-modification selected from the group consisting of:

In one aspect, the RNAi agent comprises at least one blunt end.

In one aspect, the RNAi agent comprises an overhang having 1 nt to 4 nt unpaired.

In one aspect, the RNAi agent comprises an overhang at the 3'-end of the antisense strand of the RNAi agent.

In one aspect, the RNAi agent is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

In one aspect, the RNAi agent is capable of inhibiting expression of EPAS1 by at least about 50% in 786-O tumors in nude mice.

In one aspect, the RNAi agent is capable of inhibiting expression of EPAS1 by at least about 70% at a concentration of 10 nM in 786-O cells in vitro.

In one aspect, the RNAi agent is capable of inhibiting expression of EPAS1 by at least about 75% at a concentration of 10 nM in 786-O cells in vitro.

In one aspect, the RNAi agent is capable of inhibiting expression of EPAS1 by at least about 80% at a concentration of 10 nM in 786-O cells in vitro.

In one aspect, the RNAi agent is capable of inhibiting expression of EPAS1 by at least about 90% at a concentration of 10 nM in 786-O cells in vitro.

In one aspect, the RNAi agent is capable of inhibiting expression of EPAS1 by at least about 95% at a concentration of 10 nM in 786-O cells in vitro.

In one aspect, the RNAi agent is capable of inhibiting expression of EPAS1 by at least about 99% at a concentration of 10 nM in 786-O cells in vitro.

In one aspect, the RNAi has an EC50 of no more than about 0.1 nM in 786-O cells in vitro. EC50 is effective concentration to reduce gene expression by 50%.

In one aspect, the RNAi has an EC50 of no more than about 0.01 nM in 786-O cells in vitro.

In one aspect, the RNAi has an EC50 of no more than about 0.001 nM in 786-O cells in vitro.

An RNAi Agent Comprising a Sense and Antisense Strand of an RNAi Described Herein.

In one particular specific aspect, the present disclosure relates to a composition comprising a RNAi agent comprising a first strand and a second strand, wherein the sequence of the first strand and/or second strand comprise at least 15 contiguous nucleotides, differing by 0, 1, 2, or 3 nucleotides from the sequence of the first and/or second strand of a RNAi agent to EPAS1 selected from the specific duplexes provided herein and listed, e.g., in any Table herein. In one particular specific aspect, the present disclosure relates to a composition comprising a RNAi agent comprising a first strand and a second strand, wherein the sequence of the first strand and/or second strand comprise at least 15 contiguous nucleotides from the sequence of the first and/or second strand of a RNAi agent to EPAS1 selected from the specific duplexes provided herein and listed, e.g., in any Table herein. In one particular specific aspect, the present disclosure relates to a composition comprising a RNAi agent comprising a first strand and a second strand, wherein the sequence of the first strand and/or second strand comprise at least 19 contiguous nucleotides (e.g., nt 1-19, nt 2-20, nt 3-21, etc.) from the sequence of the first and/or second strand of a RNAi agent to EPAS1 selected from the specific duplexes provided herein and listed, e.g., in any Table herein.

In one particular specific aspect, the present disclosure relates to a composition comprising a RNAi agent comprising a first strand and a second strand, wherein the sequence of the first strand and/or second strand comprise the sequence of the first and/or second strand, respectively, of a RNAi agent to EPAS1 selected from the specific duplexes provided herein and listed, e.g., in any Table herein.

In one particular specific aspect, the present disclosure relates to a composition comprising a RNAi agent comprising a first strand and a second strand, wherein the sequence of the first strand and/or second strand are the sequence of the first and/or second strand, respectively, of a RNAi agent to EPAS1 selected from the specific duplexes provided herein and listed, e.g., in any Table herein.

In one particular specific aspect, the present disclosure relates to a composition comprising a RNAi agent comprising a first strand and a second strand, wherein the sequence of the first strand and/or second strand are the sequence of the first and/or second strand, respectively, of a RNAi agent to EPAS1 selected from the specific duplexes provided herein and listed, e.g., in any Table herein, wherein the sequence of the first and/or second strand further comprise a terminal dinucleotide.

In one particular specific aspect, the present disclosure relates to a composition comprising a RNAi agent comprising a first strand and a second strand, wherein the sequence of the first strand and/or second strand are the sequence of the first and/or second strand, respectively, of a RNAi agent to EPAS1 selected from the specific duplexes provided herein and listed, e.g., in any Table herein, wherein the sequence of the first and/or second strand further comprise a terminal UU dinucleotide.

In one particular specific aspect, the present disclosure relates to a composition comprising an RNAi agent comprising a sense strand and an antisense strand, wherein the sense strand and antisense strand comprise at least 15 contiguous nucleotides differing by 0, 1, 2, or 3 nucleotides, from the sense and antisense strand, respectively, of an RNAi agent to EPAS1 selected from the specific duplexes provided above and as listed in Table 1. In one particular specific aspect, the present disclosure relates to a composition comprising an RNAi agent comprising a sense strand and an antisense strand, wherein the sense strand and antisense strand comprise at least 15 contiguous nucleotides from the sense and antisense strand, respectively, of an RNAi agent to EPAS1 selected from the specific duplexes provided above and as listed in Table 1. In one particular specific aspect, the present disclosure relates to a composition comprising an RNAi agent comprising a sense strand and an antisense strand, wherein the sense strand and antisense strand comprise at least 19 contiguous nucleotides (e.g., nt 1-19, nt 2-20, or nt 3-21) from the sense and antisense strand, respectively, of an RNAi agent to EPAS1 selected from the specific duplexes provided above and as listed in Table 1.

Various particular specific aspects of this aspect are described below.

In one aspect, the composition comprises a second RNAi agent to EPAS1. In various aspects, the second RNAi agent is physically separate from the first, or the two are physically connected (e.g., chemically linked or otherwise conjugated). In some aspects, the first and second RNAi agents are combined within the same composition (e.g., both in the same lipid nanoparticle).

In one aspect, the antisense strand is about 30 or fewer nucleotides in length.

In one aspect, the sense strand and the antisense strand form a duplex region about 15 to about 30 nucleotide pairs in length.

In one aspect, the antisense strand is about 15 to about 36 nt in length including about 18 to about 23 nt in length, and including about 19 to about 21 nt in length and about 19 to about 23 nt in length. In one aspect, the antisense strand has at least the length selected from about 15 nt, about 16 nt, about 17 nt, about 18 nt, about 19 nt, about 20 nt, about 21 nt, about 22 nt, about 23 nt, about 24 nt, about 25 nt, about 26 nt, about 27 nt, about 28 nt, about 29 nt and about 30 nt.

In one aspect, the RNAi agent comprises a modification that causes the RNAi agent to have increased stability in a biological sample or environment.

In one aspect, the RNAi agent comprises a modified sugar backbone such as, e.g., a phosphorothioate linkage, or comprises a 2'-modified nucleotide.

In one aspect, the RNAi agent comprises: at least one 5'-uridine-adenine-3' (5'-ua-3') dinucleotide, wherein the uridine is a 2'-modified nucleotide; at least one 5'-uridine-guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; or at least one 5'-uridine-uridine-3' (5'-uu-3') dinucleotide, wherein the 5'-uridine is a 2'-modified nucleotide.

In one aspect, the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA). In one aspect, all pyrimidines (uridine and cytidine) are 2' O-methyl-modified nucleosides.

In one aspect, the RNAi agent comprises at least one blunt end.

In one aspect, the RNAi agent comprises an overhang having 1 to 4 nt unpaired.

In one aspect, the RNAi agent comprises an overhang at the 3'-end of the antisense strand of the RNAi agent.

In one aspect, the RNAi agent is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

In one aspect, the RNAi agent is capable of inhibiting expression of EPAS1 by at least about 50% in 786-O tumors in nude mice.

In one aspect, the RNAi agent is capable of inhibiting expression of EPAS1 by at least about 70% at a concentration of 10 nM in 786-O cells in vitro.

In one aspect, the RNAi agent is capable of inhibiting expression of EPAS1 by at least about 80% at a concentration of 10 nM in 786-O cells in vitro.

In one aspect, the RNAi agent is capable of inhibiting expression of EPAS1 by at least about 90% at a concentration of 10 nM in 786-O cells in vitro.

In one aspect, the RNAi agent is capable of inhibiting expression of EPAS1 by at least about 95% at a concentration of 10 nM in 786-O cells in vitro.

In one aspect, the RNAi agent is capable of inhibiting expression of EPAS1 by at least about 99% at a concentration of 10 nM in 786-O cells in vitro.

In one aspect, the RNAi has an EC50 of no more than about 0.1 nM in 786-O cells in vitro.

In one aspect, the RNAi has an EC50 of no more than about 0.01 nM in 786-O cells in vitro.

In one aspect, the RNAi has an EC50 of no more than about 0.001 nM in 786-O cells in vitro.

A Method of Treatment Using a Composition Comprising a RNAi Agent Described Herein.

In one particular specific aspect, the present disclosure relates to a method of treating a EPAS1-related disease in an individual, comprising the step of administering to the individual a therapeutically effective amount of a composition comprising an RNAi agent comprising an antisense strand, wherein the antisense strand comprises at least 15 contiguous nucleotides differing by 0, 1, 2, or 3 nucleotides from the antisense strand of an RNAi agent to EPAS1 selected from those specific duplexes provided above and as listed in Table 1. In one aspect, the RNAi agent to EPAS1 comprises an antisense strand duplexed with a sense strand, wherein the sense and antisense strands are selected from one or more of the sequences provided in any of Tables 1 to 5.

Various particular specific aspects of this aspect are described below. Any aspects disclosed herein that are not mutually exclusive can be combined.

In one aspect, the present disclosure relates to such a method, wherein the composition comprising a RNAi agent further comprises a sense strand, wherein the sense strand comprises at least 15 contiguous nucleotides differing by 0, 1, 2, or 3 nucleotides from the sense strand of a RNAi agent to EPAS1 selected from the specific duplexes provided herein and as listed, e.g., in any Table herein.

In one aspect of the method, the RNAi agent comprises at least an anti-sense strand, and/or comprises a sense and an anti-sense strand, wherein the sequence of the sense and/or anti-sense strand is the sequence of the sense and/or the anti-sense strand of a RNAi agent to EPAS1 selected from those specific duplex provided herein and as listed, e.g., in Table 1, wherein the composition further comprises a pharmaceutically effective formulation.

In one aspect of the method, the RNAi agent comprises at least an anti-sense strand, and/or comprises a sense and an anti-sense strand, wherein the sequence of the sense and/or anti-sense strand comprises the sequence of the sense and/or the anti-sense strand of a RNAi agent to EPAS1 selected from those specific duplex provided herein and as listed, e.g., in Table 1, wherein the composition further comprises a pharmaceutically effective formulation.

In one aspect, the EPAS1-related disease is cancer, metastases, astrocytoma, bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, non-small cell lung cancer, melanoma, multiple myeloma, ovarian cancer, rectal cancer, renal cancer, clear cell renal cell carcinoma (and metastases of this and other cancers), gingivitis, psoriasis, Kaposi's sarcoma-associated herpesvirus, preemclampsia, inflammation, chronic inflammation, neovascular diseases, and rheumatoid arthritis.

In one aspect, the EPAS1-related disease is cancer.

In one aspect, the method further comprises the step of administering an additional treatment.

In one aspect, the additional treatment is a method (or procedure). In one aspect, the additional treatment is a therapeutically effective dose of a composition.

In one aspect, the additional treatment and the RNAi agent can be administered in any order, or can be administered simultaneously.

In one aspect, the method further comprises the step of administering an additional treatment for cancer, metastases, astrocytoma, bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, non-small cell lung cancer, melanoma, multiple myeloma, ovarian cancer, rectal cancer, renal cancer, clear cell renal cell carcinoma (and metastases of this and other cancers), gingivitis, psoriasis, Kaposi's sarcoma-associated herpesvirus, preemclampsia, inflammation, chronic inflammation, neovascular diseases, and rheumatoid arthritis.

In one aspect, the method further comprises the step of administering an additional treatment. A RNAi agent to EPAS1 can be used in conjunction with any additional treatment disclosed herein, as appropriate for the disease, optionally, in further conjunction with one or more additional RNAi agents to EPAS1.

It will be understood that references to any additional treatment are meant to also include the pharmaceutically acceptable salts of any of the active substances. If active substances comprised by components (a) and/or (b) have, for example, at least one basic center, they can form acid addition salts. Corresponding acid addition salts can also be formed having, if desired, an additionally present basic center. Active substances having an acid group, e.g., COOH, can form salts with bases. The active substances comprised in components (a) and/or (b) or a pharmaceutically acceptable salts thereof may also be used in form of a hydrate or include other solvents used for crystallization.

In one aspect, the composition comprises a second RNAi agent to EPAS1. In various aspects, the second RNAi agent is physically distinct from the first, or the two are physically connected (e.g., linked or conjugated). In some aspects, the first and second RNAi agents are combined within the same composition (e.g., both in the same lipid nanoparticle).

A Method of Inhibiting the Expression of EPAS1, Using an RNAi Comprising an RNAi Agent Described Herein.

In one particular specific aspect, the present disclosure relates to a method of inhibiting the expression of EPAS1 in an individual, comprising the step of administering to the individual a therapeutically effective amount of a composition comprising an RNAi agent of the disclosure. In one aspect, the RNAi comprises a sense strand and an antisense strand, wherein the antisense strand comprises at least 15 contiguous nucleotides differing by 0, 1, 2, or 3 nucleotides from the antisense strand of an RNAi agent to EPAS1 selected from those specific duplexes provided above and as listed in Table 1.

In one aspect of the method, the RNAi agent comprises at least an anti-sense strand, and/or comprises a sense and an anti-sense strand, wherein the sequence of the sense and/or anti-sense strand is the sequence of the sense and/or the anti-sense strand of a RNAi agent to EPAS1 selected from those specific duplex provided herein and as listed, e.g., in Table 1, wherein the composition is in a pharmaceutically effective formulation.

In one aspect of the method, the RNAi agent comprises at least an anti-sense strand, and/or comprises a sense and an anti-sense strand, wherein the sequence of the sense and/or anti-sense strand comprises the sequence of the sense and/or the anti-sense strand of a RNAi agent to EPAS1 selected from those specific duplex provided herein and as listed, e.g., in Table 1, wherein the composition is in a pharmaceutically effective formulation.

Various particular specific aspects of this aspect are described below.

In one aspect, the individual is afflicted with or susceptible to an EPAS1-related disease.

In one aspect, the EPAS1-related disease is cancer, metastases, astrocytoma, bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, non-small cell lung cancer, melanoma, multiple myeloma, ovarian cancer, rectal cancer, renal cancer, clear cell renal cell carcinoma (and metastases of this and other cancers), gingivitis, psoriasis, Kaposi's sarcoma-associated herpesvirus, preemclampsia, inflammation, chronic inflammation, neovascular diseases, and rheumatoid arthritis.

In one aspect, the EPAS1-related disease is cancer.

In one aspect, the method further comprises the step of administering an additional treatment.

In one aspect, the additional treatment and the RNAi agent can be administered in any order or can be administered simultaneously.

In one aspect, the method further comprises the step of administering an additional treatment for cancer, metastases, astrocytoma, bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, non-small cell lung cancer, melanoma, multiple myeloma, ovarian cancer, rectal cancer, renal cancer, clear cell renal cell carcinoma (and metastases of this and other cancers), gingivitis, psoriasis, Kaposi's sarcoma-associated herpesvirus, preemclampsia, inflammation, chronic inflammation, neovascular diseases, and rheumatoid arthritis.

In one aspect, the composition comprises a second RNAi agent to EPAS1. In various aspects, the second RNAi agent is physically separate from the first, or the two are physically connected (e.g., covalently linked or otherwise conjugated). In some aspects, the first and second RNAi agents are combined within the same composition (e.g., both in the same lipid nanoparticle).

In one aspect, the method further comprises the step of administering an additional RNAi agent which comprises at least 15 contiguous nucleotides differing by 0, 1, 2, or 3 nucleotides from the antisense strand of a RNAi agent to EPAS1 selected from the specific duplexes provided herein and as listed, e.g., in any Table herein.

Pharmaceutical Compositions of a RNAi Agent to EPAS1

In one particular specific aspect, the present disclosure relates to a composition comprising a RNAi agent of the present disclosure. In one aspect, the RNAi agent comprises at least an anti-sense strand, and/or comprises a sense and an anti-sense strand, wherein the anti-sense strand comprises at least 15 contiguous nucleotides differing by 0, 1, 2, or 3 nucleotides from the anti-sense strand of a RNAi agent to EPAS1 selected from those specific duplex provided herein and as listed, e.g., in Table 1, wherein the composition is in a pharmaceutically effective formulation.

In one aspect, the RNAi agent comprises at least an anti-sense strand, and/or comprises a sense and an anti-sense strand, wherein the sequence of the sense and/or anti-sense strand is the sequence of the sense and/or the anti-sense strand of a RNAi agent to EPAS1 selected from those specific duplex provided herein and as listed, e.g., in Table 1, wherein the composition is in a pharmaceutically effective formulation.

In one aspect, the RNAi agent comprises at least an anti-sense strand, and/or comprises a sense and an anti-sense strand, wherein the sequence of the sense and/or anti-sense strand comprises the sequence of the sense and/or the anti-sense strand of a RNAi agent to EPAS1 selected from those specific duplex provided herein and as listed, e.g., in Table 1, wherein the composition is in a pharmaceutically effective formulation.

In one aspect, the present disclosure pertains to the use of a RNAi agent in the manufacture of a medicament for treatment of a EPAS1-related disease, wherein the RNAi agent comprises a sense strand and an antisense strand, wherein the antisense strand comprises at least 15 contiguous nucleotides differing by 0, 1, 2, or 3 nucleotides from the antisense strand of a RNAi agent to EPAS1 selected from those specific duplex provided herein and as listed, e.g., in any Table herein.

Specific Aspects of RNAi Agents to EPAS1 Comprising Mismatches from the Disclosed Sequences Various specific aspects of a RNAi agent to EPAS1 are disclosed herein. The present disclosure encompasses the example modified variants provided in Tables 1 to 5, and the corresponding unmodified sequences and other modified variants. Specific aspects of the present disclosure include RNAi agents which comprise sequences differing by 0, 1, 2, or 3 nt (nucleotides) or by [basepair(s)] (e.g., with 0, 1, 2 or 3 mismatches) from any of the RNAi agents listed in Table 1, and modified and unmodified variants thereof. As described in additional detail below, a mismatch is defined herein as a difference between the base sequence (e.g., A instead of G) or length when two sequences are maximally aligned and compared. In addition, as described in more detail below, an "unmodified variant" is a variant in which the base sequence is identical, but none of the bases are modified; this includes, for example, a sequence identical to the corresponding portion of the wild-type EPAS1 mRNA or gene. A "modified variant" contains one or more modifications (or one or more fewer or different modifications) to a nucleotide, sugar, phosphate or backbone, and/or addition of one or more moieties; but without a change, substitution, addition, or deletion to the base sequence. A particular sequence and its modified or unmodified variants have 0 mismatches among them.

In one particular aspect, the present disclosure comprises a RNAi agent comprising a sense and an anti-sense strand, wherein the sense and/or anti-sense strand comprises at least 15 contiguous nucleotides differing by 0, 1, 2, or 3 nt from the sequence of the sense and/or anti-sense strand of: any of the RNAi agents listed in Tables 1 to 5, and modified and unmodified variants thereof.

In another particular aspect, the RNAi agent comprises a sense strand comprising at least 15 contiguous nucleotides differing by 0, 1, 2, or 3 nt from the sense strand of any of the RNAi agents listed in Tables 1 to 5, and modified and unmodified variants thereof.

Other Aspects

Various particular specific aspects of this disclosure are described below. Any aspects disclosed herein that are not mutually exclusive can be combined.

In one aspect, the disclosure pertains to a composition according to any of the above aspects, for use in a method of treating a EPAS1-related disease in an individual, the method comprising the step of administering to the individual a therapeutically effective amount of a composition according to any of the claims.

Various particular specific aspects of this aspect are described below.

In one aspect, the disclosure pertains to the composition according to any of the above aspects, for use in a method of inhibiting the expression of EPAS1 in an individual, the method comprising the step of administering to the individual a therapeutically effective amount of a composition according to any of the above aspects.

One aspect of the disclosure is the use of a composition according to any of the above aspects, in the manufacture of a medicament for treatment of an EPAS1-related disease.

In one aspect, the EPAS1-related disease is selected from cancer, metastases, astrocytoma, bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, non-small cell lung cancer, melanoma, multiple myeloma, ovarian cancer, rectal cancer, renal cancer, clear cell renal cell carcinoma (and metastases of this and other cancers), gingivitis, psoriasis, Kaposi's sarcoma-associated herpesvirus, preemclampsia, inflammation, chronic inflammation, neovascular diseases, and rheumatoid arthritis.

In one aspect, the disclosure pertains to the composition of any of the above aspects, for use in the treatment of an EPAS1-related disease.

In one aspect, the EPAS1-related disease is cancer.

In one aspect, the disclosure relates to a method of inhibiting the expression of EPAS1 in an cell, comprising the step of introducing into the cell a composition comprising an RNAi agent comprising an antisense strand, wherein the antisense strand comprises at least 15 contiguous nucleotides differing by 0, 1, 2, or 3 nucleotides from the antisense strand of an RNAi agent to EPAS1 selected from the EPAS1 siRNAs disclosed herein.

In one aspect, the disclosure relates to a method of inhibiting the expression of EPAS1 in an cell, comprising the step of introducing into the cell a composition comprising an RNAi agent comprising a sense strand and an antisense strand, wherein the antisense strand comprises at least 15 contiguous nucleotides differing by 0, 1, 2, or 3 nucleotides from the antisense strand, and the sense strand comprises at least 15 contiguous nucleotides differing by 0, 1, 2, or 3 nucleotides from the sense strand of an RNAi agent to EPAS1 selected from the EPAS1 siRNAs disclosed herein.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

EPAS1

By "EPAS1" is meant the gene or protein also known as endothelial PAS domain protein 1, also known as EPAS-1, HIF-2 alpha; Hif2 alpha; HIF2; HLF; MOP2; ECYT4; HIF2A; PASD2; bHLHe73; HGNC: 3374; Gene ID: 2034. Note that some references label the gene HIF-2a, and the corresponding protein EPAS1 (for example, van Patot et al. 2011 High Alt. Med. Biol. 12: 157-167); other documents use the same term to refer to both the gene and protein. See: Ema et al. 1997 Proc. Natl. Acad. Sci. USA 94: 4273-4278; Flamme et al. 1997 Mech. Dev. 63: 51-60; and Hogenesch et al. 1997 J. Biol. Chem. 272: 8581-8593. Various polymorphisms of EPAS1 are known, as described in the literature, for example: van Patot et al. 2011 High Alt. Med. Biol. 12: 157-67; Ke et al. Zhonghua Yi Xue Yi Chuan Xue Za Zhi. 2011 October; 28(5):583-8; PMID: 21983741.

This gene encodes a transcription factor involved in the induction of genes regulated by oxygen, which is induced as oxygen levels fall.

EPAS1 is a member of the HIF family. Hypoxia-inducible factors (HIFs) are transcription factors that respond to changes in available oxygen in the cellular environment, specifically, to decreases in oxygen, or hypoxia. Smith et al. 2008 Br. J. Haematol. 141: 325-34.

Most, if not all, oxygen-breathing species express the highly-conserved transcriptional complex HIF-1, which is a heterodimer composed of an alpha and a beta subunit, the latter being a constitutively-expressed aryl hydrocarbon receptor nuclear translocator (ARNT). Wang et al. 1995 Proc. Natl. Acad. Sci. USA 92: 5510-14; Jiang et al. 1996 J. Biol. Chem. 271: 17771-8.

HIF family members include both Hif1 alpha and EPAS1 (Hif 2 alpha), the two best characterized HIF alpha subunits. While these two genes are highly similar and bind and mediate many of the same targets, they are different in function both temporally and spatially. While HIF1 alpha diminished the expression of interleukin-8 (IL-8), overexpression of EPAS1 increases expression of IL-8 (Florczyk et al. 2011 Free Radic. Biol. Med. 51: 1882-92).

EPAS1 (Hif2 alpha) encodes a half of a transcription factor involved in the induction of genes regulated by oxygen, which is induced as oxygen levels fall (hypoxia). The encoded protein contains a basic helix-loop-helix domain protein dimerization domain as well as a domain found in proteins in signal transduction pathways which respond to oxygen levels. EPAS1 is involved in the development of the embryonic heart and is expressed in the endothelial cells that line the walls of the blood vessels in the umbilical cord. It is essential in maintaining catecholamine homeostasis and protection against heart failure during early embryonic development. Catecholamines include proteins such as epinephrine and norepinephrine. It is important for the production of catecholamines to remain in homeostatic conditions so that both the delicate fetal heart and the adult heart do not overexert themselves and induce heart failure. Catecholamine production in the embryo is related to contol of cardiac output by increasing the fetal heart rate.

Mutations in this gene are associated with erythrocytosis familial type 4, pulmonary hypertension and chronic mountain sickness. There is also evidence that certain variants of this gene provide protection for people living at high altitude. EPAS1 is useful in high altitudes as a short term adaptive response. However, EPAS1 can also cause excessive production of red blood cells leading to chronic mountain sickness that can lead to death and inhibited reproductive abilities. Some mutations that increase its expression are associated with increased hypertension and stroke at low altitude, with symptoms similar to mountain sickness. People permanently living at high altitudes might experience selection of EPAS1 to reduce the fitness consequences of excessive red blood cell production.

EPAS1-related Diseases siRNAs to EPAS1 can be used to treat EPAS1-related diseases. An "EPAS1-related disease" is any disease associated with EPAS1 and/or a mutation and/or an over-expression of a wild-type and/or mutant EPAS1, and/or diseases wherein disease progression is enhanced by or prognosis worsened by the presence of EPAS1 and/or a mutation and/or an over-expression of wild-type and/or mutant EPAS1. Non-limiting examples of EPAS1-related diseases include: cancer, metastases, astrocytoma, bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, non-small cell lung cancer, melanoma, multiple myeloma, ovarian cancer, rectal cancer, renal cancer, clear cell renal cell carcinoma (and metastases of this and other cancers), gingivitis, psoriasis, Kaposi's sarcoma-associated herpesvirus, preemclampsia, inflammation, chronic inflammation, neovascular diseases, and rheumatoid arthritis. See: Bangoura et al. 2004 World J. Gastroenterol. 10: 525; Cleven et al. 2007 Analyt. Cell. Path. 29: 229-240; Covello et al. 2006 Genes Dev. 20: 557-570; Florczyk et al. 2011 Free Radic. Biol. Med. 51: 1882-92; Giatromanolaki et al. 2003 Melanoma Res. 13: 493-501; Giatromanolaki et al. 2006 App. Imm. Mol. Morph. 14: 78-82; Giatromanolaki et al. 2012 Clin. Exp. Metastasis 29: 11-7; Griffiths et al. 2008 Br. J. Cancer 98: 965-973; Guo et al. J. Kanazawa Med. U. 31: 10-16; Holmquist-Mengelbier et al. 2006 Cancer Cell 10: 413-23; Ioachim et al. 2006 Urol. Int. 77: 255-263; Koh et al. 2011 cancer Res. 71: 4015-4027; Maynard et al. 2007 Cell. Mol. Life Sci. 64: 2170-2180; Mutter et al. 2008 Microvasc. Res. 75: 1-8; Nesbit et al. 1999 Oncogene Mol. Cell 3: 565-577; Osada et al. 2007 Human Pathol. 38: 1310-1320; Pelegaris et al. 2002 Nat. Re. Cancer 2: 764-776; Rasheed et al. 2009 Br. J. Cancer 100: 1666-1673; Tian et al. 1998 Genes Dev. 12:3320-3324; Veeranna et al. 2012 J. Virol. 86: 1097-708; Xu et al. 2012 Oncogene 31: 1065-72;

HIF induction in normoxia is likely to have serious consequences in disease settings with a chronic inflammatory component. It has also been shown that chronic inflammation is self-perpetuating and that it distorts the microenvironment as a result of aberrantly active transcription factors. Consequently, alterations in growth factor, chemokine, cytokine and ROS balance occur within the cellular milieu that in turn provide the axis of growth and survival needed for de novo development of cancer and metastasis. The results of a recently published study have numerous implications for a number of pathologies where NF-κB and HIF-1 are deregulated, including rheumatoid arthritis and cancer. Therefore, it is thought that understanding the cross talk between these two key transcription factors, NF-κB and HIF, will greatly enhance the process of drug development.

HIF activity is involved in angiogenesis required for cancer tumor growth, so HIF inhibitors such as phenethyl isothiocyanate (PEITC) can be used for anti-cancer effects. At least part of the role of EPAS1 in tumor progression has been assigned to EPAS1-mediated upregulation of various genes. For example, EPAS1 plays an important role in the progression of uveal melanomas, possibly by promoting the autocrine loop VEGF-pVEGFR2/KDR, and by enhancing the expression of LDHA, thus conferring a growth advantage; see Giatromanolaki et al. 2012 Clin. Exp. Metastasis 29: 11-7.

EPAS1 is also involved in or upregulates expression of these factors: c-Myc (which favors cell proliferation, transformation, neoplasia and tumorigenesis, and which is highly expressed in most cancers; see Pelegaris et al. 2002 Nat. Re. Cancer 2: 764-776; Nesbit et al. 1999 Oncogene Mol. Cell 3: 565-577; Florczyk et al. 2011 Free Radic. Biol. Med. 51: 1882-92); Interleukin 8 (a proinflammatory mediator, e.g., in gingivitis and psoriasis; see Florczyk et al. 2011 Free Radic. Biol. Med. 51: 1882-92); SP-1 (a transcription factor involved in IL-8 regulation and a coactivator of c-Myc; see Florczyk et al. 2011 Free Radic. Biol. Med. 51: 1882-92); LDH5 (which is linked with tumor necrosis and increased tumor size; see Giatromanolaki et al. 2012 Clin. Exp. Metastasis 29: 11-7); and LANA (Latency Associated Nuclear Antigen, which is associated with Kaposi's sarcoma-associated Herpesvirus; see Veeranna et al. 2012 J. Virol. 86: 1097-708). In addition to collaborating with c-Myc, EPAS1 also collaborates with EGFR and KRAS; see, Holmquist-Mengelbier et al. 2006 Cancer Cell 10: 413-23; and Koh et al. 2011 Cancer Res. 71: 4015-4027. Thus, any disease related to over-expression and/or hyperactivity of c-Myc, EGFR and KRAS can be considered to be a EPAS1-related disease. In addition, HIF (hypoxia induced factor) activity is involved in angiogensis required for cancer tumor growth.

There is a rationale for targeting clear cell renal cell carcinoma (RCC) (ccRCC) and metastases thereof with EPAS1 RNAi agents. First, 90% of ccRCC cells do not express the VHL tumor suppressor. Second, in absence of VHL tumor suppressor Hif transcription factors are constitutively activated. Third, expression of Hif-2 is necessary and sufficient for RCC xenograft growth according to published studies. Constitutive Hif-2 shRNA knockdown blocks growth of 786-O cell xenografts. Inducible Hif-2 shRNA knockdown demonstrates that Hif-2 is necessary for 786-O xenograft maintenance. See also: Tian et al. 1998 Genes Dev. 12:3320-3324; Veeranna et al. 2012 J. Virol. 86: 1097-708; and Xu et al. 2012 Oncogene 31: 1065-72; Zimmer et al. 2004. Molecular Cancer Research 2:89-95; Kondo et al. 2002. Cancer Cell 1:237-246; and Kondo et al. 2003. PLoS Biology 1:439-444.

Thus, the present disclosure encompasses EPAS1 RNAi agents and the uses thereof for EPAS1-related diseases.

EPAS1 Gene Sequences in Various Species

The human EPAS1 gene has been sequenced. Ema et al. 1997 Proc. Natl. Acad. Sci. USA 94: 4273-4278; Flamme et al. 1997 Mech. Dev. 63: 51-60; and Hogenesch et al. 1997 J. Biol. Chem. 272: 8581-8593. Various polymorphisms of EPAS1 are known, as described in the literature, for example: van Patot et al. 2011 High Alt. Med. Biol. 12: 157-67; Ke et al. Zhonghua Yi Xue Yi Chuan Xue Za Zhi. 2011 October; 28(5):583-8; PMID: 21983741.

The Cynomolgus monkey ("Cyno", or *Macaca fascicularis*) EPAS1 sequence (SEQ ID NO: 125) is presented below:

```
cyno_kidney_NM_001430 EPAS1, endothelial
PAS domain protein 1 consensus -- target length =
5186, consensus length = 4636, 9 contigs (longest
is 2117) 104 mismatches, 1352 reads, coverage:
max = 84, mean = 18.499; consensus
consistency = 99.31%, target/consensus
conservation 97.76%
                                    (SEQ ID NO: 125)
NNNNNNNNNNNNNNNNNNNNNNNNNNNNNNNNNNNNNNNNNNNNNNNNNN

NNNNNNNNNNNNCTCGGCAGTcTCCTGAGACTGTATGGTCAGCTCAGCCC

AGCCTCCGACTCCTTCCGACTCCCAGCATTCGAGCCACTTTTTTTTTTCC

TTGAAAACTCAGAAAAGTGACTCTTTTTCCAGGGAAAAAGGAACTTGGGT

TCCCTTCTCGCCGTCCTTTTTTTCGGGTCTGACAGCCTCCACCCACTCCTT

CCCCNNNNNNNNNNNNNNNNNNNNNNNNNNNNNNCGTCACCTTTCTCCAC

CCCCACCCCCGCACCTAGCCCGCCGCGCGCCACCTTCCACCTGACTGCGC

GGGGCGCTCGGGACCTGCGCGCACCTCGGACCTTCACCACCCGCCCcGGC

CGCCGGGAGCGGACGAGGGCCACAGCTCCCCACCCGCCGGGAAGCCCAGG

TGCTCGGCGTCTGAACGTCTCAAAGGGCCACAGCGACAATGACAGCTGAC
```

-continued

AAGGAGAAGAAAAGGAGTAGCTCGGAGAGGAGGAAGGAGAAGTCCCGGGA

TGCCGCACGGTGCCGGCGGAGCAAGGAGACGGAGGTGTTCTACGAGCTGG

CCCATGAGCTGCCTCTGCCCCACAGCGTGAGCTCCCATCTGGACAAGGCC

TCCATCATGCGACTGGCGATCAGCTTCCTGCGAACACACAAGCTCCTCTC

CTCAGTTTGCTCTGAAAATGAGTCTGAAGCTGAAGCTGACCAGCAGATGG

ACAACTTGTACCTGAAAGCCTTGGAGGGTTTCATTGCCGTGGTGACCCAA

GATGGCGACATGATCTTTCTGTCAGAAAACATCAGCAAGTTCATGGGACT

TACACAGGTGGAGCTAACAGGACATAGTATCTTTGACTTCACTCATCCCT

GCGACCACGAGGAGATTCGTGAGAACCTGAGTCTCAAAAATGGCTCTGGT

TTTGGGAAAAAAAGCAAAGACATGTCCACAGAGCGGGACTTCTTCATGAG

GATGAAGTGCACGGTCACCAACAGAGGCCGTACTGTCAACCTCAAGTCAG

CCACCTGGAAGGTCTTGCACTGCACGGGCCAAGTGAAAGTCTACAACAAC

TGCCCTCCTCACAATAGTCTGTGTGGCTACAAGGAGCCCCTGCTGTCCTG

CCTCATCATCATGTGTGAACCGATCCAGCACCCATCCCACATGGACATTC

CCCTGGACAGCAAGACCTTCCTGAGCCGCCACAGCATGGACATGAAGTTC

ACCTACTGTGATGACAGAATCACAGAACTGATTGGTTACCACCCTGAGGA

GCTGCTTGGCCGCTCAGCCTATGAATTCTACCATGCGCTAGACTCCGAGA

ACATGACCAAGAGTCACCAGAACTTGTGCACCAAGGGCCAGGTGGTAAGT

GGCCAGTACCGGATGCTCGCAAAGCATGGGGGCTACGTGTGGCTGGAAAC

CCAGGGGACAGTCATCTACAACCCTCGCAACCTGCAGCCCCAGTGCATCA

TGTGTGTCAACTACGTTCTGAGTGAGATTGAGAAGAATGACGTGGTGTTC

TCCATGGACCAGACGGAATCCCTGTTCAAGCCCCACCTGATGGCCATGAA

CGGCATCTTTGATAGCAGTGGCAAGGGGGCTGTGTCTGAGAAGAGTAACT

TCCTATTCACCAAGCTAAAGGAGGAGCCTGAGGAGCTGGCCCAGCTGGCT

CCCACCCCAGGAGACGCCATCATCTCTCTGGATTTCGGGAATCAGAACTT

CGAGGAATCCTCAGCCTATGGCAAGGCCATCCTGCCCCCGAGCCAGCCGT

GGGCCACAGAGTTGAGGAGCCACAGCACCCAGAGCGAGGCTGGGAGCCTG

CCTGCCTTCACCGTGCCCCAGGCAGCCGCCCCGGGCAGCACCACCCCCAG

TGCCACCAGCAGCAGCAGCAGCTGCTCCACGCCCAATAGCCCTGAAGACT

ATTATACATCTTTGGATAACGACCTGAAGATTGAAGTGATTGAGAAGCTC

TTCGCCATGGACACAGAGGCCAAGGACCAATGCAGTACCCAGACGGATTT

CAATGAGCTGGACTTGGAGACACTGGCACCCTATATTCCCATGGATGGGG

AAGACTTCCAGCTGAGCCCCATCTGCCCCGAGGAGCGGCTCTTGGCGGAG

AACCCACAGTCCACCCCCCAGCACTGCTTCAGTGCCATGACAAACATCTT

CCAGCCACTGGCCCCTGTAGCCCCGCACAGTCCCTTCCTCCTGGACAAGT

TTCAGCAGCAGCTGGAGAGCAAGAAGACAGAGCCCGAGCACCGGCCCATG

TCCTCCATCTTCTTTGATGCCGGAAGCAAAGCATCCCTGCCACCATGCTG

TGGCCAGGCCAGCACCCCTCTCTCTTCCATGGGGGGCAGATCCAATACCC

ANTGGCCCCCAGATCCACCATTACATTTTGGGCCCACAAAGTGGGCCGTC

GGGGATCAGCGCACAGAGTTCCTGGGAGCGNNNNNNNNNNNNNNNNNNNN

NNNNNNNNCCCATATCTCCACATTCAAGACAAGGTCTGCAAAGGGTTTTG

-continued

GGGCTCGAGGCCCAGACGTGCTGAGCCCGGCCATGGTAGCCCTCTCCAAC

AAGCTGAAGCTGAAGCGACAGCTGGAGTATGAAGAGCAAGCCTTCCAGGA

CCTGAGTGGGGGGGACCCACCTGGTGGCAGCACTTCACATTTGATGTGGA

AACGGATGAAGAACCTCAGGGGTGGGAGCTGCCCTTTGATGCCGGACAAG

CCACTGAGCGCAAATGTCCCCAATGGTAAGTTCACCCAAAATCCTGTGAG

GGGCCTGGGCCATCCCCTGAGACATCTGCCGCTGCCACAGCCTCCATCTG

CCGTCAGTCCCGGGGAGAACAGCAAGAGCAGGTTCCCCGCACAGTGCTAT

GCCACcCAGTACCAGGACTACAGCCTGTCGTCAGCCCACAAGGTGTCAGG

CATGGCAAGCCGGCTGCTCGGGCCCTCGTTTGAGTCCTACCTGCTGCCTG

AACTGACCAGATATGACTGTGAGGTGAACGTGCCCGTGCTGGGAAGCTCC

ACGCTCCTGCAAGGAGGGGACCTCCTCAGAGCCCTGGACCAGGCCACCTG

AGCCAGGCCTTCCACCTGGGCAGCACCTCTGCCGACACCGTCCCACCAGC

TTCACTCTCTCCATCTGTTTTTGTAACTAGGTATTTCTAACACCAGCACA

CTATTTACAAGATGGACTTACCTGGCAGACTTGCCCAGGTCACCACGCAG

TGGCCTTTTTCTGAGATGCTCACTTTATTATCCCTATTTTTAAAGTACAC

AATTGTTTTACCTGTTCTGAAATGTTCTTAAATTTTGTAATATTTTTTTT

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNGCGTTAGCTTCATTTTACTAAAAAGATT

CCTCGTTACTGTTGTTGCCAAAGAGAAACAAAAATGATGTTGCNNNNNNN

NNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNN

NNNNNNNNNNNNNNNNNNNNNNAAAAAAGAAATGTGAAGGGTCAACTCCA

ACGTATGTGGTTATCTGTGAAGGCTGCATAGCGTGGCTTTTCCTAAACTG

GTGTTTTTCCCCCGCATTCGGTGGATTTTTTATTATTATTCAAAAACATA

ACTGAGTTTTTNNNNNNNNNAGAAAATTTATATCTGGGTTAAGTGTTTAT

CATATATATGGGTACTCTGTAATATCTAAAACCTTAGAAACGGAAATGGA

ATCCTGCTCACAAAATCACTTTAAGATCTTTTCAAAGCTGTTAATTTTTC

TTGGTGTTGTGGACACTGCAGACTTGTCCAGTGCTCCCACAGCCTGTACG

GACACTGTGGAAGGCCTCCCTCTGTCGGCTTTTTGCCATCTGTGATATGC

CATAGGTGTGACAATCCGAGCAGTGGAGTCATTCAGTGGGAGCACTGCGC

GCTATCCCCTCATGTTCTCTATGTACTATGTATGTATGTATTATTATTAT

TGCTGCCAAGAGGGTCTGATGGCACGTTGTGGGGTCGGGGGGTGGGGCGG

GGAAGTGCTCTAACTTTTCTTAAGGTTTTGTTGCTAGCCCTTCAAGTGCA

CTGAGCTATGTGACTCGGATGGTCTTTCACACGGCACATTTAGACATTTC

CAGAACTACCATGAGATGGTTTAGATGGGAATTCATGCAAATGAGGGGTC

AGAAATGGTATAGTGACCCGGTCCACGTCCTCCAAGCTCACGACCTTGGA

GCCCCGTGGAGCTGGACTGAGGAGGAGGCTGCACAGCGGGAGAGCAGCTG

GTCCAGACCAGCCTTGCAGNNNNNNNNNNNNNNNNNNNNNNNNNNNNNNN

NNNNNNNNNNNNNNNNNNNNNNNNNNNNNNNNNNNNNNNNNNNNNNNNNN

-continued

```
NNNNNNNNNNNNNNNNNNNNNNNNNAAGCACTGAAAATAGCGTTCCCAGA

GCACATTGCAACTCACTGGGTAAGAGGGACGACACCTCTGGTTTTTCAAT

ACCAATTACATGGAACTTTTCTGTAATGGGTACAACGAAGAAGTTTCTAA

AAACACACACAAAGCACATTAGGCCAACTATTTAGTAAGCCCGGATGGAC

TTATTGCCAGAAACAAAAAGTAGCTTTCAAAAGAAATTTAAGTTATATGA

GAAATTCCTTAGTCATGGTGTTGTCTAAATCATATTTTAGCTGCACGNNN

NNNNNNNNNNNNNNNAGGCAGAACTTGAAGGGTTACTGACATGTAAATGC

TGGTATTTGATTTCCTGTGTGTGTTGCCCTGGCATTAAGGGCATTTTACC

CTTGCAGTTTTACTAAAACACTGAAAAATATTCCAAGCTTCATATTAACC

CTACCTGTCAACGTAACGATTTCATGAACATTATTATATTGTCGAATTCC

TACTGACAACATTATAACTGTATGGGAGCTTAACTTTATAAGGAAATGTA

TTTTGACACTGGTATCTTATTAAAGTATTCTGATCCTAAAANNNNNNNNN

NNNNNNNNNNNNNNNNNNNNNNNNNNNNNNNNNNNN
```

N indicates that the nucleotide was not determined at that position in the sequencing experiment.

In one aspect, the EPAS1 RNAi agent of the present disclosure comprises a sequence which is identical in the human, mouse and cyno EPAS1 gene. This sequence identity facilitates animal testing prior to human testing.

In one aspect, the EPAS1 RNAi agent comprises a sequence which does not match that of any other gene. In one aspect, the EPAS1 RNAi agent comprises a sequence which differs from all other known non-EPAS1 genes by at least 0, 1, 2 or 3 nucleotides.

In one aspect, the EPAS1 RNAi agent comprises a sequence which is identical to that of any RNAi agent disclosed herein.

EPAS1 RNAi Agent for Use in Treating Various EPAS1-related Diseases

In one aspect, the EPAS1 RNAi agent of the present disclosure comprises a sequence disclosed herein and is administered to a patient in need thereof (e.g., a patient suffering from an EPAS1-related disease disclosed herein or known in the literature). In one aspect, the EPAS1 RNAi agent of the present disclosure is administered to a patient in need thereof, along with one or more additional pharmaceutical agent appropriate for that disease. For example, a patient suffering from an EPAS1-related disease can be administered a pharmacologically effective amount of one or more EPAS1 RNAi agent along with a pharmacologically effective amount of one or more of any EPAS1-related disease treatment listed herein, and/or any other EPAS1-related disease treatment known in the art.

A patient suffering from a EPAS1-related disease can be administered one or more RNAi agent to EPAS1 and one or more additional EPAS1-related disease treatment. This additional treatment can be selected from the list of any disease treatment listed herein, and/or any anti-EPAS1-related disease treatment known in the art.

The patient can also be administered more than one RNAi agent to EPAS1.

In the case of EPAS1-related diseases, the RNAi agent(s) and additional disease treatment(s) can be administered in any order, simultaneously or sequentially, or in multiple doses over time. Administration of the RNAi agent and the additional treatment can be, for example, simultaneous, concurrent, separate or sequential.

Simultaneous administration may, e.g., take place in the form of one fixed combination with two or more active ingredients, or by simultaneously administering two or more active ingredients that are formulated independently. Sequential use (administration) preferably means administration of one (or more) components of a combination at one time point, other components at a different time point, that is, in a chronically staggered manner, preferably such that the combination shows more efficiency than the single compounds administered independently (especially showing synergism). Separate use (administration) preferably means administration of the components of the combination independently of each other at different time points, preferably meaning that the components (a) and (b) are administered such that no overlap of measurable blood levels of both compounds are present in an overlapping manner (at the same time).

Also combinations of two or more of sequential, separate and simultaneous administration are possible, preferably such that the combination component-drugs show a joint therapeutic effect that exceeds the effect found when the combination component-drugs are used independently at time intervals so large that no mutual effect on their therapeutic efficiency can be found, a synergistic effect being especially preferred.

The term "delay of progression" as used herein means administration of the combination to patients being in a pre-stage or in an early phase, of the first manifestation or a relapse of the disease to be treated, in which patients, e.g., a pre-form of the corresponding disease is diagnosed or which patients are in a condition, e.g., during a medical treatment or a condition resulting from an accident, under which it is likely that a corresponding disease will develop.

"Jointly therapeutically active" or "joint therapeutic effect" means that the compounds may be given separately (in a chronically staggered manner, especially a sequence-specific manner) in such time intervals that they preferably, in the warm-blooded animal, especially human, to be treated, still show a (preferably synergistic) interaction (joint therapeutic effect). Whether this is the case, can inter alia be determined by following the blood levels, showing that both compounds are present in the blood of the human to be treated at least during certain time intervals.

Additional Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

As used throughout this disclosure, articles such as "a" and "an" refer to one or more than one (at least one) of the grammatical object of the article.

RNAi Agent

In one aspect, the present disclosure pertains to a EPAS1 RNAi agent or other composition comprising at least an antisense nucleic acid sequence complementary to a EPAS1 nucleic acid (or portion thereof), or pertains to a recombinant expression vector encoding an shRNA or composition comprising the antisense nucleic acid that can function as an RNAi as defined below. As used herein, an "antisense" nucleic acid comprises a nucleotide sequence complementary to a "sense" nucleic acid encoding the EPAS1 protein (e.g., complementary to the coding strand of a double-stranded DNA, complementary to an mRNA or complementary to the coding strand of a EPAS1 gene or nucleic acid).

RNAi agents include, as non-limiting examples, siRNAs (small interfering RNAs), dsRNAs (double stranded RNAs), shRNAs (short hairpin RNAs) and miRNAs (micro RNAs). RNAi agents also include, as additional non-limiting examples, locked nucleic acid (LNA), Morpholino, UNA, threose nucleic acid (TNA), or glycol nucleic acid (GNA), peptide nucleic acid (PNA) and FANA. RNAi agents also include molecules in which one or more strands are a mixture of RNA, DNA, LNA, Morpholino, UNA (unlocked nucleic acid), TNA, GNA, and/or FANA, etc. As a non-limiting example, one or both strands of an RNAi agent could be, for example, RNA, except that one or more RNA nucleotides is replaced by DNA, LNA, Morpholino, UNA (unlocked nucleic acid), TNA, GNA, and/or FANA, etc. In various aspects, one or both strands of the RNAi agent can be nicked, and both strands can be the same length, or one (e.g., the passenger strand), can be shorter than the other.

In various aspects, the present disclosure pertains to any RNAi agent comprising a RNA sequence disclosed herein and/or a RNA sequence corresponding to any DNA sequence disclosed herein (e.g., wherein the DNA nucleotides are replaced by the corresponding RNA nucleotide, for example, with T in DNA replaced by U in RNA, and with ribose instead of deoxyribose in the sugar-phosphate backbone).

The RNAi agent(s) of the present disclosure target (e.g., bind to, anneal to, hybridize, etc.) the EPAS1 mRNA. The use of the RNAi agent specific to EPAS1 results in a decrease of EPAS1 activity, level and/or expression, e.g., a "knock-down" (KD) or "knock-out" of the target gene or target sequence. In one aspect, in the case of a disease state characterized by over-expression or hyper-activity of EPAS1, administration of a RNAi agent to EPAS1 knocks down the EPAS1 target enough to provide a more normal or therapeutic level of EPAS1 activity or expression. EPAS1 −/− mice showed multiple organ pathology, biochemical abnormalities and altered gene expression; see Scortegagna et al. Nat. Genet. 35: 331-340. Thus, a minimal expression of EPAS1 in normal tissues can be beneficial. In various aspects of the disclosure, the patient or individual may have a disease state characterized by excessively high levels of EPAS1 and the RNAi agent can restore a normal level. In one aspect of the disclosure, the levels of EPAS1 throughout the body are modulated such that EPAS1 levels in one area (e.g., areas afflicted by a EPAS1-related disease) are lower, while areas of the body not afflicted by the disease are closer to normal EPAS1 levels. In one aspect of the disclosure, the RNAi agent can be delivered locally (e.g., to the site of the disease, such as a tumor) so that levels of EPAS1 outside the diseased areas can be maintained as close to normal as possible. In another aspect, the level of EPAS1 in the body can be modulated such that it is low enough to improve the disease state (e.g., low enough to discourage tumor growth), but not so low that organ pathology occurs.

In one aspect, the RNAi comprises a single strand. This single-stranded RNAi agent oligonucleotide or polynucleotide can comprise the sense or antisense strand, as described by Sioud 2005 J. Mol. Biol. 348:1079-1090, and references therein. Thus the disclosure encompasses RNAi agents with a single strand comprising either the sense or antisense strand of an RNAi agent described herein. The disclosure also encompasses RNAi agents comprising a single strand, wherein the single strand comprises the sequences of both the antisense and sense strands of any RNAi agent disclosed herein, e.g., wherein the strands are contiguous, connected by a loop or otherwise linked. Examples of such molecules include those with a hairpin between the sense and anti-sense sequences (e.g., shRNA).

In various aspects, one or both strands contain one or more nicks, i.e., a break or missing bond in the phosphate backbone, such that at least one nucleotide subunit is not covalently linked to the adjacent nucleotide subunit in any given sequence. In some aspects, the passenger strand is nicked (see, for example, WO 2007/107162). In various aspects, one or both strands contain one or more gaps, e.g., wherein at least one entire nucleotide subunit is absent from the disclosed sequence. Where a sense or antisense sequence contains a gap, that strand is envisioned to comprise two separate oligonucleotides.

Particularly useful siRNAs include those which can bind specifically to those regions of the EPAS1 mRNA that have one or more of the following qualities: binding in the coding segment of EPAS1; binding at or near the junction of the 5' untranslated region and the start of the coding segment; binding at or near the translational start site of the mRNA; binding at, across or near junctions of exons and introns; little or no binding to the mRNAs or transcripts of other genes (little or no "off-target effects"); binding to the EPAS1 mRNA in or near a region or regions that is not double-stranded or a stem region, e.g., those in a loop or single-stranded portion; eliciting little or no immunogenicity; binding in a segment of the EPAS1 mRNA sequence which is conserved among various animal species (including human, mouse, rat, cyno, etc.), as the presence of a conserved sequence facilitates testing using various laboratory animals; binding to double-stranded region(s) of the mRNA; binding to an AT-rich region (e.g., at least about 50, 51, 52, 53, 54, 55, 56, 57, 58, 59, or 60% AT-rich); and/or lacking particular sequences known or suspected to decrease siRNA activity, e.g., the presence of a GG sequence at the 5'end, which may decrease separation of the double-stranded portion of the siRNA. In one aspect, the RNAi agent specific to EPAS1 can be a double-stranded RNA having any one or more of these qualities.

The term "double-stranded RNA" or "dsRNA," as used herein, refers to a RNAi agent comprising a first and a second strand; e.g., a composition that includes an RNA molecule or complex of molecules having a hybridized duplex region (i.e., a region where the nucleotide bases from the first strand and the second strand are paired) that comprises two anti-parallel and substantially complementary nucleic acid strands, which will be referred to as having "sense"and "antisense" orientations with respect to a target RNA. The antisense strand, with respect to the mRNA target, is also called the "guide" strand, and the sense strand is also called the "passenger" or "anti-guide" strand. The passenger strand can include at least one or more of the following: one or more extra nucleotides (e.g., a bulge or 1 nt loop) compared to the other strand, and/or a nick, a gap, a mismatch, etc., compared to the other strand. In various aspects, the RNAi agent comprises a first strand and a second strand. In various aspects, and as used herein and as is clear by context, terminology referring to the first strand refers to the sense strand and the second strand refers to the anti-sense strand as listed in any Table herein. In other aspects, and as used herein and as is clear by context, the first strand refers to the anti-sense strand, and the second strand refers to the sense strand as listed in any Table herein.

The duplex region can be of any length that permits specific degradation of a desired target RNA through a RISC pathway, but will typically range from 9 to 36 base pairs ("bp") in length, e.g., 15-30 bp in length. Considering a duplex between 9 and 36 bp, the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 bp and any sub-range therebetween, including, but not limited to 15-30 bp, 15-26 bp, 15-23 bp, 15-22 bp, 15-21 bp, 15-20 bp, 15-19 bp, 15-18 bp, 15-17 bp, 18-30 bp, 18-26 bp, 18-23 bp, 18-22 bp, 18-21 bp, 18-20 bp, 19-30 bp, 19-26 bp, 19-23 bp, 19-22 bp, 19-21 bp, 19-20 bp, 19 bp, 20-30 bp, 20-26 bp, 20-25 bp, 20-24 bp, 20-23 bp, 20-22 bp, 20-21 bp, 20 basepairs, 21-30 bp, 21-26 bp, 21-25 bp, 21-24 bp, 21-23 bp, 21-22 bp, 21 bp, 22 bp, or 23 bp. The dsRNAs generated in the cell by processing with Dicer and similar enzymes are generally in the range of about 19 to about 22 bp in length, though the strands of artificial dsRNAs can be shorter or longer. siRNAs wherein one or both strands are as short as 16 or 15 nt still demonstrate RNA interference activity. Chu and Rana 2008 RNA 14: 1714-1719. One strand of the duplex region of a dsRNA comprises a sequence that is substantially complementary to a region of a target RNA. The two strands forming the duplex structure can be from a single RNA molecule having at least one self-complementary duplex region, or can be formed from two or more separate RNA molecules that hybridize to form the duplex. Where the duplex region is formed from two self-complementary regions of a single molecule, the molecule can have a duplex region separated by a single-stranded chain of nucleotides (herein referred to as a "hairpin loop", e.g., such as found in an shRNA construct) between the 3'-end of one strand and the 5'-end of the respective other strand forming the duplex structure. The hairpin loop can comprise at least one unpaired nucleotide; in some aspects the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are comprised by separate RNA molecules, those molecules need not, but can, be covalently connected. Where the two strands are connected covalently by a hairpin loop, the construct is generally referred to herein and in the art as a "shRNA". Where the two strands are connected covalently by means other than a hairpin loop, the connecting structure is referred to as a "linker."

RNAi Agents to EPAS1 Comprising Mismatches from the Disclosed Sequences

Various specific aspects of a RNAi agent to EPAS1 are disclosed herein; example sequences are provided in the Tables. Specific aspects of the present disclosure include RNAi agents which comprise sequences differing by 0, 1, 2, or 3 nt (nucleotides) or by [basepair(s)](e.g., with 0, 1, 2 or 3 mismatches) from any of the RNAi agents listed in Tables 1 to 5, and modified and unmodified variants thereof.

A mismatch is defined herein as a difference between the base sequence or length when two sequences are maximally aligned and compared. A mismatch is defined as a position wherein the base of one sequence does not match the base of the other sequence. Thus, a mismatch is counted, for example, if a position in one sequence has a particular base (e.g., A), and the corresponding position on the other sequence has a different base (e.g., G). Substitution of A, for example, with T, C, G or U would constitute a mismatch. Substitution of G with T, A, C or U would also constitute a mismatch. Substitution of C with T, G, A or U would also constitute a mismatch. Substitution of U with A, C or G would constitute a mismatch. Note, however, that on a given strand, a U can be replaced by T (either as RNA or, preferably, DNA, e.g., 2'-deoxy-thymidine); the replacement of a U with a T is not a mismatch as used herein, as either U or T can pair with A on the opposite strand. The RNAi agent can thus comprise one or more DNA bases, e.g., T. In some cases, in a portion or portions of the RNAi agent, DNA can be used in place of RNA (e.g., in the seed region), to form a DNA-RNA hybrid. See, for example, Yamato et al. 2011 cancer Gene Ther. 18: 587-597. No mismatch is counted between a DNA portion(s) of the RNAi agent and the corresponding target mRNA if basepairing occurs (e.g., between A, G, C, or T in the DNA portion, and the corresponding U, C, G, or A, respectively in the mRNA).

A mismatch is also counted, e.g., if a position in one sequence has a base (e.g., A), and the corresponding position on the other sequence has no base (e.g., that position is an abasic nucleotide, which comprises a phosphate-sugar backbone but no base). A single-stranded nick in either sequence (or in the sense or anti-sense strand) is not counted as mismatch. Thus, as a non-limiting example, no mismatch would be counted if one sequence comprises the sequence AG, but the other sequence comprises the sequence AG with a single-stranded nick between the A and the G. A nucleotide modification in the sugar or phosphate is also not considered a mismatch. Thus, if one sequence comprises a C, and the other sequence comprises a modified C (e.g., 2'-modification) at the same position, no mismatch would be counted.

Thus, no mismatches are counted if modifications are made to the sugar, phosphate, or backbone of the RNAi agent without modifying the base. Thus, a strand having the sequence of AUGGCGACAUGAUCUUUCU (SEQ ID NO: 1) as an RNA would have zero mismatches from another strand having the same sequence as a PNA; or morpholino; or LNA; or TNA; or GNA; or FANA; or a mix or chimera of RNA and DNA, TNA, GNA, FANA, Morpholino, UNA, LNA, and/or PNA, etc.

It is also noted that the sequences of the RNAi agents in the Tables include sequences which comprise modifications, as detailed in Table 5. It is noted that dTdT (2'-deoxy-thymidine-5'-phosphate and 2'-deoxy-thymidine-5'-phosphate), or in some cases, TT or UU, can be added as a terminal dinucleotide cap or extension to one or both 3'-ends, but this cap or extension is not included in the calculation of the total number of mismatches and is not considered part of the target sequence. This is because the terminal dinucleotide protects the ends from nuclease degradation but does not contribute to target specificity (Elbashir et al. 2001 Nature 411: 494-498; Elbashir et al. 2001 EMBO J. 20: 6877-6888; and Kraynack et al. 2006 RNA 12:163-176).

In addition, as in Table 5, a modified variant can have one or more modifications from the corresponding unmodified sequence. In this case, lowercase "c" represents 2'-O-methylcytidine-5'-phosphate, and lowercase "u" represents 2'-O-methyluridine-5'-phosphate. Uppercase "A", "C", "G" and "U" represent the un-modified adenosine-5'-phosphate, cytidine-5'-phosphate, guanosine-5'-phosphate, and uridine-5'-phosphate, respectively. Various modifications are shown in FIG. 1. The substitution, for example, r of modified c for unmodified C does not count as a mismatch in numbering the 0, 1, 2, or 3 mismatches between sequences. This nomenclature is used for all sequences in Tables 1 to 6. Thus, an equal number of mismatches would be calculated (a) between a test sequence and that of another RNAi agent, and (b) between the same test sequence and the corresponding unmodified sequence from the EPAS1 gene, and (c) between a modified sequence and a differently modified sequence which have the same base sequence.

In one particular aspect, the present disclosure comprises a RNAi agent comprising a anti-sense strand comprising at least 15 to 19 contiguous nucleotides differing by 0, 1, 2, or 3 nt from the sequence of the anti-sense strand of: any of the RNAi agents listed in Tables 1 to 6, and modified and unmodified variants thereof.

The present disclosure pertains to "modified and unmodified variants" of the disclosed sequences.

An "unmodified variant" of a particular sequence is the corresponding portion of EPAS1 without any modifications. Example modified sequences are listed in Table 3. The "unmodified variants" of the sequences of the Tables have the identical sequence, without base modifications or terminal dTdT. A given sequence and an "unmodified variant" of it differ by 0 nt (and have no mismatches).

A "modified variant" of a particular sequence comprises one or more (or one or more fewer) modifications to the backbone, sugar, phosphate or base, and/or addition of a terminal dinucleotide (e.g., TT, dTdT, TsT or UU), but do not have any base substitutions (e.g., G for C, or A for G); thus a given sequence and a modified variant thereof differ by 0 nt (and have no mismatches). As another example, a given sequence as a RNA and the same sequence as a PNA are modified variants of each other and differ by 0 nt (and have no mismatches). Similarly, the same sequence (with no base substitutions) as a locked nucleic acid (LNA), Morpholino, UNA (unlocked nucleic acid), threose nucleic acid (TNA), or glycol nucleic acid (GNA) would be a modified variant which has 0 mismatches. In addition, the same sequence could be used in strands which are a mixture of RNA, DNA, LNA, Morpholino, TNA, GNA, and/or FANA, etc. As a non-limiting example, one or both strands could be, for example, RNA except that one or more nucleotides is replaced by DNA, LNA, Morpholino, UNA, TNA, GNA, and/or FANA, etc.

As detailed below, substituting a single nucleotide at a given position with a modified version of the same nucleotide would produce a modified variant (with 0 mismatches).

In another particular aspect, the RNAi agent comprises a sense strand comprising at least 15 contiguous nucleotides differing by 0, 1, 2, or 3 nt from the sense strand of any of the RNAi agents listed in the Tables and modified and unmodified variants thereof.

RNAi agents to EPAS1 of the present disclosure can be used in RNA interference.

Modifications of RNAi Agents

The present disclosure encompasses both unmodified and example modified RNAi agents, such as those disclosed in the Tables.

The present disclosure further encompasses any other modification of a disclosed RNAi agent (e.g., a modified variant).

For example, the disclosure encompasses a RNAi agent with a substitution of a single nucleotide at a given position with a modified version of the same nucleotide. Thus a nucleotide (A, G, C or U) can be replaced by the corresponding 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, or 2,6-diaminopurine.

Additional modified variants include the addition of any other moiety (e.g., a radiolabel or other tag or conjugate) to the RNAi agent; provided that the base sequence is identical, the addition of other moieties produces a "modified variant" (with no mismatches).

Various sets of modifications can be used. These include the following formats, which are used in various screens disclosed herein.

Two such sets of modifications include A51 S26 and A85S26; EPAS1 RNAi agents with these modification sets are presented in Table 5.

A51S53

Guide strand: All U and C except positions 1, 2 and 14 are 2'-OMe

Sense strand: All U as 2'-OMe-U.

A85S26 ("NEW")

Guide strand: All U except position 1, 2 and 14 are 2'-OMe

Sense strand: All C and U are modified (2'-OMe)

However, other modifications of the EPAS1 RNAi agent sequences disclosed herein could be prepared. These include, as non-limiting examples:

A51 S26

A51: In guide strand all U as 2'-OMe-U and all C as 2'-OMe-C, except pos. 1, 2 and 14; 3'overhangs as 2'-OMe-U 2'-OMe-U S26: In sense strand all U as 2'-OMe-U and all C as 2'-OMe-C; 3' overhangs as 2'-OMe-U 2'-OMe-U

A22S26

A22 indicates that All UA as 2'-OMe-U A and all CA as 2'-OMe-C A

S26 indicates that All U as 2'-OMe-U and all C as 2'-OMe-C

All 3' overhangs as 2'-OMe-U 2'-OMe-U

In addition to these modifications and patterns (e.g., formats) for modifications, other modifications or sets of modifications of the sequences provided can be generated using common knowledge of nucleic acid modification. These various aspects of the RNAi agents to EPAS1 of the present disclosure can be used in RNA interference.

RNA Interference

RNA interference (RNAi) is a post-transcriptional, targeted gene-silencing technique that uses double-stranded RNA (dsRNA) to degrade messenger RNA (mRNA) containing the same sequence as the dsRNA. The process of RNAi occurs when ribonuclease III (Dicer) cleaves the longer dsRNA into shorter fragments called siRNAs. siRNAs (small interfering RNAs) produced by Dicer are typically about 21 to 23 nucleotides long and comprise about 19 base pair duplexes (though artificial siRNAs or RNAi agents can be shorter or longer, and/or blunt-ended, and/or comprises one or more endcaps). The smaller RNA segments then mediate the degradation of the target mRNA. Dicer has also been implicated in the excision of 21- and 22-nucleotide small temporal RNAs (stRNAs) from precursor RNA of conserved structure that are implicated in translational control. Hutvagner et al. 2001 Science 293: 834. The RNAi response also features an endonuclease complex, commonly referred to as an RNA-induced silencing complex (RISC), which mediates cleavage of single-stranded mRNA complementary to the anti-sense strand of the RNAi agent. Cleavage of the target RNA takes place in the middle of the region complementary to the anti-sense strand of the siRNA duplex.

In one aspect, an RNA interference agent includes a single-stranded RNA that interacts with a target RNA sequence to direct the cleavage of the target RNA. Without wishing to be bound by theory, the present disclosure contemplates a long double-stranded RNA introduced into plants and invertebrate cells is broken down into siRNA by a Type III endonuclease known as Dicer. Sharp et al. 2001 Genes Dev. 15:485. Dicer, a ribonuclease-Ill-like enzyme, processes the dsRNA into 19-23 base pair short interfering RNAs with characteristic two base 3' overhangs. Bernstein, et al. 2001 Nature 409:363. The siRNAs are then incorporated into an RNA-induced silencing complex (RISC) where one or more helicases unwind the siRNA duplex, enabling one of the now unpaired siRNA strands to act as a "guide"strand to guide target recognition. Nykanen, et al. 2001 Cell 107:309. Upon binding of the antisense guide strand to the appropriate target mRNA, one or more endonucleases within the RISC cleaves the target to induce silencing. Elbashir, et al. 2001 Genes Dev. 15:188. Thus, in one aspect the present disclosure relates to a single-stranded RNA that promotes the formation of a RISC complex to effect silencing of the target gene.

Kits for RNAi synthesis are commercially available, e.g., from New England Biolabs and Ambion.

A suitable RNAi agent can be selected by any process known in the art or conceivable by one of ordinary skill in the art. For example, the selection criteria can include one or more of the following steps: initial analysis of the EPAS1 gene sequence and design of RNAi agents; this design can take into consideration sequence similarity across species (human, cynomolgus, mouse, etc.) and dissimilarity to other (non-EPAS1) genes; screening of RNAi agents in vitro (e.g., at 10 nM in RKO cells); determination of EC50 in RKO cells; determination of viability of cells treated with RNAi agents, including insensitive cells which do not require EPAS1 for survival, or sensitive cells, which do require EPAS1 for survival; testing with human PBMC (peripheral blood mononuclear cells), e.g., to test levels of TNF-alpha to estimate immunogenicity, wherein immunostimulatory sequences are less desired; testing in human whole blood assay, wherein fresh human blood is treated with an RNAi agent and cytokine/chemokine levels are determined [e.g., TNF-alpha (tumor necrosis factor-alpha) and/or MCPJ (monocyte chemotactic protein 1)], wherein Immunostimulatory sequences are less desired; determination of gene knockdown in vivo using subcutaneous tumors in test animals; EPAS1 target gene modulation analysis, e.g., using a pharmacodynamic (PD) marker, for example, other factors whose expression is affected by EPAS1, wherein EPAS1 knockdown leads to a dose-dependent reduction of abundance of those components; and optimization of specific modifications of the RNAi agents.

The dsRNA molecules (RNAi agents) described herein are thus useful in RNA interference of EPAS1.

Features of a RNAi Agent: Sense Strand, Antisense Strand and (Optional) Overhangs In various aspects, the RNAi agents comprise a first strand and a second strand, e.g., a sense strand and an antisense strand (or an antisense and a sense strand), optionally, either or both ends of either or both strand can comprise unpaired nucleotides (referred to herein as "overhangs").

The term "antisense strand" refers to the strand of a RNAi agent which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule. Generally, the most tolerated mismatches are in the terminal regions, e.g., within 5, 4, 3, or 2 nucleotides of the 5' and/or 3'terminus.

The term "sense strand," as used herein, refers to the strand of a RNAi agent that includes a region that is substantially complementary to a region of the antisense strand as that term is defined herein.

The sequence of a gene may vary from individual to individual, especially at wobble positions within the coding segment, or in the untranslated region; individuals may also differ from each other in coding sequence, resulting in additional differences in mRNA. The sequence of the sense and antisense strands of the RNAi agent can thus be designed to correspond to that of an individual patient, if and where needed. RNAi agents can also be modified in sequence to reduce immunogenicity, binding to undesired mRNAs (e.g., "off-target effects") or to increase stability in the blood. These sequence variants are independent of chemical modification of the bases or 5' or 3' or other end-caps of the RNAi agents.

The RNAi agents can also have overhangs of 0, 1, or 2 overhangs; in the case of a 0 nt overhang, they are blunt-ended. A RNAi agent can thus have 0, 1 or 2 blunt ends. In a "blunt-ended RNAi agent" both strands terminate in a base-pair; thus a blunt-ended molecule lacks either 3' or 5' single-stranded nucleotide overhangs.

The RNAi agents can comprise overhang(s), blunt end(s), and/or 5' and 3' endcap(s).

As used herein, the term "overhang" or "nucleotide overhang" refer to at least one unpaired nucleotide that protrudes from the end of at least one of the two strands of the duplex structure of a RNAi agent. For example, when a 3'-end of one strand of a dsRNA extends beyond the 5'-end of the other strand, or vice versa, this forms a nucleotidic overhang, e.g., the unpaired nucleotide(s) form the overhang. A dsRNA can comprise an overhang of at least one nucleotide; alternatively the overhang can comprise at least two nucleotides, at least three nucleotides, at least four nucleotides, at least five nucleotides or more. An overhang can comprise or consist of a nucleotide/nucleoside analog, including a deoxynucleotide/nucleoside. The overhang(s) may be on the sense strand, the antisense strand or any combination thereof. Furthermore, the nucleotide(s) of an overhang can be present on the 5' end, 3' end or both ends of either an antisense or sense strand of a dsRNA. The RNAi agent can also optionally comprise a cap. The term "Cap" and the like include a chemical moiety attached to the end of a double-stranded nucleotide duplex, but is used herein to exclude a chemical moiety that is a nucleotide or nucleoside. A "3' Cap" is attached at the 3' end of a nucleotide or oligonucleotide and protects the molecule from degradation, e.g., from nucleases, such as those in blood serum or intestinal fluid. A non-nucleotidic 3' cap is not a nucleotide and can replace a TT or UU dinucleotide at the end of a blunt-ended RNAi agent. In one aspect, non-nucleotidic 3' end caps are as disclosed in, for example, WO 2005/021749 and WO 2007/128477; and U.S. Pat. Nos. 8,097,716; 8,084,600; and 8,344,128. A "5' cap" is attached at the 5' end of a nucleotide or oligonucleotide. A cap should not interfere (or unduly interfere) with RNAi activity.

The present disclosure thus contemplates a RNAi agent specific to EPAS1 comprising an antisense strand (which may be contiguous or connected via a linker or loop) in a RNAi agent. In a more specific aspect, an RNAi agent comprises an antisense strand and a sense strand which together comprise a double-stranded or complementary region. In one aspect, it can also optionally comprise one or two overhangs and/or one or two caps. The RNAi agent is used to induce RNA interference of the target gene, EPAS1.

Target and Complementary Sequences

The RNAi agents of the present disclosure target (e.g., specifically bind to, anneal to, etc.) the mRNA encoding EPAS1. The use of the RNAi agent specific to EPAS1 results in a decrease of EPAS1 activity, level and/or expression. Particularly in one aspect, in the case of a disease state characterized by over-expression or hyper-activity of EPAS1, administration of a RNAi agent to EPAS1 knocks down the EPAS1 gene enough to restore a normal level of EPAS1 activity or expression.

In one aspect, the first or second strand of the RNAi comprises a sequence complementary to that of the target nucleic acid, EPAS1.

As used herein, the term "strand comprising a sequence" refers to an oligonucleotide comprising a chain of nucleotides that is described by the sequence referred to using the standard nucleotide nomenclature.

As used herein, "target sequence" or "target gene" refer to a contiguous portion of the nucleotide sequence of an mRNA molecule formed during the transcription of a gene, e.g., a EPAS1 gene, including mRNA that is a product of RNA processing of a primary transcription product. The target portion of the sequence will be at least long enough to serve as a substrate for RNAi-directed cleavage at or near that portion. For example, the target sequence will generally be from 9-36 nucleotides ("nt") in length, e.g., 15-30 nt in length, including all sub-ranges therebetween. As non-limiting examples, the target sequence can be from 15-30 nt, 15-26 nt, 15-23 nt, 15-22 nt, 15-21 nt, 15-20 nt, 15-19 nt, 15-18 nt, 15-17 nt, 18-30 nt, 18-26 nt, 18-23 nt, 18-22 nt, 18-21 nt, 18-20 nt, 19-30 nt, 19-26 nt, 19-23 nt, 19-22 nt, 19-21 nt, 19-20 nt, 19 nt, 20-30 nt, 20-26 nt, 20-25 nt, 20-24 nt, 20-23 nt, 20-22 nt, 20-21 nt, 20 nt, 21-30 nt, 21-26 nt, 21-25 nt, 21-24 nt, 21-23 nt, or 21-22 nt, 21 nt, 22 nt, or 23 nt. The sense and antisense strands of the RNAi comprise a sequence complementary to that of the target nucleic acid, EPAS1.

As used herein, and unless otherwise indicated, the term "complementary" refers to the ability of an oligonucleotide or polynucleotide comprising a first nucleotide sequence to hybridize and form a duplex structure under certain conditions with an oligonucleotide or polynucleotide comprising a second nucleotide sequence. Such conditions can, for example, be stringent, e.g., 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

Complementary sequences within a RNAi agent, e.g., within a dsRNA as described herein, include base-paired oligonucleotides or polynucleotides comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they may form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single-stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein. The term "overhang"describes an unpaired nucleotide at the 3' or 5' end of a double-stranded nucleotide duplex, as described above. In one aspect, the overhang is 1 to 4 nt long and is on the 3' end.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but are not limited to, Wobble or Hoogstein base pairing. The terms "complementary," "fully complementary" and "substantially complementary" herein may furthermore be used with respect to the base matching between the sense strand and the antisense strand of a dsRNA, or between the antisense strand of a RNAi agent and a target sequence, as will be understood from the context of their use. As used herein, a polynucleotide that is "substantially complementary to at least part of" a messenger RNA (mRNA) refers to a polynucleotide that is substantially complementary to a contiguous portion of the mRNA of interest (e.g., an mRNA encoding EPAS1). For example, a polynucleotide is complementary to at least a part of a EPAS1 mRNA if the sequence is substantially complementary to a non-interrupted portion of an mRNA encoding EPAS1.

Thus, the RNAi agent of the present disclosure is complimentary or substantially complimentary to a target sequence in the target EPAS1 and is double-stranded, comprising a sense and an antisense strand (which can be contiguous, linked via a loop, or otherwise joined), where the double-stranded region can be 9 to 36 bp long (particularly for example, 19-22 bp or 19-23 bp long), and can furthermore optionally comprise a 3' or 5' overhang, and the RNAi agent can furthermore comprise a 3' cap. The RNAi agent mediates RNA interference, down-regulating or inhibiting the level, expression and/or activity of EPAS1, and/or establishing or re-establishing an approximately normal level of EPAS1 and/or EPAS1 activity, or other biological function related to EPAS1.

Thus, the RNAi agent of the present disclosure is complimentary or substantially complimentary to a target sequence in the target EPAS1 and is double-stranded, comprising a sense and an antisense strand (which can be contiguous, linked via a loop, or otherwise joined), where the double-stranded region can be 9 to 36 bp long (particularly for example, 19-22 bp or 19-23 bp long), and can furthermore optionally comprise a 3' or 5' overhang, and the RNAi agent can furthermore comprise a 3' cap. The RNAi agent mediates RNA interference, down-regulating or inhibiting the level, expression and/or activity of EPAS1, and/or establishing or re-establishing an approximately normal level of EPAS1 activity or expression.

The term "double-stranded RNA" or "dsRNA," as used herein, refers to an RNAi agent comprising a first and a second strand; e.g., a composition that includes an RNA molecule or complex of molecules having a hybridized duplex region that comprises two anti-parallel and substantially complementary nucleic acid strands, which will be referred to as having "sense"and "antisense" orientations with respect to a target RNA. The antisense strand, with respect to the mRNA target, is also called the "guide" strand, and the sense strand is also called the "passenger" strand. As used herein, depending on the context, the "first" strand can be the guide or antisense strand, and the "second" strand can be the passenger or sense strand. Also as used herein, again depending on the context, the "first" strand can be the passenger or sense strand, and the "second" strand can be the guide or antisense. The passenger strand can include at least one or more of the following: one or more extra nucleotides (e.g., a bulge or 1 nt loop) compared to the other strand, a nick, a gap, etc., compared to the other strand. In various aspects, the first strand is the sense strand and the second strand is the anti-sense strand. In other aspects, the first strand is the anti-sense strand, and the second strand is the sense strand.

The duplex region can be of any length that permits loading into the RISC complex and subsequent specific degradation of a desired target RNA through a RISC pathway, but will typically range from 9 to 36 base pairs ("bp") in length, e.g., 15-30 base pairs in length. Considering a duplex between 9 and 36 base pairs, the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 bp and any sub-range therebetween, including, but not limited to 15-30 base pairs, 15-26 bp, 15-23 bp, 15-22 bp, 15-21 bp, 15-20 bp, 15-19 bp, 15-18 bp, 15-17 bp, 18-30 bp, 18-26 bp, 18-23 bp, 18-22 bp, 18-21 bp, 18-20 bp, 19-30 bp, 19-26 bp, 19-23 bp, 19-22 bp, 19-21 bp, 19-20 bp, 19 bp, 20-30 bp, 20-26 bp, 20-25 bp, 20-24 bp, 20-23 bp, 20-22 bp, 20-21 bp, 20 bp, 21-30 bp, 21-26 bp, 21-25 bp, 21-24 bp, 21-23 bp, 21-22 bp, 21 bp, 22 bp, or 23 bp.

The dsRNAs generated in the cell by processing with Dicer and similar enzymes are generally in the range of about 19 to about 22 base pairs in length, although artificial RNAi agents can be synthesized or made by any method known in the art. One strand of the duplex region of a dsRNA comprises a sequence that is substantially complementary to a region of a target RNA. The two strands forming the duplex structure can be from a single RNA molecule having at least one self-complementary duplex region, or can be formed from two or more separate RNA molecules that hybridize to form the duplex. Where the duplex region is formed from two self-complementary regions of a single molecule, the molecule can have a duplex region separated by a single stranded chain of nucleotides (herein referred to as a "hairpin loop", e.g., such as found in an shRNA construct) between the 3'-end of one strand and the 5'-end of the respective other strand forming the duplex structure. The hairpin loop can comprise at least one unpaired nucleotide; in some aspects the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are comprised by separate RNA molecules, those molecules need not, but can be covalently connected. Where the two strands are connected covalently by a hairpin loop, the construct is generally referred to herein and in the art as a "shRNA". Where the two strands are connected covalently by means other than a hairpin loop, the connecting structure is referred to as a "linker." The term "siRNA" is also used herein to refer to a dsRNA as described above.

RNAi Agents Lowering or Normalizing EPAS1 Level, Expression and/or Activity

RNAi agents for targeting EPAS1 include those which bind to a EPAS1 sequence provided herein and which work to reduce EPAS1 through a RNAi mechanism. Example RNAi agents (e.g., siRNAs) to EPAS1 are provided, e.g., in Table 1.

Any method known in the art can be used to measure changes in EPAS1 activity, level, and/or expression induced by a EPAS1 RNAi agent. Measurements can be performed at multiple timepoints, prior to, during and after administration of the RNAi agent, to determine the effect of the RNAi agent.

The RNAi agents of the present disclosure silence, inhibit the expression of, down-regulate the expression of, and/or suppress the expression of EPAS1, such that an approximately normal level of EPAS1 activity or expression is restored.

In addition, in various aspects, depending on the disease condition and biological context, it is acceptable to use the RNAi agents of the present disclosure to establish a level of EPAS1 expression, activity and/or level which is below the normal level, or above the normal level, depending on the therapeutic outcome that is desired.

Any method known in the art can be used to measure changes in EPAS1 activity, level and/or expression induced by a EPAS1 siRNA. Measurements can be performed at multiple timepoints, prior to, during and after administration of the siRNA, to determine the effect of the siRNA.

The terms "silence," "inhibit the expression of," "down-regulate the expression of,""suppress the expression of," and the like, in so far as they refer to a EPAS1 gene, herein refer to the at least partial suppression of the expression of a EPAS1 gene, as manifested by a reduction of the amount of EPAS1 mRNA which may be isolated from or detected in a first cell or group of cells in which a EPAS1 gene is transcribed and which has or have been treated such that the expression of a EPAS1 gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\% \qquad \text{Equation 1}$$

Alternatively, the degree of inhibition may be given in terms of a reduction of a parameter that is functionally linked to EPAS1 gene expression, e.g., the amount of protein encoded by a EPAS1 gene, alteration in expression of a protein whose expression is dependent on EPAS1, etc. In principle, EPAS1 gene silencing may be determined in any cell expressing EPAS1, either constitutively or by genomic engineering, and by any appropriate assay. However, when a reference or control is needed in order to determine whether a given RNAi agent inhibits the expression of EPAS1 by a certain degree and therefore is encompassed by the instant disclosure, the assays provided in the Examples below shall serve as such reference.

For example, in certain instances, expression of EPAS1 is suppressed by at least about 10%, 15%, 20%, 25%, 30%, 35%, 40%, 45%, or 50% by administration of a RNAi agent featured in the present disclosure. In some aspects, EPAS1 is suppressed by at least about 60%, 70%, or 80% by administration of a RNAi agent featured in the present disclosure. In some aspects, EPAS1 is suppressed by at least about 85%, 90%, or 95% or more by administration of a RNAi agent, as described herein. In one aspect, the degree of EPAS1 suppression is determined by loss of full length EPAS1 mRNA in a treated cell compared to an untreated cell. In one aspect, the degree of EPAS1 suppression is determined with a phenotypic assay that monitors loss of proliferative activity and/or cell death. Other aspects are as provided in the Examples.

A suitable RNAi agent can be selected by any process known in the art or conceivable by one of ordinary skill in the art. For example, the selection criteria can include one or more of the following steps: initial analysis of the EPAS1 gene sequence and design of RNAi agents; this design can take into consideration sequence similarity across species (human, cynomolgus, mouse, etc.) and dissimilarity to other (non-EPAS1) genes; screening of RNAi agents in vitro (e.g., at 10 nM and 1 nM in 786-O cells); selection of RNAi agents with high knock-down at 10 nM and 1 nM in 786-O cells; determination of EC50 in 786-O cells; confirmation of EC50 in a RCC cell line (786-O cells); analysis of a lack of effect on cell growth relative to a control siRNA; reduction in 786-O cells of expression of a HRE-luc (luciferase) reporter gene and not control UB6-luc (luciferase) reporter gene; Western blots to measure Hif-1, Hif-2, and ARNT levels; testing with human PBMC (peripheral blood mononuclear cells), e.g., to test levels of TNF-alpha to estimate immunogenicity, wherein immunostimulatory sequences are less desired; testing in human whole blood assay, wherein fresh human blood is treated with an RNAi agent and cytokine/chemokine levels are determined [e.g., TNF-alpha (tumor necrosis factor-alpha) and/or MCP1 (monocyte chemotactic protein 1)], wherein immunostimulatory sequences are less desired; determination of gene knockdown in vivo using subcutaneous tumors in test animals; EPAS1 target gene modulation analysis, e.g., using a pharmacodynamic (PD) marker, for example, EGLN3, SLC2A1 and VEGF, wherein EPAS1 knockdown leads to a dose-dependent alteration of EGLN3, SLC2A1 and VEGF expression in cells; and optimization of specific modifications of the RNAi agents. As appropriate, other cell lines can be used in place of those listed above to identify RNAi agents capable of lowering EPAS1 levels or decrease symptoms of a EPAS1-related disease.

By "lower" in the context of EPAS1 or a symptom of a EPAS1-related disease is meant a statistically significant decrease in such level. The decrease can be, for example, at least 10%, at least 20%, at least 30%, at least 40% or more. If, for a particular disease, or for an individual suffering from a particular disease, the levels or expression of EPAS1 are elevated, treatment with a EPAS1 RNAi agent of the present disclosure can particularly reduce the level or expression of EPAS1 to a level considered in the literature as within the range of normal for an individual without such disorder, or to a level that reduces or ameliorates symptoms of a disease. The level or expression of EPAS1 can be measured by evaluation of mRNA (e.g., via Northern blots or PCR), or protein (e.g., Western blots). The effect of a RNAi agent on EPAS1 expression can be determined by measuring EPAS1 gene transcription rates (e.g., via Northern blots; or reverse transcriptase polymerase chain reaction or real-time polymerase chain reaction).

As used herein, "down-regulates" refers to any statistically significant decrease in a biological activity and/or expression of EPAS1, including full blocking of the activity (i.e., complete inhibition) and/or expression. For example, "down-regulation" can refer to a decrease of at least about 10, 20, 30, 40, 50, 60, 70, 80, 90 or 100% in EPAS1 level, activity and/or expression.

As used herein, the term "inhibit" or "inhibiting" EPAS1 refers to any statistically significant decrease in biological level, activity and/or expression of EPAS1, including full blocking of the activity and/or expression. For example, "inhibition" can refer to a decrease of at least about 10, 20, 30, 40, 50, 60, 70, 80, 90 or 100% in EPAS1 level, activity and/or expression. As used herein, the term "inhibit" similarly refers to a significant decrease in level, activity and/or expression, while referring to any other biological agent or composition.

By "level", it is meant that the EPAS1 RNAi agent can alter the level of EPAS1, e.g., the level of EPAS1 mRNA or the level of EPAS1 protein, or the level of activity of EPAS1.

Some diseases include any EPAS1-related disease disclosed herein or known in the literature. Particularly in one aspect, in the case of a disease characterized by over-expression and/or hyper-activity of EPAS1, administration of a RNAi agent to EPAS1 reduces the level, expression and/or activity of EPAS1. Thus, in various aspects, administration of a RNAi agent to EPAS1 particularly establishes or re-establishes a normal or approximately normal level of EPAS1 activity, expression and/or level.

By "normal" or "approximately normal" in terms of level, expression and/or activity, is meant at least: about 50%, about 60%, about 70%, about 80%, about 90%, and/or about 100%; and/or no more than: about 100%, about 120%, about 130%, about 140%, or about 150% of the level, expression or activity of EPAS1 in a healthy cell, tissue, or organ. This can be measured using, for example, lung or kidney homogenates, as described in Gambling et al. 2 Kidney Intl. 65: 1774-1781. Particularly in one aspect, administration of the appropriate amount of the appropriate EPAS1 RNAi agent restores EPAS1 level, activity and/or expression to about 50% to about 150%, more particularly about 60% to about 140%, more particularly to about 70% to about 130%, more particularly to about 80% to about 120%, more particularly to about 90% to about 110%, and most particularly to about 100% of that of a healthy cell, tissue or organ. Administration of a EPAS1 RNAi to a patient with a EPAS1-related disease thus particularly restores the level, activity, and/or expression of EPAS1 and the level of $Na^+$ reabsorption to an approximately normal level, as determined by direct measurements of EPAS1 mRNA or protein levels, or indirect determinations. In addition, the preferred target amount of EPAS1 level, expression and/or activity after EPAS1 RNAi agent administration can be calculated to take into account any other perturbations in a EPAS1-related pathway. For example, if another factor in a EPAS1-related pathway is either over- or under-expressed, EPAS1 level, expression or activity may be modulated to attain a more normal state.

In addition, in various aspects, depending on the disease condition and biological context, it is acceptable to use the RNAi agents of the present disclosure to establish a level of EPAS1 expression, activity and/or level which is below the normal level, or above the normal level.

Types of RNAi Agents and Modification Thereof

The use of RNAi agents or compositions comprising an antisense nucleic acid to down-modulate the expression of a particular protein in a cell is well known in the art. A RNAi agent comprises a sequence complementary to, and is capable of hydrogen bonding to, the coding strand of another nucleic acid (e.g., an mRNA). Thus, in various aspects, the RNAi agents of the present disclosure encompass any RNAi agents which target (e.g., are complementary, capable of hybridizing or hydrogen bonding to, etc.) any sequence presented, e.g., in any of the Tables.

Once a functional guide strand has been identified, many variations to the guide and/or passenger strand can be made. For example, the RNAi agent may have modifications internally, or at one or both ends. The modifications at the ends can help stabilize the RNAi agent, protecting it from degradation by nucleases in the blood. The RNAi agents may optionally be directed to regions of the EPAS1 mRNA known or predicted to be near or at splice sites of the gene.

A RNAi agent can be constructed using chemical synthesis and enzymatic ligation reactions using procedures known in the art. For example, RNAi agent can be chemically synthesized using naturally-occurring nucleotides or variously modified nucleotides designed to decrease off-target effects, and/or increase the biological stability of the molecules or to increase the physical stability of the duplex formed between the antisense and sense nucleic acids, e.g., phosphorothioate derivatives and acridine substituted nucleotides can be used.

"G," "C," "A," "T" and "U" each generally stand for a nucleotide that contains guanine, cytosine, adenine, thymidine and uracil as a base, respectively. However, the terms "ribonucleotide", "deoxynucleotide", or "nucleotide" can also refer to a modified nucleotide or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of dsRNA featured in the present disclosure by a nucleotide containing, for example, inosine. In another example, adenine and cytosine anywhere in the oligonucleotide can be replaced with guanine and uracil, respectively to form Wobble base pairing with the target mRNA. Sequences containing such replacement moieties are suitable for the compositions and methods featured in the present disclosure.

The skilled artisan will recognize that the term "RNA molecule" or "ribonucleic acid molecule" encompasses not only RNA molecules as expressed or found in nature (i.e., are naturally occurring), but also non-naturally occurring analogs and derivatives of RNA comprising one or more ribonucleotide/ribonucleoside analogs or derivatives as described herein or as known in the art. The RNA can be modified in the nucleobase structure or in the ribose-phosphate backbone structure, e.g., as described herein below. However, the molecules comprising ribonucleoside analogs or derivatives must retain the ability to form a duplex. As non-limiting examples, either or both strand of an RNAi agent can comprise at least one modified ribonucleoside, including but not limited to a 2'-O-methyl modified nucleotide, a nucleoside comprising a 5' phosphorothioate group, a terminal nucleoside linked to a cholesteryl derivative or dodecanoic acid bisdecylamide group, a locked nucleoside, an abasic nucleoside, a 2'-deoxy-2'-fluoro modified nucleoside, a 2'-amino-modified nucleoside, 2'-alkyl-modified nucleoside, morpholino nucleoside, an unlocked ribonucleotide (e.g., an acyclic nucleotide monomer, as described in WO 2008/147824), a phosphoramidate or a non-natural base comprising nucleoside, or any combination thereof. Alternatively, an RNA molecule can comprise at least two modified ribonucleosides, at least 3, at least 4, at least 5, at least 6, at least 7, at least 8, at least 9, at least 10, at least 15, at least 20 or more, up to the entire length of the dsRNA molecule. The modifications need not be the same for each of such a plurality of modified ribonucleosides in an RNA molecule. In one aspect, modified RNAs contemplated for use in methods and compositions described herein are peptide nucleic acids (PNAs) that have the ability to form the required duplex structure and that permit or mediate the specific degradation of a target RNA via a RISC pathway. In addition, the RNAi agent can comprise one or two strands which are a RNA, or a mixture of RNA, DNA, LNA, Morpholino, UNA, TNA, GNA, and/or FANA, modified RNA, etc. As a non-limiting example, one or both strands could be, for example, RNA except that one or more nucleotides is replaced by DNA, LNA, Morpholino, UNA, TNA, GNA, and/or FANA, and/or modified RNA (e.g., any modified RNA disclosed herein or known in the art, such as 2' modified RNA, including but not limited to 2'-F, 2'-OMe, 2'-MOE RNA, etc.).

Examples of modified nucleotides which can be used to generate the RNAi agent include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. These and other example modifications are shown in FIG. 1, herein, and Usman et al. 1992 TIBS 17:34; Usman et al. 1994 Nucl. Acids Symp. Ser. 31: 163; Burgin et al. 1996 Biochem. 35: 14090.

A "modified variant" of a sequence disclosed herein includes any variant comprising the same sequence, but with a modification in the base, sugar, phosphate or backbone (but not a base substitution, e.g., A for G, or C for U). Thus, a modified variant can comprise any modified nucleotide described above (e.g., 5-fluorouracil, 5-bromouracil, 5-chlorouracil, 5-iodouracil, hypoxanthine, xantine, 4-acetylcytosine, 5-(carboxyhydroxylmethyl) uracil, etc.). When a base is replaced by a corresponding modified base (e.g., A for modified A), these modified nucleotides do not constitute a mismatch or base difference. Thus a given sequence with a U at a particular position and a modified variant comprising a 5-fluorouracil, 5-bromouracil, 5-chlorouracil, or 5-iodouracil at the same sequence would differ by 0 nt (or have no mismatches); however, a given sequence with a C at a particular position and a different sequence with a 5-fluorouracil (wherein the two sequences are otherwise identical) would differ by 1 nt (1 mismatch).

Replacing the 3'-terminal nucleotide overhanging segments of a 21-mer siRNA duplex having two-nucleotide 3'-overhangs with deoxyribonucleotides does not have an adverse effect on RNAi activity. Replacing up to four nucleotides on each end of the siRNA with deoxyribonucleotides has been well tolerated, whereas complete substitution with deoxyribonucleotides results in no RNAi activity. International PCT Publication No. WO 00/44914, and Beach et al. International PCT Publication No. WO 01/68836 preliminarily suggest that siRNA may include modifications to either the phosphate-sugar backbone or the nucleoside to include at least one of a nitrogen or sulfur heteroatom. Kreutzer et al. Canadian Patent Application No. 2,359,180, also describe certain chemical modifications for use in dsRNA constructs in order to counteract activation of double-stranded RNA-dependent protein kinase PKR, specifically 2'-amino or 2'-O-methyl nucleotides, and nucleotides containing a 2'-O or 4'-C methylene bridge. Additional 3'-terminal nucleotide overhangs include dT (deoxythimidine), 2'-0,4'-C-ethylene thymidine (eT), and 2-hydroxyethyl phosphate (hp). 4-thiouracil and 5-bromouracil substitutions can also be made. Parrish et al. 2000 Molecular Cell 6: 1077-1087.

Those skilled in the art will appreciate that it is possible to synthesize and modify the siRNA as desired, using any conventional method known in the art (see Henschel et al. 2004 DEQOR: a web-based tool for the design and quality control of siRNAs. Nucleic Acids Research 32 (Web Server Issue): W113-W120). In addition, if the RNAi agent is a shRNA, it will be apparent to those skilled in the art that there are a variety of regulatory sequences (for example, constitutive or inducible promoters, tissue-specific promoters or functional fragments thereof, etc.) which are useful for shRNA expression construct/vector.

There are several examples in the art describing sugar, base, phosphate and backbone modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-flouro, 2'-O-methyl, 2'-O-allyl, 2'-H, nucleotide base modifications (for a review see Usman and Cedergren 1992 TIBS. 17: 34; Usman et al. 1994 Nucleic Acids Symp. Ser. 31: 163; Burgin et al. 1996 Biochemistry 35: 14090). Sugar modification of nucleic acid molecules are extensively described in the art.

In various aspects, the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

Additional modifications and conjugations of RNAi agents have been described. Soutschek et al. 2004 Nature 432: 173-178 presented conjugation of cholesterol to the 3'-end of the sense strand of a siRNA molecule by means of a pyrrolidine linker, thereby generating a covalent and irreversible conjugate. Chemical modifications (including conjugation with other molecules) of RNAi agents may also be made to improve the in vivo pharmacokinetic retention time and efficiency.

In various aspects, the RNAi agent to EPAS1 comprises at least one 5'-uridine-adenine-3' (5'-ua-3') dinucleotide, wherein the uridine is a 2'-modified nucleotide; at least one 5'-uridine-guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; and/or at least one 5'-uridine-uridine-3' (5'-uu-3') dinucleotide, wherein the 5'-uridine is a 2'-modified nucleotide. In certain aspects, the RNAi agent can comprise a non-natural nucleobase, wherein the non-natural nucleobase is difluorotolyl, nitroindolyl, nitropyrrolyl, or nitroimidazolyl. In a particular aspect, the non-natural nucleobase is difluorotolyl. In certain aspects, only one of the two oligonucleotide strands contains a non-natural nucleobase. In certain aspects, both of the oligonucleotide strands contain a non-natural nucleobase.

In another aspect, the RNAi comprises a gap or contains mismatch comprising an abasic nucleotide.

In another aspect, the RNAi agent has a single-stranded nick (e.g., a break or missing bond in the backbone). In various aspects, a single-stranded nick can be in either the sense or anti-sense strand, or both.

This nick can be, for example, in the sense strand, producing a small internally segmented interfering RNA, or sisiRNA, which may have less off-target effects than the corresponding RNAi agent without a nick. See, for example, WO 2007/107162 to Wengels and Kjems.

The antisense nucleic acid or RNAi agent can also have an alternative backbone such as locked nucleic acids (LNA), Morpholinos, peptidic nucleic acids (PNA), threose nucleic acid (TNA), or glycol nucleic acid (GNA), or FANA and/or it can be labeled (e.g., radiolabeled or otherwise tagged). FANA are described in Dowler et al. 2006 Nucl. Acids Res. 34: 1669-1675.

One or both strands can comprise an alternative backbone.

In yet another aspect, the RNAi agent employed by the methods of the present disclosure can include an α-anomeric nucleic acid molecule. An α-anomeric nucleic acid molecule forms specific double-stranded hybrids with complementary RNA in which, contrary to the usual β-units, the strands run parallel to each other. Gaultier et al. 1987 Nucleic Acids. Res. 15: 6625-6641.

The antisense nucleic acid molecule can also comprise a 2'-o-methylribonucleotide (Inoue et al. 1987 Nucleic Acids Res. 15: 6131-6148) or a chimeric RNA-DNA analogue (Inoue et al. 1987 FEBS Lett. 215: 327-330).

Other modifications and/or other changes can be made to the RNAi agent. A portion of the RNAi agent can be double-stranded DNA, while another portion is double-stranded RNA, forming a DNA-RNA chimera (See, for example, Yamato et al. 2011. Cancer Gene Ther. 18: 587-597). Mismatches between the guide and passenger stand can also be introduced, though some positions may be better suited than others (See, for example, U.S. Patent App. No. 2009/0209626 to Khvorova). The passenger strand can also be shortened, to as short as 15 or 16 nt, while the guide strand remains 19 nt or longer (See, for example, Sun et al. 2008 Nature Biotech. 26: 1379-1382; and Chu and Rana 2008 RNA 14: 1714-1719). This can increase incorporation of the guide strand into the RNA-induced Silence Complex (RISC), and decrease incorporation of the passenger strand, than reducing off-target effects. In some cases, the passenger strand may be more amenable to modification (e.g., single-stranded nicking, nucleotide modifications, and shortening) than the guide strand.

These and many other modifications can be made once a functional guide strand is identified.

Pharmaceutical Compositions of RNAi Agents

As used here, a "pharmaceutical composition" comprises a pharmaceutically effective amount of one or more EPAS1 RNAi agent, a pharmaceutically acceptable carrier, and, optionally, an additional disease treatment which works synergistically with the RNAi agent. As used herein, "pharmacologically effective amount," "therapeutically effective amount" or simply "effective amount" refers to that amount of a RNAi agent effective to produce the intended pharmacological, therapeutic or preventive result. For example, if a given clinical treatment is considered effective where there is at least a 10% reduction in a measurable parameter associated with a disease or disorder, a therapeutically effective amount of a drug for the treatment of that disease or disorder is the amount necessary to effect at least a 10% reduction in that parameter. In this aspect, a therapeutically effective amount of a RNAi agent targeting EPAS1 can reduce EPAS1 protein levels by at least 10%. In additional aspects, a given clinical treatment is considered effective where there is at least a 15, 20, 25, 30, 35, 40, 45, 50, 55, 60, 65, 70, 75, 80, 85, 90 or 95% reduction in a measurable parameter associated with a disease or disorder, and the therapeutically effective amount of a drug for the treatment of that disease or disorder is the amount necessary to effect at least a 15, 20, 25, 30, 35, 40, 45, 50, 55, 60, 65, 70, 75, 80, 85, 90 or 95% reduction, respectively, in that parameter.

The term "pharmaceutically acceptable carrier" refers to a carrier for administration of a therapeutic agent. Such carriers include, but are not limited to, lipid nanoparticles, saline, buffered saline, dextrose, water, glycerol, ethanol, and combinations thereof. The term specifically excludes cell culture medium. Any appropriate pharmaceutical carrier known in the art can be used in conjunction with the RNAi agents disclosed herein.

Pharmaceutical Composition Comprising a RNAi Agent to EPAS1

Additional components of a pharmaceutical composition comprising a RNAi Agent to EPAS1 are contemplated to aid in delivery, stability, efficacy, or reduction of immunogenicity.

Liposomes have been used previously for drug delivery (e.g., delivery of a chemotherapeutic). Liposomes (e.g., cationic liposomes) are described in PCT publications WO02/100435A1, WO03/015757A1, WO04029213A2; and WO/2011/076807; U.S. Pat. Nos. 5,962,016; 5,030,453; and 6,680,068; and U.S. Patent Application 2004/0208921. A process of making liposomes is also described in WO04/002453A1. Furthermore, neutral lipids have been incorporated into cationic liposomes (e.g., Farhood et al. 1995), as well as PEGylated lipids.

Cationic liposomes have been used to deliver RNAi agent to various cell types (Sioud and Sorensen 2003; U.S. Patent Application 2004/0204377; Duxbury et al., 2004; Donze and Picard, 2002).

Use of neutral liposomes disclosed in Miller et al. 1998, and U.S. Patent Application 2003/0012812.

As used herein, the term "SNALP" refers to a stable nucleic acid-lipid particle. A SNALP represents a vesicle of lipids coating a reduced aqueous interior comprising a nucleic acid such as an iRNA or a plasmid from which an iRNA is transcribed. SNALPs are described, e.g., in U.S. Patent Application Publication Nos. 20060240093, 20070135372, and in International Application No. WO 2009082817.

Chemical transfection using lipid-based, amine-based and polymer-based techniques is disclosed in products from Ambion Inc., Austin, Tex.; and Novagen, EMD Biosciences, Inc, an Affiliate of Merck KGaA, Darmstadt, Germany); Ovcharenko D (2003) "Efficient delivery of siRNAs to human primary cells." Ambion TechNotes 10 (5): 15-16). Additionally, Song et al. (Nat Med. published online (Feb. 10, 2003) doi: 10.1038/nm828) and others [Caplen et al. 2001 Proc. Natl. Acad. Sci. (USA), 98: 9742-9747; and McCaffrey et al. Nature 414: 34-39] disclose that liver cells can be efficiently transfected by injection of the siRNA into a mammal's circulatory system.

A variety of molecules have been used for cell-specific RNAi agent delivery. See, for example, WO/2011/076807. For example, the nucleic acid-condensing property of protamine has been combined with specific antibodies to deliver siRNAs. Song et al. 2005 Nat Biotech. 23: 709-717. The self-assembly PEGylated polycation polyethylenimine (PEI) has also been used to condense and protect siRNAs. Schiffelers et al. 2004 Nucl. Acids Res. 32: e149, 141-110.

The RNAi agents of the present disclosure can be delivered via, for example, Lipid nanoparticles (LNP); neutral liposomes (NL); polymer nanoparticles; double-stranded RNA binding motifs (dsRBMs); or via modification of the RNAi agent (e.g., covalent attachment to the dsRNA) or by any method known in the art for delivery of a RNAi agent comprising nucleic acids.

Lipid nanoparticles (LNP) are self-assembling cationic lipid based systems. These can comprise, for example, a neutral lipid (the liposome base); a cationic lipid (for siRNA loading); cholesterol (for stabilizing the liposomes); and PEG-lipid (for stabilizing the formulation, charge shielding and extended circulation in the bloodstream).

The cationic lipid can comprise, for example, a headgroup, a linker, a tail and a cholesterol tail. The LNP can have, for example, good tumor delivery, extended circulation in the blood, small particles (e.g., less than 100 nm), and stability in the tumor microenvironment (which has low pH and is hypoxic).

Neutral Liposomes (NL) are Non-cationic Lipid Based Particles.

Polymer nanoparticles are self-assembling polymer-based particles.

Double-stranded RNA binding motifs (dsRBMs) are self-assembling RNA binding proteins, which will need modifications.

EPAS1 RNAi Agent Compositions in a Lipid Nanoparticles (LNP) Comprising a Neutral Lipid; a Cationic Lipid; Cholesterol; and PEG-lipid Lipid nanoparticles (LNP) are self-assembling cationic lipid based systems. These can comprise, for example, a neutral lipid (the liposome base); a cationic lipid (for siRNA loading); cholesterol (for stabilizing the liposomes); and PEG-lipid (for stabilizing the formulation, charge shielding and extended circulation in the bloodstream).

A Neutral Lipid

A neutral lipid is, for example, the liposome base.

A Cationic Lipid

A cationic lipid is, for example, for siRNA loading.

Cholesterol

Cholesterol is, for example, for stabilizing the liposomes)

PEG-lipid (for Stabilizing the Formulation, Charge Shielding and Extended Circulation in the Bloodstream).

PEG-lipid is, for example, for stabilizing the formulation, charge shielding and extended circulation in the bloodstream.

A Particular Formulation, and Ratios of a Neutral Lipid; a Cationic Lipid; Cholesterol; and PEG-lipid.

In one aspect, the formulation comprises:

Compound 1

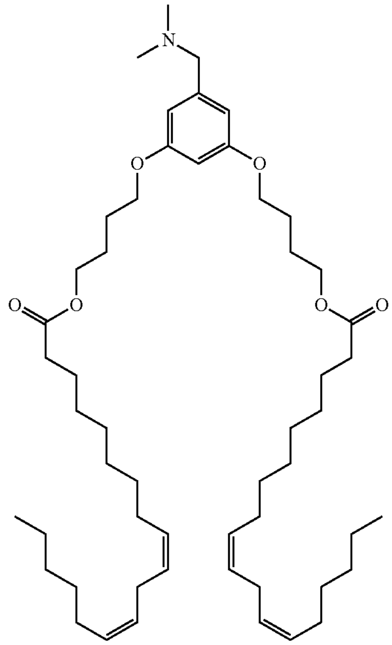

In one aspect, the formulation comprises:

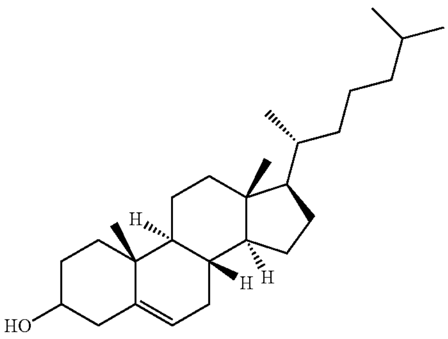

cholesterol

In one aspect, the formulation comprises:

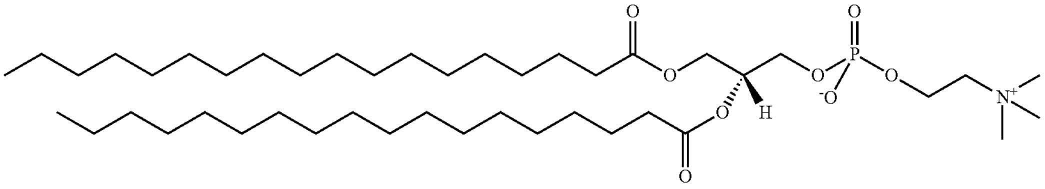

DSPC

In one aspect, the formulation comprises:

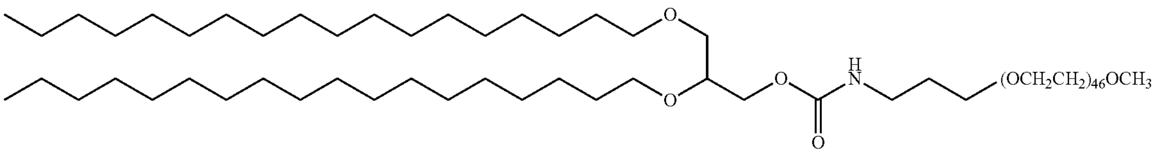

cDSA—PEG (polydisperse)

PEG-lipid

In one aspect, the formulation comprises a RNAi agent comprising any sequence disclosed herein, or any portion thereof (e.g., 15 or more contiguous nt with 0, 1, 2 or 3 mismatches), optionally with any lengths, modifications, terminal dinucleotides, endcaps, combinations of RNAi agents, combination therapy involving a EPAS1 RNAi agent and another agent, conjugation with other components, compositions or methods or techniques for delivery, and/or disease treatment (any of which can be described herein or known in the art), further comprising one or more of compound 1, cholesterol, DSPC, and/or PEG-lipid. In one aspect, the formulation is 45% compound 1 (cationic lipid), 44% (cholesterol), 9% (DSPC) and 2% (PEG-lipid)—all molar ratios. These are known in the art and/or described in U.S. Patent App. No. 61/774,759, filed Mar. 8, 2013. In one aspect, the disclosure pertains to a composition comprising 45% compound 1 (cationic lipid), 44% (cholesterol), 9% (DSPC) and 2% (PEG-lipid) [all molar ratios] and a RNAi agent of the sequence of RNAi agent 5049. In one aspect, the disclosure pertains to a composition comprising 45% compound 1 (cationic lipid), 44% (cholesterol), 9% (DSPC) and 2% (PEG-lipid) [all molar ratios]and a RNAi agent of the sequence of RNAi agent 3875. In one aspect, the disclosure pertains to a composition comprising 45% compound 1 (cationic lipid), 44% (cholesterol), 9% (DSPC) and 2% (PEG-lipid) [all molar ratios] and a RNAi agent comprising a first strand and a second strand, wherein the sequence of the first strand is or comprises the sequence of SEQ ID NO: 300, and/or the sequence of the second strand is or comprises the sequence of SEQ ID NO: 301.

In one aspect, the disclosure pertains to a composition comprising 45% compound 1 (cationic lipid), 44% (cholesterol), 9% (DSPC) and 2% (PEG-lipid) [all molar ratios] and a RNAi agent comprising a first strand and a second strand, wherein the sequence of the first strand is or comprises the sequence of SEQ ID NO: 302, and/or the sequence of the second strand is or comprises the sequence of SEQ ID NO: 303. In one aspect, the disclosure pertains to a composition comprising 45% compound 1 (cationic lipid), 44% (cholesterol), 9% (DSPC) and 2% (PEG-lipid) [all molar ratios] and a RNAi agent comprising a first strand and a second strand, wherein the sequence of the first strand is or comprises the sequence of SEQ ID NO: 303, and/or the sequence of the second strand is or comprises the sequence of SEQ ID NO: 304.

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified.

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 10% cationic lipid [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 20% cationic lipid [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 30% cationic lipid [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 40% cationic lipid [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 45% cationic lipid [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 10% compound 1 (cationic lipid) [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 20% compound 1 (cationic lipid) [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 30% compound 1 (cationic lipid) [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 40% compound 1 (cationic lipid) [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 45% compound 1 (cationic lipid) [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 10% cholesterol [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 20% cholesterol [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 30% cholesterol [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 40% cholesterol [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 44% cholesterol [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 1% DSPC [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 2% DSPC [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 5% DSPC [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 7.5% DSPC [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 9% DSPC [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 1% PEG [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 2% PEG [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 1% cDSA-PEG [molar ratios].

In one aspect, the disclosure pertains to a composition comprising a RNAi agent comprising a first strand and a second strand, wherein the sequence of the first strand is or comprises the sequence of SEQ ID NO: 303 or nt 1-19 of SEQ ID NO: 303, and/or the sequence of the second strand is or comprises the sequence of SEQ ID NO: 304 or nt 1-19 of SEQ ID NO: 304, wherein the first and/or second strand are modified or not modified, and wherein the composition further comprises at least about 2% cDSA-PEG [molar ratios].

Any of the recited amounts of components (compound 1, cationic lipid, cholesterol, DSPC, PEG, etc.) can be mixed/matched or combined, provided they are not mutually exclusive, in various other aspects of the disclosure.

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified.

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 10% cationic lipid [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 20% cationic lipid [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 30% cationic lipid [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 40% cationic lipid [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 45% cationic lipid [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 10% compound 1 (cationic lipid) [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 20% compound 1 (cationic lipid) [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 30% compound 1 (cationic lipid) [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 40% compound 1 (cationic lipid) [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 45% compound 1 (cationic lipid) [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 10% cholesterol [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 20% cholesterol [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 30% cholesterol [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 40% cholesterol [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 44% cholesterol [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 1% DSPC [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 2% DSPC [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 5% DSPC [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 7.5% DSPC [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 9% DSPC [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 1% PEG [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 2% PEG [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 1% cDSA-PEG [molar ratios].

In one aspect, the disclosure pertains to a composition comprising a RNAi agent comprising a first strand and a second strand, wherein the sequence of the first strand is or comprises the sequence of SEQ ID NO: 300 or nt 1-19 of SEQ ID NO: 300, and/or the sequence of the second strand is or comprises the sequence of SEQ ID NO: 301 or nt 1-19 of SEQ ID NO: 301, wherein the first and/or second strand are modified or not modified, and wherein the composition further comprises at least about 2% cDSA-PEG [molar ratios].

Any of the recited amounts of components (compound 1, cationic lipid, cholesterol, DSPC, PEG, etc.) can be mixed/matched or combined, provided they are not mutually exclusive, in various other aspects of the disclosure.

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified.

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 10% compound 1 (cationic lipid) [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 20% compound 1 (cationic lipid) [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 30% compound 1 (cationic lipid) [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 40% compound 1 (cationic lipid) [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 45% compound 1 (cationic lipid) [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 10% cationic lipid [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 20% cationic lipid [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 30% cationic lipid [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 40% cationic lipid [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 45% cationic lipid [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 10% cholesterol [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 20% cholesterol [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 30% cholesterol [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 40% cholesterol [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 44% cholesterol [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 1% DSPC [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 2% DSPC [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 5% DSPC [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 7.5% DSPC [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 9% DSPC [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 1% PEG [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 2% PEG [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 1% cDSA-PEG [molar ratios].

In one aspect, the disclosure pertains to a composition comprising a RNAi agent comprising a first strand and a second strand, wherein the sequence of the first strand is or comprises the sequence of SEQ ID NO: 302 or nt 1-19 of SEQ ID NO: 302, and/or the sequence of the second strand is or comprises the sequence of SEQ ID NO: 305 or nt 1-19 of SEQ ID NO: 305, wherein the first and/or second strand are modified or not modified, and wherein the composition further comprises at least about 2% cDSA-PEG [molar ratios].

Any of the recited amounts of components (compound 1, cationic lipid, cholesterol, DSPC, PEG, etc.) can be mixed/matched or combined, provided they are not mutually exclusive, in various other aspects of the disclosure.

Additional Pharmaceutical Compositions

In various aspects, the RNAi agent to EPAS1 is packaged as a monotherapy into a delivery vehicle, or may be further ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

The RNAi agents of the present disclosure can be prepared in a pharmaceutical composition comprising various components appropriate for the particular method of administration of the RNAi agent.

Particular Specific Aspects

In a particular specific aspect, the present disclosure is a composition comprising one or more EPAS1 RNAi agents.

In various aspects, the disclosure encompasses a composition comprising any one or more of the following:

A RNAi agent comprising a first and a second strand, wherein the sequence of the first strand is the sequence of SEQ ID NO: 39, and the sequence of the second strand is the sequence of SEQ ID NO: 58, or modified or unmodified variants thereof.

A RNAi agent comprising a first and a second strand, wherein the sequence of the first strand is the sequence of SEQ ID NO: 40, and the sequence of the second strand is the sequence of SEQ ID NO: 59, or modified or unmodified variants thereof.

A RNAi agent comprising a first and a second strand, wherein the sequence of the first strand is the sequence of SEQ ID NO: 41, and the sequence of the second strand is the sequence of SEQ ID NO: 60, or modified or unmodified variants thereof.

A RNAi agent comprising a first and a second strand, wherein the sequence of the first strand is the sequence of SEQ ID NO: 42, and the sequence of the second strand is the sequence of SEQ ID NO: 61, or modified or unmodified variants thereof.

A RNAi agent comprising a first and a second strand, wherein the sequence of the first strand is the sequence of SEQ ID NO: 43, and the sequence of the second strand is the sequence of SEQ ID NO: 62, or modified or unmodified variants thereof.

A RNAi agent comprising a first and a second strand, wherein the sequence of the first strand is the sequence of SEQ ID NO: 44, and the sequence of the second strand is the sequence of SEQ ID NO: 63, or modified or unmodified variants thereof.

A RNAi agent comprising a first and a second strand, wherein the sequence of the first strand is the sequence of SEQ ID NO: 45, and the sequence of the second strand is the sequence of SEQ ID NO: 64, or modified or unmodified variants thereof.

A RNAi agent comprising a first and a second strand, wherein the sequence of the first strand is the sequence of SEQ ID NO: 46, and the sequence of the second strand is the sequence of SEQ ID NO: 65, or modified or unmodified variants thereof.

A RNAi agent comprising a first and a second strand, wherein the sequence of the first strand is the sequence of SEQ ID NO: 47, and the sequence of the second strand is the sequence of SEQ ID NO: 66, or modified or unmodified variants thereof.

A RNAi agent comprising a first and a second strand, wherein the sequence of the first strand is the sequence of SEQ ID NO: 48, and the sequence of the second strand is the sequence of SEQ ID NO: 67, or modified or unmodified variants thereof.

A RNAi agent comprising a first and a second strand, wherein the sequence of the first strand is the sequence of SEQ ID NO: 48, and the sequence of the second strand is the sequence of SEQ ID NO: 67, wherein the sequence of the first and/or second strand further comprises a 3' terminal dinucleotide, or modified or unmodified variants of the RNAi agent.

A RNAi agent comprising a first and a second strand, wherein the sequence of the first strand is the sequence of SEQ ID NO: 48, and the sequence of the second strand is the sequence of SEQ ID NO: 67, wherein the sequence of the first and/or second strand further comprises a 3' terminal dinucleotide selected from TT, UU, U (2'-OMe) dT, U (2'-OMe) U (2'-OMe), T(2'-OMe) T (2'-OMe), T(2'-OMe) dT, dTdT, sdT, dTsdT, sdTsdT, and sdTdT, or modified or unmodified variants of the RNAi agent.

A RNAi agent comprising a first and a second strand, wherein the sequence of the first strand is the sequence of SEQ ID NO: 48, and the sequence of the second strand is the sequence of SEQ ID NO: 67, wherein the sequence of the first and/or second strand further comprises a 3' UU terminal dinucleotide, or modified or unmodified variants of the RNAi agent.

A RNAi agent comprising a first and a second strand, wherein the sequence of the first strand is the sequence of SEQ ID NO: 49, and the sequence of the second strand is the sequence of SEQ ID NO: 68, or modified or unmodified variants thereof.

A RNAi agent comprising a first and a second strand, wherein the sequence of the first strand is the sequence of SEQ ID NO: 50, and the sequence of the second strand is the sequence of SEQ ID NO: 69, or modified or unmodified variants thereof.

A RNAi agent comprising a first and a second strand, wherein the sequence of the first strand is the sequence of SEQ ID NO: 51, and the sequence of the second strand is the sequence of SEQ ID NO: 70, or modified or unmodified variants thereof.

A RNAi agent comprising a first and a second strand, wherein the sequence of the first strand is the sequence of SEQ ID NO: 51, and the sequence of the second strand is the sequence of SEQ ID NO: 70, wherein the sequence of the first and/or second strand further comprises a 3' terminal dinucleotide, or modified or unmodified variants of the RNAi agent.

A RNAi agent comprising a first and a second strand, wherein the sequence of the first strand is the sequence of SEQ ID NO: 51, and the sequence of the second strand is the sequence of SEQ ID NO: 70, wherein the sequence of the first and/or second strand further comprises a 3' terminal dinucleotide selected from TT, UU, U (2'-OMe) dT, U (2'-OMe) U (2'-OMe), T(2'-OMe) T (2'-OMe), T(2'-OMe) dT, dTdT, sdT, dTsdT, sdTsdT, and sdTdT, or modified or unmodified variants of the RNAi agent.

A RNAi agent comprising a first and a second strand, wherein the sequence of the first strand is the sequence of SEQ ID NO: 51, and the sequence of the second strand is the sequence of SEQ ID NO: 70, wherein the sequence of the first and/or second strand further comprises a 3' UU terminal dinucleotide, or modified or unmodified variants of the RNAi agent.

A RNAi agent comprising a first and a second strand, wherein the sequence of the first strand is the sequence of SEQ ID NO: 52, and the sequence of the second strand is the sequence of SEQ ID NO: 71, or modified or unmodified variants thereof.

A RNAi agent comprising a first and a second strand, wherein the sequence of the first strand is the sequence of SEQ ID NO: 53, and the sequence of the second strand is the sequence of SEQ ID NO: 72, or modified or unmodified variants thereof.

A RNAi agent comprising a first and a second strand, wherein the sequence of the first strand is the sequence of SEQ ID NO: 54, and the sequence of the second strand is the sequence of SEQ ID NO: 73, or modified or unmodified variants thereof.

A RNAi agent comprising a first and a second strand, wherein the sequence of the first strand is the sequence of SEQ ID NO: 55, and the sequence of the second strand is the sequence of SEQ ID NO: 74, or modified or unmodified variants thereof.

A RNAi agent comprising a first and a second strand, wherein the sequence of the first strand is the sequence of SEQ ID NO: 56, and the sequence of the second strand is the sequence of SEQ ID NO: 75, or modified or unmodified variants thereof.

A RNAi agent comprising a first and a second strand, wherein the sequence of the first strand is the sequence of SEQ ID NO: 57, and the sequence of the second strand is the sequence of SEQ ID NO: 76, or modified or unmodified variants thereof.

When reference is made herein to a RNAi wherein the sequence of one strand “is”the sequence of a recited SEQ ID NO., the reference indicates that the sequence of the one strand “consists of” the sequence of the recited SEQ ID NO.

Additional Particular Specific Aspects

In a particular specific aspect, the present disclosure is a composition comprising one or more EPAS1 RNAi agents.

In various aspects, the disclosure encompasses a composition comprising any one or more of the following:

Additional Particular Specific Aspects

In a particular specific aspect, the present disclosure is a composition comprising one or more EPAS1 RNAi agents.

In various aspects, the disclosure encompasses a composition comprising any one or more of the following:

A RNAi agent comprising a first and a second strand, wherein the sequence of the first strand is the sequence of SEQ ID NO: 39, or modified or unmodified variants thereof.

A RNAi agent comprising a first and a second strand, wherein the sequence of the first strand is the sequence of SEQ ID NO: 40, or modified or unmodified variants thereof.

A RNAi agent comprising a first and a second strand, wherein the sequence of the first strand is the sequence of SEQ ID NO: 41, or modified or unmodified variants thereof.

A RNAi agent comprising a first and a second strand, wherein the sequence of the first strand is the sequence of SEQ ID NO: 42, or modified or unmodified variants thereof.

A RNAi agent comprising a first and a second strand, wherein the sequence of the first strand is the sequence of SEQ ID NO: 43, or modified or unmodified variants thereof.

A RNAi agent comprising a first and a second strand, wherein the sequence of the first strand is the sequence of SEQ ID NO: 44, or modified or unmodified variants thereof.

A RNAi agent comprising a first and a second strand, wherein the sequence of the first strand is the sequence of SEQ ID NO: 45, or modified or unmodified variants thereof.

A RNAi agent comprising a first and a second strand, wherein the sequence of the first strand is the sequence of SEQ ID NO: 46, or modified or unmodified variants thereof.

A RNAi agent comprising a first and a second strand, wherein the sequence of the first strand is the sequence of SEQ ID NO: 47, or modified or unmodified variants thereof.

A RNAi agent comprising a first and a second strand, wherein the sequence of the first strand is the sequence of SEQ ID NO: 48, or modified or unmodified variants thereof.

A RNAi agent comprising a first and a second strand, wherein the sequence of the first strand is the sequence of SEQ ID NO: 48, wherein the sequence of the strand further comprises a 3' terminal dinucleotide, or modified or unmodified variants of the RNAi agent.

A RNAi agent comprising a first and a second strand, wherein the sequence of the first strand is the sequence of SEQ ID NO: 48, wherein the sequence of the strand further comprises a 3' terminal dinucleotide selected from TT, UU, U (2'-OMe) dT, U (2'-OMe) U (2'-OMe), T(2'-OMe) T (2'-OMe), T(2'-OMe) dT, dTdT, sdT, dTsdT, sdTsdT, and sdTdT, or modified or unmodified variants of the RNAi agent.

A RNAi agent comprising a first and a second strand, wherein the sequence of the first strand is the sequence of SEQ ID NO: 48, wherein the sequence of the strand further comprises a 3' terminal UU dinucleotide, or modified or unmodified variants of the RNAi agent.

A RNAi agent comprising a first and a second strand, wherein the sequence of the first strand is the sequence of SEQ ID NO: 49, or modified or unmodified variants thereof.

A RNAi agent comprising a first and a second strand, wherein the sequence of the first strand is the sequence of SEQ ID NO: 50, or modified or unmodified variants thereof.

A RNAi agent comprising a first and a second strand, wherein the sequence of the first strand is the sequence of SEQ ID NO: 51, or modified or unmodified variants thereof.

A RNAi agent comprising a first and a second strand, wherein the sequence of the first strand is the sequence of SEQ ID NO: 51, wherein the sequence of the first strand further comprises a 3' terminal dinucleotide, or modified or unmodified variants of the RNAi agent.

A RNAi agent comprising a first and a second strand, wherein the sequence of the first strand is the sequence of SEQ ID NO: 51, wherein the sequence of the strand further comprises a 3' terminal dinucleotide selected from TT, UU, U (2'-OMe) dT, U (2'-OMe) U (2'-OMe), T(2'-OMe) T (2'-OMe), T(2'-OMe) dT, dTdT, sdT, dTsdT, sdTsdT, and sdTdT, or modified or unmodified variants of the RNAi agent.

A RNAi agent comprising a first and a second strand, wherein the sequence of the first strand is the sequence of SEQ ID NO: 51, wherein the sequence of the strand further comprises a 3' UU terminal dinucleotide, or modified or unmodified variants of the RNAi agent.

A RNAi agent comprising a first and a second strand, wherein the sequence of the first strand is the sequence of SEQ ID NO: 52, or modified or unmodified variants thereof.

A RNAi agent comprising a first and a second strand, wherein the sequence of the first strand is the sequence of SEQ ID NO: 53, or modified or unmodified variants thereof.

A RNAi agent comprising a first and a second strand, wherein the sequence of the first strand is the sequence of SEQ ID NO: 54, or modified or unmodified variants thereof.

A RNAi agent comprising a first and a second strand, wherein the sequence of the first strand is the sequence of SEQ ID NO: 55, or modified or unmodified variants thereof.

A RNAi agent comprising a first and a second strand, wherein the sequence of the first strand is the sequence of SEQ ID NO: 56, or modified or unmodified variants thereof.

A RNAi agent comprising a first and a second strand, wherein the sequence of the first strand is the sequence of SEQ ID NO: 57, or modified or unmodified variants thereof.

A RNAi agent comprising a first and a second strand, wherein the sequence of the first strand is the sequence of SEQ ID NO: 58, or modified or unmodified variants thereof.

A RNAi agent comprising a first and a second strand, wherein the sequence of the first strand is the sequence of SEQ ID NO: 59, or modified or unmodified variants thereof.

A RNAi agent comprising a first and a second strand, wherein the sequence of the first strand is the sequence of SEQ ID NO: 60, or modified or unmodified variants thereof.

A RNAi agent comprising a first and a second strand, wherein the sequence of the first strand is the sequence of SEQ ID NO: 61, or modified or unmodified variants thereof.

A RNAi agent comprising a first and a second strand, wherein the sequence of the first strand is the sequence of SEQ ID NO: 62, or modified or unmodified variants thereof.

A RNAi agent comprising a first and a second strand, wherein the sequence of the first strand is the sequence of SEQ ID NO: 63, or modified or unmodified variants thereof.

A RNAi agent comprising a first and a second strand, wherein the sequence of the first strand is the sequence of SEQ ID NO: 64, or modified or unmodified variants thereof.

A RNAi agent comprising a first and a second strand, wherein the sequence of the first strand is the sequence of SEQ ID NO: 65, or modified or unmodified variants thereof.

A RNAi agent comprising a first and a second strand, wherein the sequence of the first strand is the sequence of SEQ ID NO: 66, or modified or unmodified variants thereof.

A RNAi agent comprising a first and a second strand, wherein the sequence of the first strand is the sequence of SEQ ID NO: 67, or modified or unmodified variants thereof.

A RNAi agent comprising a first and a second strand, wherein the sequence of the first strand is the sequence of SEQ ID NO: 67, wherein the sequence of the strand further comprises a 3' terminal dinucleotide, or modified or unmodified variants of the RNAi agent.

A RNAi agent comprising a first and a second strand, wherein the sequence of the first strand is the sequence of SEQ ID NO: 67, wherein the sequence of the strand further comprises a 3' terminal dinucleotide selected from TT, UU, U (2'-OMe) dT, U (2'-OMe) U (2'-OMe), T(2'-OMe) T (2'-OMe), T(2'-OMe) dT, dTdT, sdT, dTsdT, sdTsdT, and sdTdT, or modified or unmodified variants of the RNAi agent.

A RNAi agent comprising a first and a second strand, wherein the sequence of the first strand is the sequence of SEQ ID NO: 67, wherein the sequence of the strand further comprises a 3' terminal UU dinucleotide, or modified or unmodified variants of the RNAi agent.

A RNAi agent comprising a first and a second strand, wherein the sequence of the first strand is the sequence of SEQ ID NO: 68, or modified or unmodified variants thereof.

A RNAi agent comprising a first and a second strand, wherein the sequence of the first strand is the sequence of SEQ ID NO: 69, or modified or unmodified variants thereof.

A RNAi agent comprising a first and a second strand, wherein the sequence of the first strand is the sequence of SEQ ID NO: 70, or modified or unmodified variants thereof.

A RNAi agent comprising a first and a second strand, wherein the sequence of the first strand is the sequence of SEQ ID NO: 70, wherein the sequence of the strand further comprises a 3' terminal dinucleotide, or modified or unmodified variants of the RNAi agent.

A RNAi agent comprising a first and a second strand, wherein the sequence of the first strand is the sequence of SEQ ID NO: 70, wherein the sequence of the strand further comprises a 3' terminal dinucleotide selected from TT, UU, U (2'-OMe) dT, U (2'-OMe) U (2'-OMe), T(2'-OMe) T (2'-OMe), T(2'-OMe) dT, dTdT, sdT, dTsdT, sdTsdT, and sdTdT, or modified or unmodified variants of the RNAi agent.

A RNAi agent comprising a first and a second strand, wherein the sequence of the first strand is the sequence of SEQ ID NO: 70, wherein the sequence of the strand further comprises a 3' terminal UU dinucleotide, or modified or unmodified variants of the RNAi agent.

A RNAi agent comprising a first and a second strand, wherein the sequence of the first strand is the sequence of SEQ ID NO: 71, or modified or unmodified variants thereof.

A RNAi agent comprising a first and a second strand, wherein the sequence of the first strand is the sequence of SEQ ID NO: 72, or modified or unmodified variants thereof.

A RNAi agent comprising a first and a second strand, wherein the sequence of the first strand is the sequence of SEQ ID NO: 73, or modified or unmodified variants thereof.

A RNAi agent comprising a first and a second strand, wherein the sequence of the first strand is the sequence of SEQ ID NO: 74, or modified or unmodified variants thereof.

A RNAi agent comprising a first and a second strand, wherein the sequence of the first strand is the sequence of SEQ ID NO: 75, or modified or unmodified variants thereof.

A RNAi agent comprising a first and a second strand, wherein the sequence of the first strand is the sequence of SEQ ID NO: 76, or modified or unmodified variants thereof.

When reference is made herein to a RNAi wherein the sequence of one strand "is"the sequence of a recited SEQ ID NO., the reference indicates that the sequence of the one strand "consists of" the sequence of the recited SEQ ID NO.

Additional Particular Specific Aspects

In various aspects, the disclosure comprises a RNAi agent comprising a first and a second strand, wherein the sequence of the first strand comprises at least 15 contiguous nucleotides differing by 0, 1, 2, or 3 nt from a first strand, and/or the sequence of the second strand comprises at least 15 contiguous nucleotides differing by 0, 1, 2, or 3 nt from the second strand of any one or more RNAi agent disclosed herein.

In various aspects, the disclosure encompasses a composition comprising any one or more of the following:

A RNAi agent comprising a first and a second strand, wherein the sequence of the first strand comprises at least 15 contiguous nucleotides differing by 0, 1, 2, or 3 nt from the sequence of SEQ ID NO: 39, and/or the sequence of the second strand comprises at least 15 contiguous nucleotides differing by 0, 1, 2, or 3 nt from the sequence of SEQ ID NO: 58, wherein the length of the first and second strand are each no more than about 30 nt, or modified or unmodified variants thereof.

A RNAi agent comprising a first and a second strand, wherein the sequence of the first strand comprises at least 15 contiguous nucleotides differing by 0, 1, 2, or 3 nt from the sequence of SEQ ID NO: 40, and/or the sequence of the second strand comprises at least 15 contiguous nucleotides differing by 0, 1, 2, or 3 nt from the sequence of SEQ ID NO: 59, wherein the length of the first and second strand are each no more than about 30 nt, or modified or unmodified variants thereof.

A RNAi agent comprising a first and a second strand, wherein the sequence of the first strand comprises at least 15 contiguous nucleotides differing by 0, 1, 2, or 3 nt from the sequence of SEQ ID NO: 41, and/or the sequence of the second strand comprises at least 15 contiguous nucleotides differing by 0, 1, 2, or 3 nt from the sequence of SEQ ID NO: 60, wherein the length of the first and second strand are each no more than about 30 nt, or modified or unmodified variants thereof.

A RNAi agent comprising a first and a second strand, wherein the sequence of the first strand comprises at least 15 contiguous nucleotides differing by 0, 1, 2, or 3 nt from the sequence of SEQ ID NO: 42, and/or the sequence of the second strand comprises at least 15 contiguous nucleotides differing by 0, 1, 2, or 3 nt from the sequence of SEQ ID NO: 61, wherein the length of the first and second strand are each no more than about 30 nt, or modified or unmodified variants thereof.

A RNAi agent comprising a first and a second strand, wherein the sequence of the first strand comprises at least 15 contiguous nucleotides differing by 0, 1, 2, or 3 nt from the sequence of SEQ ID NO: 43, and/or the sequence of the second strand comprises at least 15 contiguous nucleotides differing by 0, 1, 2, or 3 nt from the sequence of SEQ ID NO: 62, wherein the length of the first and second strand are each no more than about 30 nt, or modified or unmodified variants thereof.

A RNAi agent comprising a first and a second strand, wherein the sequence of the first strand comprises at least 15 contiguous nucleotides differing by 0, 1, 2, or 3 nt from the sequence of SEQ ID NO: 44, and/or the sequence of the second strand comprises at least 15 contiguous nucleotides differing by 0, 1, 2, or 3 nt from the sequence of SEQ ID NO: 63, wherein the length of the first and second strand are each no more than about 30 nt, or modified or unmodified variants thereof.

A RNAi agent comprising a first and a second strand, wherein the sequence of the first strand comprises at least 15 contiguous nucleotides differing by 0, 1, 2, or 3 nt from the sequence of SEQ ID NO: 45, and/or the sequence of the second strand comprises at least 15 contiguous nucleotides differing by 0, 1, 2, or 3 nt from the sequence of SEQ ID NO: 64, wherein the length of the first and second strand are each no more than about 30 nt, or modified or unmodified variants thereof.

A RNAi agent comprising a first and a second strand, wherein the sequence of the first strand comprises at least 15 contiguous nucleotides differing by 0, 1, 2, or 3 nt from the sequence of SEQ ID NO: 46, and/or the sequence of the second strand comprises at least 15 contiguous nucleotides differing by 0, 1, 2, or 3 nt from the sequence of SEQ ID NO: 65, wherein the length of the first and second strand are each no more than about 30 nt, or modified or unmodified variants thereof.

A RNAi agent comprising a first and a second strand, wherein the sequence of the first strand comprises at least 15 contiguous nucleotides differing by 0, 1, 2, or 3 nt from the sequence of SEQ ID NO: 47, and/or the sequence of the second strand comprises at least 15 contiguous nucleotides differing by 0, 1, 2, or 3 nt from the sequence of SEQ ID NO: 66, wherein the length of the first and second strand are each no more than about 30 nt, or modified or unmodified variants thereof.

A RNAi agent comprising a first and a second strand, wherein the sequence of the first strand comprises at least 15 contiguous nucleotides differing by 0, 1, 2, or 3 nt from the sequence of SEQ ID NO: 48, and/or the sequence of the second strand comprises at least 15 contiguous nucleotides differing by 0, 1, 2, or 3 nt from the sequence of SEQ ID NO: 67, wherein the length of the first and second strand are each no more than about 30 nt, or modified or unmodified variants thereof.

A RNAi agent comprising a first and a second strand, wherein the sequence of the first strand comprises at least 15 contiguous nucleotides differing by 0, 1, 2, or 3 nt from the sequence of SEQ ID NO: 49, and/or the sequence of the second strand comprises at least 15 contiguous nucleotides differing by 0, 1, 2, or 3 nt from the sequence of SEQ ID NO: 68, wherein the length of the first and second strand are each no more than about 30 nt, or modified or unmodified variants thereof.

A RNAi agent comprising a first and a second strand, wherein the sequence of the first strand comprises at least 15 contiguous nucleotides differing by 0, 1, 2, or 3 nt from the sequence of SEQ ID NO: 50, and/or the sequence of the second strand comprises at least 15 contiguous nucleotides differing by 0, 1, 2, or 3 nt from the sequence of SEQ ID NO: 69, wherein the length of the first and second strand are each no more than about 30 nt, or modified or unmodified variants thereof.

A RNAi agent comprising a first and a second strand, wherein the sequence of the first strand comprises at least 15 contiguous nucleotides differing by 0, 1, 2, or 3 nt from the sequence of SEQ ID NO: 51, and/or the sequence of the second strand comprises at least 15 contiguous nucleotides differing by 0, 1, 2, or 3 nt from the sequence of SEQ ID NO: 70, wherein the length of the first and second strand are each no more than about 30 nt, or modified or unmodified variants thereof.

A RNAi agent comprising a first and a second strand, wherein the sequence of the first strand comprises at least 15 contiguous nucleotides differing by 0, 1, 2, or 3 nt from the sequence of SEQ ID NO: 52, and/or the sequence of the second strand comprises at least 15 contiguous nucleotides differing by 0, 1, 2, or 3 nt from the sequence of SEQ ID NO: 71, wherein the length of the first and second strand are each no more than about 30 nt, or modified or unmodified variants thereof.

A RNAi agent comprising a first and a second strand, wherein the sequence of the first strand comprises at least 15 contiguous nucleotides differing by 0, 1, 2, or 3 nt from the sequence of SEQ ID NO: 53, and/or the sequence of the second strand comprises at least 15 contiguous nucleotides differing by 0, 1, 2, or 3 nt from the sequence of SEQ ID NO: 72, wherein the length of the first and second strand are each no more than about 30 nt, or modified or unmodified variants thereof.

A RNAi agent comprising a first and a second strand, wherein the sequence of the first strand comprises at least 15 contiguous nucleotides differing by 0, 1, 2, or 3 nt from the sequence of SEQ ID NO: 54, and/or the sequence of the second strand comprises at least 15 contiguous nucleotides differing by 0, 1, 2, or 3 nt from the sequence of SEQ ID NO: 73, wherein the length of the first and second strand are each no more than about 30 nt, or modified or unmodified variants thereof.

A RNAi agent comprising a first and a second strand, wherein the sequence of the first strand comprises at least 15 contiguous nucleotides differing by 0, 1, 2, or 3 nt from the sequence of SEQ ID NO: 55, and/or the sequence of the second strand comprises at least 15 contiguous nucleotides differing by 0, 1, 2, or 3 nt from the sequence of SEQ ID NO: 74, wherein the length of the first and second strand are each no more than about 30 nt, or modified or unmodified variants thereof.

A RNAi agent comprising a first and a second strand, wherein the sequence of the first strand comprises at least 15 contiguous nucleotides differing by 0, 1, 2, or 3 nt from the sequence of SEQ ID NO: 56, and/or the sequence of the second strand comprises at least 15 contiguous nucleotides differing by 0, 1, 2, or 3 nt from the sequence of SEQ ID NO: 75, wherein the length of the first and second strand are each no more than about 30 nt, or modified or unmodified variants thereof.

A RNAi agent comprising a first and a second strand, wherein the sequence of the first strand comprises at least 15 contiguous nucleotides differing by 0, 1, 2, or 3 nt from the sequence of SEQ ID NO: 57, and/or the sequence of the second strand comprises at least 15 contiguous nucleotides differing by 0, 1, 2, or 3 nt from the sequence of SEQ ID NO: 76, wherein the length of the first and second strand are each no more than about 30 nt, or modified or unmodified variants thereof.

Additional Particular Specific Aspects

In various aspects, the disclosure comprises a RNAi agent comprising a first and a second strand, wherein the sequence of the first strand comprises at least 15 contiguous nucleotides of a first strand, and/or the sequence of the second strand comprises at least 15 contiguous nucleotides of the second strand of any one or more RNAi agent disclosed herein.

In various aspects, the disclosure encompasses a composition comprising any one or more of the following:

A RNAi agent comprising a first and a second strand, wherein the sequence of the first strand comprises at least 15 contiguous nucleotides of the sequence of SEQ ID NO: 39, and/or the sequence of the second strand comprises at least 15 contiguous nucleotides of the sequence of SEQ ID NO: 58, wherein the length of the first and second strand are each no more than about 30 nt, or modified or unmodified variants thereof.

A RNAi agent comprising a first and a second strand, wherein the sequence of the first strand comprises at least 15 contiguous nucleotides of the sequence of SEQ ID NO: 40, and/or the sequence of the second strand comprises at least 15 contiguous nucleotides of the sequence of SEQ ID NO: 59, wherein the length of the first and second strand are each no more than about 30 nt, or modified or unmodified variants thereof.

A RNAi agent comprising a first and a second strand, wherein the sequence of the first strand comprises at least 15 contiguous nucleotides of the sequence of SEQ ID NO: 41, and/or the sequence of the second strand comprises at least 15 contiguous nucleotides of the sequence of SEQ ID NO: 60, wherein the length of the first and second strand are each no more than about 30 nt, or modified or unmodified variants thereof.

A RNAi agent comprising a first and a second strand, wherein the sequence of the first strand comprises at least 15 contiguous nucleotides of the sequence of SEQ ID NO: 42, and/or the sequence of the second strand comprises at least 15 contiguous nucleotides of the sequence of SEQ ID NO: 61, wherein the length of the first and second strand are each no more than about 30 nt, or modified or unmodified variants thereof.

A RNAi agent comprising a first and a second strand, wherein the sequence of the first strand comprises at least 15 contiguous nucleotides of the sequence of SEQ ID NO: 43, and/or the sequence of the second strand comprises at least 15 contiguous nucleotides of the sequence of SEQ ID NO: 62, wherein the length of the first and second strand are each no more than about 30 nt, or modified or unmodified variants thereof.

A RNAi agent comprising a first and a second strand, wherein the sequence of the first strand comprises at least 15 contiguous nucleotides of the sequence of SEQ ID NO: 44, and/or the sequence of the second strand comprises at least 15 contiguous nucleotides of the sequence of SEQ ID NO: 63, wherein the length of the first and second strand are each no more than about 30 nt, or modified or unmodified variants thereof.

A RNAi agent comprising a first and a second strand, wherein the sequence of the first strand comprises at least 15 contiguous nucleotides of the sequence of SEQ ID NO: 45, and/or the sequence of the second strand comprises at least 15 contiguous nucleotides of the sequence of SEQ ID NO:

64, wherein the length of the first and second strand are each no more than about 30 nt, or modified or unmodified variants thereof.

A RNAi agent comprising a first and a second strand, wherein the sequence of the first strand comprises at least 15 contiguous nucleotides of the sequence of SEQ ID NO: 46, and/or the sequence of the second strand comprises at least 15 contiguous nucleotides of the sequence of SEQ ID NO: 65, wherein the length of the first and second strand are each no more than about 30 nt, or modified or unmodified variants thereof.

A RNAi agent comprising a first and a second strand, wherein the sequence of the first strand comprises at least 15 contiguous nucleotides of the sequence of SEQ ID NO: 47, and/or the sequence of the second strand comprises at least 15 contiguous nucleotides of the sequence of SEQ ID NO: 66, wherein the length of the first and second strand are each no more than about 30 nt, or modified or unmodified variants thereof.

A RNAi agent comprising a first and a second strand, wherein the sequence of the first strand comprises at least 15 contiguous nucleotides of the sequence of SEQ ID NO: 48, and/or the sequence of the second strand comprises at least 15 contiguous nucleotides of the sequence of SEQ ID NO: 67, wherein the length of the first and second strand are each no more than about 30 nt, or modified or unmodified variants thereof.

A RNAi agent comprising a first and a second strand, wherein the sequence of the first strand comprises at least 15 contiguous nucleotides of the sequence of SEQ ID NO: 49, and/or the sequence of the second strand comprises at least 15 contiguous nucleotides of the sequence of SEQ ID NO: 68, wherein the length of the first and second strand are each no more than about 30 nt, or modified or unmodified variants thereof.

A RNAi agent comprising a first and a second strand, wherein the sequence of the first strand comprises at least 15 contiguous nucleotides of the sequence of SEQ ID NO: 50, and/or the sequence of the second strand comprises at least 15 contiguous nucleotides of the sequence of SEQ ID NO: 69, wherein the length of the first and second strand are each no more than about 30 nt, or modified or unmodified variants thereof.

A RNAi agent comprising a first and a second strand, wherein the sequence of the first strand comprises at least 15 contiguous nucleotides of the sequence of SEQ ID NO: 51, and/or the sequence of the second strand comprises at least 15 contiguous nucleotides of the sequence of SEQ ID NO: 70, wherein the length of the first and second strand are each no more than about 30 nt, or modified or unmodified variants thereof.

A RNAi agent comprising a first and a second strand, wherein the sequence of the first strand comprises at least 15 contiguous nucleotides of the sequence of SEQ ID NO: 52, and/or the sequence of the second strand comprises at least 15 contiguous nucleotides of the sequence of SEQ ID NO: 71, wherein the length of the first and second strand are each no more than about 30 nt, or modified or unmodified variants thereof.

A RNAi agent comprising a first and a second strand, wherein the sequence of the first strand comprises at least 15 contiguous nucleotides of the sequence of SEQ ID NO: 53, and/or the sequence of the second strand comprises at least 15 contiguous nucleotides of the sequence of SEQ ID NO: 72, wherein the length of the first and second strand are each no more than about 30 nt, or modified or unmodified variants thereof.

A RNAi agent comprising a first and a second strand, wherein the sequence of the first strand comprises at least 15 contiguous nucleotides of the sequence of SEQ ID NO: 54, and/or the sequence of the second strand comprises at least 15 contiguous nucleotides of the sequence of SEQ ID NO: 73, wherein the length of the first and second strand are each no more than about 30 nt, or modified or unmodified variants thereof.

A RNAi agent comprising a first and a second strand, wherein the sequence of the first strand comprises at least 15 contiguous nucleotides of the sequence of SEQ ID NO: 55, and/or the sequence of the second strand comprises at least 15 contiguous nucleotides of the sequence of SEQ ID NO: 74, wherein the length of the first and second strand are each no more than about 30 nt, or modified or unmodified variants thereof.

A RNAi agent comprising a first and a second strand, wherein the sequence of the first strand comprises at least 15 contiguous nucleotides of the sequence of SEQ ID NO: 56, and/or the sequence of the second strand comprises at least 15 contiguous nucleotides of the sequence of SEQ ID NO: 75, wherein the length of the first and second strand are each no more than about 30 nt, or modified or unmodified variants thereof.

A RNAi agent comprising a first and a second strand, wherein the sequence of the first strand comprises at least 15 contiguous nucleotides of the sequence of SEQ ID NO: 57, and/or the sequence of the second strand comprises at least 15 contiguous nucleotides of the sequence of SEQ ID NO: 76, wherein the length of the first and second strand are each no more than about 30 nt, or modified or unmodified variants thereof.

Additional Particular Specific Aspects

In a particular specific aspect, the present disclosure is a composition comprising one or more EPAS1 RNAi agents.

In various aspects, the disclosure encompasses a composition comprising any one or more of the following:

A RNAi agent comprising a first and a second strand, wherein the sequence of the first strand comprises the sequence of SEQ ID NO: 39, and/or the sequence of the second strand comprises the sequence of SEQ ID NO: 58, wherein the length of the first and second strand are each no more than about 30 nt, or modified or unmodified variants thereof.

A RNAi agent comprising a first and a second strand, wherein the sequence of the first strand comprises the sequence of SEQ ID NO: 40, and/or the sequence of the second strand comprises the sequence of SEQ ID NO: 59, wherein the length of the first and second strand are each no more than about 30 nt, or modified or unmodified variants thereof.

A RNAi agent comprising a first and a second strand, wherein the sequence of the first strand comprises the sequence of SEQ ID NO: 41, and/or the sequence of the second strand comprises the sequence of SEQ ID NO: 60, wherein the length of the first and second strand are each no more than about 30 nt, or modified or unmodified variants thereof.

A RNAi agent comprising a first and a second strand, wherein the sequence of the first strand comprises the sequence of SEQ ID NO: 42, and/or the sequence of the second strand comprises the sequence of SEQ ID NO: 61, wherein the length of the first and second strand are each no more than about 30 nt, or modified or unmodified variants thereof.

A RNAi agent comprising a first and a second strand, wherein the sequence of the first strand comprises the sequence of SEQ ID NO: 43, and/or the sequence of the second strand comprises the sequence of SEQ ID NO: 62, wherein the length of the first and second strand are each no more than about 30 nt, or modified or unmodified variants thereof.

A RNAi agent comprising a first and a second strand, wherein the sequence of the first strand comprises the sequence of SEQ ID NO: 44, and/or the sequence of the second strand comprises the sequence of SEQ ID NO: 63, wherein the length of the first and second strand are each no more than about 30 nt, or modified or unmodified variants thereof.

A RNAi agent comprising a first and a second strand, wherein the sequence of the first strand comprises the sequence of SEQ ID NO: 45, and/or the sequence of the second strand comprises the sequence of SEQ ID NO: 64, wherein the length of the first and second strand are each no more than about 30 nt, or modified or unmodified variants thereof.

A RNAi agent comprising a first and a second strand, wherein the sequence of the first strand comprises the sequence of SEQ ID NO: 46, and/or the sequence of the second strand comprises the sequence of SEQ ID NO: 65, wherein the length of the first and second strand are each no more than about 30 nt, or modified or unmodified variants thereof.

A RNAi agent comprising a first and a second strand, wherein the sequence of the first strand comprises the sequence of SEQ ID NO: 47, and/or the sequence of the second strand comprises the sequence of SEQ ID NO: 66, wherein the length of the first and second strand are each no more than about 30 nt, or modified or unmodified variants thereof.

A RNAi agent comprising a first and a second strand, wherein the sequence of the first strand comprises the sequence of SEQ ID NO: 48, and/or the sequence of the second strand comprises the sequence of SEQ ID NO: 67, wherein the length of the first and second strand are each no more than about 30 nt, or modified or unmodified variants thereof.

A RNAi agent comprising a first and a second strand, wherein the sequence of the first strand comprises the sequence of SEQ ID NO: 49, and/or the sequence of the second strand comprises the sequence of SEQ ID NO: 68, wherein the length of the first and second strand are each no more than about 30 nt, or modified or unmodified variants thereof.

A RNAi agent comprising a first and a second strand, wherein the sequence of the first strand comprises the sequence of SEQ ID NO: 50, and/or the sequence of the second strand comprises the sequence of SEQ ID NO: 69, wherein the length of the first and second strand are each no more than about 30 nt, or modified or unmodified variants thereof.

A RNAi agent comprising a first and a second strand, wherein the sequence of the first strand comprises the sequence of SEQ ID NO: 51, and/or the sequence of the second strand comprises the sequence of SEQ ID NO: 70, wherein the length of the first and second strand are each no more than about 30 nt, or modified or unmodified variants thereof.

A RNAi agent comprising a first and a second strand, wherein the sequence of the first strand comprises the sequence of SEQ ID NO: 52, and/or the sequence of the second strand comprises the sequence of SEQ ID NO: 71, wherein the length of the first and second strand are each no more than about 30 nt, or modified or unmodified variants thereof.

A RNAi agent comprising a first and a second strand, wherein the sequence of the first strand comprises the sequence of SEQ ID NO: 53, and/or the sequence of the second strand comprises the sequence of SEQ ID NO: 72, wherein the length of the first and second strand are each no more than about 30 nt, or modified or unmodified variants thereof.

A RNAi agent comprising a first and a second strand, wherein the sequence of the first strand comprises the sequence of SEQ ID NO: 54, and/or the sequence of the second strand comprises the sequence of SEQ ID NO: 73, wherein the length of the first and second strand are each no more than about 30 nt, or modified or unmodified variants thereof.

A RNAi agent comprising a first and a second strand, wherein the sequence of the first strand comprises the sequence of SEQ ID NO: 55, and/or the sequence of the second strand comprises the sequence of SEQ ID NO: 74, wherein the length of the first and second strand are each no more than about 30 nt, or modified or unmodified variants thereof.

A RNAi agent comprising a first and a second strand, wherein the sequence of the first strand comprises the sequence of SEQ ID NO: 56, and/or the sequence of the second strand comprises the sequence of SEQ ID NO: 75, wherein the length of the first and second strand are each no more than about 30 nt, or modified or unmodified variants thereof.

A RNAi agent comprising a first and a second strand, wherein the sequence of the first strand comprises the sequence of SEQ ID NO: 57, and/or the sequence of the second strand comprises the sequence of SEQ ID NO: 76, wherein the length of the first and second strand are each no more than about 30 nt, or modified or unmodified variants thereof.

Additional Particular Specific Aspects

In a particular specific aspect, the present disclosure is a composition comprising one or more EPAS1 RNAi agents.

In various aspects, the disclosure encompasses a composition comprising any one or more of the following:

A RNAi agent comprising a first and a second strand, wherein the sequence of the first strand comprises the sequence of SEQ ID NO: 39, wherein the length of the first and second strand are each no more than about 30 nt, or modified or unmodified variants thereof.

A RNAi agent comprising a first and a second strand, wherein the sequence of the first strand comprises the sequence of SEQ ID NO: 40, wherein the length of the first and second strand are each no more than about 30 nt, or modified or unmodified variants thereof.

A RNAi agent comprising a first and a second strand, wherein the sequence of the first strand comprises the sequence of SEQ ID NO: 41, wherein the length of the first and second strand are each no more than about 30 nt, or modified or unmodified variants thereof.

A RNAi agent comprising a first and a second strand, wherein the sequence of the first strand comprises the sequence of SEQ ID NO: 42, wherein the length of the first and second strand are each no more than about 30 nt, or modified or unmodified variants thereof.

A RNAi agent comprising a first and a second strand, wherein the sequence of the first strand comprises the sequence of SEQ ID NO: 43, wherein the length of the first and second strand are each no more than about 30 nt, or modified or unmodified variants thereof.

A RNAi agent comprising a first and a second strand, wherein the sequence of the first strand comprises the sequence of SEQ ID NO: 44, wherein the length of the first and second strand are each no more than about 30 nt, or modified or unmodified variants thereof.

A RNAi agent comprising a first and a second strand, wherein the sequence of the first strand comprises the sequence of SEQ ID NO: 45, wherein the length of the first and second strand are each no more than about 30 nt, or modified or unmodified variants thereof.

A RNAi agent comprising a first and a second strand, wherein the sequence of the first strand comprises the sequence of SEQ ID NO: 46, wherein the length of the first and second strand are each no more than about 30 nt, or modified or unmodified variants thereof.

A RNAi agent comprising a first and a second strand, wherein the sequence of the first strand comprises the sequence of SEQ ID NO: 47, wherein the length of the first and second strand are each no more than about 30 nt, or modified or unmodified variants thereof.

A RNAi agent comprising a first and a second strand, wherein the sequence of the first strand comprises the sequence of SEQ ID NO: 48, wherein the length of the first and second strand are each no more than about 30 nt, or modified or unmodified variants thereof.

A RNAi agent comprising a first and a second strand, wherein the sequence of the first strand comprises the sequence of SEQ ID NO: 49, wherein the length of the first and second strand are each no more than about 30 nt, or modified or unmodified variants thereof.

A RNAi agent comprising a first and a second strand, wherein the sequence of the first strand comprises the sequence of SEQ ID NO: 50, wherein the length of the first and second strand are each no more than about 30 nt, or modified or unmodified variants thereof.

A RNAi agent comprising a first and a second strand, wherein the sequence of the first strand comprises the sequence of SEQ ID NO: 51, wherein the length of the first and second strand are each no more than about 30 nt, or modified or unmodified variants thereof.

A RNAi agent comprising a first and a second strand, wherein the sequence of the first strand comprises the sequence of SEQ ID NO: 52, wherein the length of the first and second strand are each no more than about 30 nt, or modified or unmodified variants thereof.

A RNAi agent comprising a first and a second strand, wherein the sequence of the first strand comprises the sequence of SEQ ID NO: 53, wherein the length of the first and second strand are each no more than about 30 nt, or modified or unmodified variants thereof.

A RNAi agent comprising a first and a second strand, wherein the sequence of the first strand comprises the sequence of SEQ ID NO: 54, wherein the length of the first and second strand are each no more than about 30 nt, or modified or unmodified variants thereof.

A RNAi agent comprising a first and a second strand, wherein the sequence of the first strand comprises the sequence of SEQ ID NO: 55, wherein the length of the first and second strand are each no more than about 30 nt, or modified or unmodified variants thereof.

A RNAi agent comprising a first and a second strand, wherein the sequence of the first strand comprises the sequence of SEQ ID NO: 56, wherein the length of the first and second strand are each no more than about 30 nt, or modified or unmodified variants thereof.

A RNAi agent comprising a first and a second strand, wherein the sequence of the first strand comprises the sequence of SEQ ID NO: 57, wherein the length of the first and second strand are each no more than about 30 nt, or modified or unmodified variants thereof.

A RNAi agent comprising a first and a second strand, wherein the sequence of the first strand comprises the sequence of SEQ ID NO: 58, wherein the length of the first and second strand are each no more than about 30 nt, or modified or unmodified variants thereof.

A RNAi agent comprising a first and a second strand, wherein the sequence of the first strand comprises the sequence of SEQ ID NO: 59, wherein the length of the first and second strand are each no more than about 30 nt, or modified or unmodified variants thereof.

A RNAi agent comprising a first and a second strand, wherein the sequence of the first strand comprises the sequence of SEQ ID NO: 60, wherein the length of the first and second strand are each no more than about 30 nt, or modified or unmodified variants thereof.

A RNAi agent comprising a first and a second strand, wherein the sequence of the first strand comprises the sequence of SEQ ID NO: 61, wherein the length of the first and second strand are each no more than about 30 nt, or modified or unmodified variants thereof.

A RNAi agent comprising a first and a second strand, wherein the sequence of the first strand comprises the sequence of SEQ ID NO: 62, wherein the length of the first and second strand are each no more than about 30 nt, or modified or unmodified variants thereof.

A RNAi agent comprising a first and a second strand, wherein the sequence of the first strand comprises the sequence of SEQ ID NO: 63, wherein the length of the first and second strand are each no more than about 30 nt, or modified or unmodified variants thereof.

A RNAi agent comprising a first and a second strand, wherein the sequence of the first strand comprises the sequence of SEQ ID NO: 64, wherein the length of the first and second strand are each no more than about 30 nt, or modified or unmodified variants thereof.

A RNAi agent comprising a first and a second strand, wherein the sequence of the first strand comprises the sequence of SEQ ID NO: 65, wherein the length of the first and second strand are each no more than about 30 nt, or modified or unmodified variants thereof.

A RNAi agent comprising a first and a second strand, wherein the sequence of the first strand comprises the sequence of SEQ ID NO: 66, wherein the length of the first and second strand are each no more than about 30 nt, or modified or unmodified variants thereof.

A RNAi agent comprising a first and a second strand, wherein the sequence of the first strand comprises the sequence of SEQ ID NO: 67, wherein the length of the first and second strand are each no more than about 30 nt, or modified or unmodified variants thereof.

A RNAi agent comprising a first and a second strand, wherein the sequence of the first strand comprises the sequence of SEQ ID NO: 68, wherein the length of the first and second strand are each no more than about 30 nt, or modified or unmodified variants thereof.

A RNAi agent comprising a first and a second strand, wherein the sequence of the first strand comprises the sequence of SEQ ID NO: 69, wherein the length of the first and second strand are each no more than about 30 nt, or modified or unmodified variants thereof.

A RNAi agent comprising a first and a second strand, wherein the sequence of the first strand comprises the sequence of SEQ ID NO: 70, wherein the length of the first and second strand are each no more than about 30 nt, or modified or unmodified variants thereof.

A RNAi agent comprising a first and a second strand, wherein the sequence of the first strand comprises the sequence of SEQ ID NO: 71, wherein the length of the first and second strand are each no more than about 30 nt, or modified or unmodified variants thereof.

A RNAi agent comprising a first and a second strand, wherein the sequence of the first strand comprises the sequence of SEQ ID NO: 72, wherein the length of the first and second strand are each no more than about 30 nt, or modified or unmodified variants thereof.

A RNAi agent comprising a first and a second strand, wherein the sequence of the first strand comprises the sequence of SEQ ID NO: 73, wherein the length of the first and second strand are each no more than about 30 nt, or modified or unmodified variants thereof.

A RNAi agent comprising a first and a second strand, wherein the sequence of the first strand comprises the sequence of SEQ ID NO: 74, wherein the length of the first and second strand are each no more than about 30 nt, or modified or unmodified variants thereof.

A RNAi agent comprising a first and a second strand, wherein the sequence of the first strand comprises the sequence of SEQ ID NO: 75, wherein the length of the first and second strand are each no more than about 30 nt, or modified or unmodified variants thereof.

A RNAi agent comprising a first and a second strand, wherein the sequence of the first strand comprises the sequence of SEQ ID NO: 76, wherein the length of the first and second strand are each no more than about 30 nt, or modified or unmodified variants thereof.

Additional Particular Aspects

In various aspects, the disclosure comprises a RNAi agent comprising a sense and an antisense strand, wherein the antisense strand comprises at least 15 contiguous nucleotides differing by 0, 1, 2, or 3 nt from the antisense strand of any RNAi agent disclosed herein, or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

Thus, in various aspects, the disclosure comprises a RNAi agent comprising a sense and an antisense strand, wherein the antisense strand comprises at least 15 contiguous nucleotides differing by 0, 1, 2, or 3 nt from the antisense strand of any of: SEQ ID NOs: 40 and 59; SEQ ID NOs: 41 and 60; SEQ ID NOs: 42 and 61; SEQ ID NOs: 43 and 62; SEQ ID NOs: 44 and 63; SEQ ID NOs: 45 and 64; SEQ ID NOs: 46 and 65; SEQ ID NOs: 47 and 66; SEQ ID NOs: 48 and 67; SEQ ID NOs: 49 and 68; SEQ ID NOs: 50 and 69; SEQ ID NOs: 51 and 70; SEQ ID NOs: 52 and 71; SEQ ID NOs: 53 and 72; SEQ ID NOs: 54 and 73; SEQ ID NOs: 55 and 74; SEQ ID NOs: 56 and 75; or SEQ ID NOs: 57 and 76, or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

In one aspect, the disclosure comprises any one or more RNAi agent listed herein.

Additional Particular Specific Aspects

Other particular specific aspects include compositions comprising 1, 2, 3, 4, or more of these RNAi agents. Another aspect is a composition comprising any single RNAi agent, along with any other RNAi agents which overlap it. Another aspect comprises two, three, four or more EPAS1 RNAi agents which do not overlap and thus target different parts of the RNA molecule. When two or more RNAi agents are used, they can be administered simultaneously or sequentially.

Another particular specific aspect comprises an RNAi agent, wherein the RNAi agent comprises a sense strand comprising at least 15 contiguous nucleotides (identical in sequence) to the sense strand of any of the listed RNAi agents, and an antisense strand comprising at least 15 contiguous nucleotides (identical in sequence) to the antisense strand of the same RNAi agent. In another aspect, the composition comprises one, two, three, four, or more such RNAi agents.

In one aspect, the composition comprises an RNAi agent which comprises an antisense strand comprising at least 15 contiguous nucleotides differing by 0, 1, 2 or 3 mismatches from the antisense strand of a RNAi agent described herein.

In one aspect, the composition comprises an RNAi agent which comprises an antisense strand comprising at least 15 contiguous nucleotides differing by 0, 1, 2 or 3 mismatches from the antisense strand of a RNAi agent described herein.

In another aspect, the composition comprises an RNAi agent which comprises a sense strand comprising at least 15 contiguous nucleotides differing by 0, 1, 2, or 3 mismatches from the sense strand of one of the listed RNAi agents, and an antisense strand comprising at least 15 contiguous nucleotides differing by 0, 1, 2 or 3 mismatches from the antisense strand of the same RNAi agent.

A "mismatch" is defined herein as a difference between the base sequence or length when two sequences are maximally aligned and compared. As a non-limiting example, a mismatch is counted if a difference exists between the base at a particular location in one sequence and the base at the corresponding position in another sequence (e.g., between the sequence of a given RNAi agent and an RNAi agent listed herein). Thus, a mismatch is counted, for example, if a position in one sequence has a particular base (e.g., A), and the corresponding position on the other sequence has a different base (e.g., G, C or U). A mismatch is also counted, e.g., if a position in one sequence has a base (e.g., A), and the corresponding position on the other sequence has no base (e.g., that position is an abasic nucleotide which comprises a phosphate-sugar backbone but no base). A single-stranded nick in either sequence (or in the sense or antisense strand) is not counted as mismatch. Thus, as a non-limiting example, no mismatch would be counted if one sequence comprises the sequence A-G, but the other sequence comprises the sequence A-G with a single-stranded nick between the A and the G. A base modification is also not considered a mismatch. If one sequence comprises a C, and the other sequence comprises a modified C (e.g., with a 2'-modification) at the same position, no mismatch would be counted. Thus, modifications of a nucleotide other than replacement or alteration of the base would not constitute a mismatch. For example, no mismatch would occur between a nucleotide which is A, and a nucleotide which is A with a 5' modification (e.g., those illustrated in FIG. 1) and/or a 2'-modification. The key feature of a mismatch (base replacement) is that it would not be able to base-pair with the corresponding base on the opposite strand. In addition, terminal overhangs such as "UU" or "dTdT" are not counted when counting the number of mismatches; the terminal "UU" and "dTdT" overhangs are also not included when calculating "15 contiguous nucleotides."

In these aspects, a mismatch is defined as a position wherein the base of one sequence does not match the base of the other sequence.

In another aspect, the composition comprises 1, 2, 3, 4, or more such RNAi agents.

In another aspect, the composition comprises an RNAi agent which comprises a sense strand comprising at least 15 contiguous nucleotides differing by 0, 1, 2 or 3 mismatches from the sense strand of one of the listed RNAi agents, and an antisense strand comprising at least 15 contiguous nucleotides differing by 0, 1, 2 or 3 mismatches from the antisense strand of the same RNAi agent Overlapping Groups of EPAS1 siRNAs In various aspects, the disclosure relates to groups of RNAi agents with overlapping sequences. Thus, the disclosure encompasses groups of RNAi agents wherein each RNAi agent in the group overlaps with each other RNAi agent in the same group by at least 5, 6, 7, 8, 9, 10, 11, 12, 13, 14, 15, 16, 17, 18, 19 or more nucleotides. Particularly, in one aspect, the overlap is at least 12 nt. Groups of sequences that overlap are shown in Table 9 (Example 6), wherein each member of a group overlaps with each other member of the same group by at least 12 nt. A portion of the overlap of the sense strands and a portion of the overlap of the antisense strand are presented. Thus, for example, 3304 and 3310 share the common technical feature of the sequence of UCACUUUAUUAUC (SEQ ID NO: 115) in the sense strand, and the sequence of GAUAAUAAAGUGA (SEQ ID NO: 120) in the antisense strand. Note, of course, that various groupings comprise different numbers of overlapping siRNAs; any two siRNAs within that group overlap. Thus, 5057, 5058 and 5059 all overlap with each other, meaning that any two of that group (5057 and 5059; or 5058 and 5059; or 5058 and 5059) share a common technical feature of an overlapping portion of the sense and/or anti-sense strand sequence. The disclosure thus encompasses any pair or grouping of overlapping siRNAs, wherein the pair share a technical feature, namely, the portion of the sense and/or anti-sense strand which overlaps, as described in Table 9.

The disclosure thus encompasses various aspects comprising groups of overlapping RNAi agents, for example (1) RNAi agents comprising the sequences of 5057 and 5059; or 5058 and 5059; or 5058 and 5059 (or any other pair or group of overlapping RNAi agents); (2) RNAi agents consisting of the sequences of 5057 and 5059; or 5058 and 5059; or 5058 and 5059 (or any other pair or group of overlapping RNAi agents); (3) RNAi agents comprising the sequences of 5057 and 5059; or 5058 and 5059; or 5058 and 5059 (or any other pair or group of overlapping RNAi agents); (4) RNAi agents comprising a sense strand and/or a antisense strand comprising a sequence of 5057 and 5059; or 5058 and 5059; or 5058 and 5059 (or any other pair or group of overlapping RNAi agents); (5) RNAi agents comprising a sense strand and/or a antisense strand comprising 15 contiguous nt with 0 to 3 mismatches from a sequence of 5057 and 5059; or 5058 and 5059; or 5058 and 5059 (or any other pair or group of overlapping RNAi agents); (6) RNAi agents comprising a sense strand comprising 15 contiguous nt with 0 to 3 mismatches from a sequence of 5057 and 5059; or 5058 and 5059; or 5058 and 5059 (or any other pair or group of overlapping RNAi agents); (7) RNAi agents comprising an antisense strand comprising 15 contiguous nt with 0 to 3 mismatches from a sequence of 5057 and 5059; or 5058 and 5059; or 5058 and 5059 (or any other pair or group of overlapping RNAi agents); etc. The disclosure also encompasses similar aspects reflecting all the overlapping groups of RNAi agents as described in Table 9.

Variants of RNAi agents (e.g., comprising different modifications, caps, etc.) are disclosed herein, e.g., in the Tables. An unmodified and an example modified variant of various RNAi agents are provided. The disclosure thus encompasses groups of overlapping modified and/or unmodified RNAi agents. More aspects are provided herein, and are included in the scope of each RNAi agents of the disclosure.

EXAMPLES

Example 1

Bioinformatics

Hundreds of RNAi agents (siRNAs) to EPAS1 were chosen based on several criteria. Some of the criteria (not all of which were met by all selected sequences) include: Human/Cyno cross reactivity; BioPred; siRNAs have U or A at nt 1 (although 2802 and 3739 start with a C); siRNAs exclude seed match to known human microRNA for AS strand; and sequences exclude repeats of 4 or more.

A selection of the most efficacious RNAi agents tested are disclosed herein, and their sequences presented in the Tables. Tables 2 and 3 below present the DNA sequences of the RNAi agents, and the unmodified RNA sequence.

The phrase "Start" denotes the starting position of the oligonucleotide (e.g., the 19-mer) on the transcript. This is measured in nucleotide coordinates, relative to beginning of the transcript.

TABLE 2

EPAS1 19-mers. DNA sequences.

| Position NM_001430 | Sense | SEQ ID NO: | Antisense | SEQ ID NO: |
|---|---|---|---|---|
| 842 | ATGGCGACATGATCTTTCT | 1 | AGAAAGATCATGTCGCCAT | 20 |
| 2802 | AAATGTACCCAATGATAAG | 2 | CTTATCATTGGGTACATTT | 21 |
| 3040 | GAACTGACCAGATATGACT | 3 | AGTCATATCTGGTCAGTTC | 22 |
| 3304 | AGATGCTCACTTTATTATC | 4 | GATAATAAAGTGAGCATCT | 23 |
| 3310 | TCACTTTATTATCCCTATT | 5 | AATAGGGATAATAAAGTGA | 24 |
| 3345 | GTTTTACCTGTTCTGAAAT | 6 | ATTTCAGAACAGGTAAAAC | 25 |
| 3354 | GTTCTGAAATGTTCTTAAA | 7 | TTTAAGAACATTTCAGAAC | 26 |
| 3735 | ACTCCAACGTATGTGGTTA | 8 | TAACCACATACGTTGGAGT | 27 |

TABLE 2-continued

EPAS1 19-mers. DNA sequences.

| Position NM_001430 | Sense | SEQ ID NO: | Antisense | SEQ ID NO: |
|---|---|---|---|---|
| 3739 | CAACGTATGTGGTTATCTG | 9 | CAGATAACCACATACGTTG | 28 |
| 3875 | TGGGTTAAGTGTTTATCAT | 10 | ATGATAAACACTTAACCCA | 29 |
| 4153 | CATTCTCTATGTACTATGT | 11 | ACATAGTACATAGAGAATG | 30 |
| 4157 | CTCTATGTACTATGTATGT | 12 | ACATACATAGTACATAGAG | 31 |
| 5049 | CAACGTAACGATTTCATGA | 13 | TCATGAAATCGTTACGTTG | 32 |
| 5057 | CGATTTCATGAACGTTATT | 14 | AATAACGTTCATGAAATCG | 33 |
| 5058 | GATTTCATGAACGTTATTA | 15 | TAATAACGTTCATGAAATC | 34 |
| 5059 | ATTTCATGAACGTTATTAT | 16 | ATAATAACGTTCATGAAAT | 35 |
| 5108 | CTGTATGGGAGCTTAACTT | 17 | AAGTTAAGCTCCCATACAG | 36 |
| 5144 | TGACACTGGTATCTTATTA | 18 | TAATAAGATACCAGTGTCA | 37 |
| 5149 | CTGGTATCTTATTAAAGTA | 19 | TACTTTAATAAGATACCAG | 38 |

TABLE 3

EPAS1 RNAi agent sequences

| Position NM_001430 | Sense | SEQ ID NO: | Antisense | SEQ ID NO: |
|---|---|---|---|---|
| 842 | AUGGCGACAUGAUCUUUCU | 39 | AGAAAGAUCAUGUCGCCAU | 58 |
| 2802 | AAAUGUACCCAAUGAUAAG | 40 | CUUAUCAUUGGGUACAUUU | 59 |
| 3040 | GAACUGACCAGAUAUGACU | 41 | AGUCAUAUCUGGUCAGUUC | 60 |
| 3304 | AGAUGCUCACUUUAUUAUC | 42 | GAUAAUAAAGUGAGCAUCU | 61 |
| 3310 | UCACUUUAUUAUCCCUAUU | 43 | AAUAGGGAUAAUAAAGUGA | 62 |
| 3345 | GUUUUACCUGUUCUGAAAU | 44 | AUUUCAGAACAGGUAAAAC | 63 |
| 3354 | GUUCUGAAAUGUUCUUAAA | 45 | UUUAAGAACAUUUCAGAAC | 64 |
| 3735 | ACUCCAACGUAUGUGGUUA | 46 | UAACCACAUACGUUGGAGU | 65 |
| 3739 | CAACGUAUGUGGUUAUCUG | 47 | CAGAUAACCACAUACGUUG | 66 |
| 3875 | UGGGUUAAGUGUUUAUCAU | 48 | AUGAUAAACACUUAACCCA | 67 |
| 4153 | CAUUCUCUAUGUACUAUGU | 49 | ACAUAGUACAUAGAGAAUG | 68 |
| 4157 | CUCUAUGUACUAUGUAUGU | 50 | ACAUACAUAGUACAUAGAG | 69 |
| 5049 | CAACGUAACGAUUUCAUGA | 51 | UCAUGAAAUCGUUACGUUG | 70 |
| 5057 | CGAUUUCAUGAACGUUAUU | 52 | AAUAACGUUCAUGAAAUCG | 71 |
| 5058 | GAUUUCAUGAACGUUAUUA | 53 | UAAUAACGUUCAUGAAAUC | 72 |
| 5059 | AUUUCAUGAACGUUAUUAU | 54 | AUAAUAACGUUCAUGAAAU | 73 |
| 5108 | CUGUAUGGGAGCUUAACUU | 55 | AAGUUAAGCUCCCAUACAG | 74 |
| 5144 | UGACACUGGUAUCUUAUUA | 56 | UAAUAAGAUACCAGUGUCA | 75 |
| 5149 | CUGGUAUCUUAUUAAAGUA | 57 | UACUUUAAUAAGAUACCAG | 76 |

All of these sequences are *Homo sapiens* sequences.

As noted above, one of the selection criteria for EPAS1 RNAi agents was cross-reactivity between the human and Cyno sequences. If the sequences are cross-reactive, then the same RNAi agent of the same sequence could be used in both Cyno and human experiments. Table 4 indicates the cross-reactivity of various EPAS1 RNAi agents with mouse (Mu), rat (Ra) and Rhesus [mmu or *Macaca mulatta* endothelial PAS domain protein 1, transcript variant 3 (EPAS1), mRNA].

TABLE 4

Cross-reactivity of EPAS1 RNAi agents.

| Position_ NM_001430 | CMatch-REFSEQ NM_010137 Mu (refseq_ rna_mm) | CMatch-REFSEQ NM_023090 Ra (refseq_ rna_rn) | CMatch-REFSEQ XM_001112947 (refseq_ rna_mmu) |
|---|---|---|---|
| 842 | | | Y |
| 2802 | | | |
| 3040 | Y | Y | Y |
| 3304 | | | Y |
| 3310 | | | Y |
| 3345 | | | Y |
| 3354 | | | Y |
| 3735 | | | Y |
| 3739 | | | Y |
| 3875 | | | Y |
| 4153 | | | |
| 4157 | | | Y |
| 5049 | | | Y |
| 5057 | | | |
| 5058 | | | |
| 5059 | | | |
| 5108 | | | Y |
| 5144 | | | Y |
| 5149 | | | Y |

All the duplexes tested have *Homo sapiens* ("hs") sequences, though for some of these, the sequence also matches that of the corresponding mouse (Mu or mm, Second column), rat (Ra or rrn, Third column) or Rhesus (mmu or *Macaca mulatta*, Fourth column) sequence. A "Y" in the appropriate column and row indicates that this sequence matches between human and the indicated animal. A sequence matching between human and a test animal allows the same sequence to be used in both animal and human testing.

Modifications of the duplexes in Table 3 are easily conceived by one of skill in the art. Example and non-limiting modifications of these duplexes were conceived. These are listed in Table 3. Additional modifications are contemplated.

For the modified variants listed in Table 5, some modifications were placed at sites predicted to be sensitive to endonucleases. Some modifications were designed to eliminate an immune response to the siRNA while preserving activity. In general, the sense strand was heavily modified, and the antisense strand lightly modified. Some modifications serve more than one purpose. Table 3 lists RNAi agents prepared with these modifications. In addition, the modification of addition of a terminal dinucleotide dTdT is provided.

TABLE 5 (comprising TABLES 5A to 5E) list different sets of modified variants of the RNAi agent sequences.

Table 5. EPAS1 RNAi Agents (Example Modified Variants).

Table 5A. EPAS1 RNAi Agents (Example Modified Variants).

Table 5A lists example modified variants with the A51 S26 modifications:

A51: In guide strand all U as 2'-OMe-U and all C as 2'-OMe-C, except pos. 1, 2 and 14; 3' overhangs as 2'-OMe-U 2'-OMe-U S26: In sense strand all U as 2'-OMe-U and all C as 2'-OMe-C; 3' overhangs as 2'-OMe-U 2'-OMe-U "G," "C," "A," "T" and "U" each generally stand for a nucleotide that contains guanine, cytosine, adenine, thymidine and uracil as a base, respectively.

FIG. 1 illustrates various example modified nucleotides which have been or can be used in modified variants of EPAS1 RNAi agents: U002, U003, U004, U005, C004, C005, A004, A005, G005, and G004, which can be used in the RNAi agents disclosed herein. U002 indicates a 2'-deoxy-thymidine which is DNA. U003 indicates 2'-deoxy uridine. U004 indicates a nucleotide with a Uridine ("U") base with a 2'-O-methyl modification. U005 indicates a U base with a 2'-O-methoxyethyl (MOE) modification. C004 indicates a Cytosine ("C") base with a 2'-O-methyl modification. C005 indicates a C base with 2'-O-methoxyethyl modification. A004 indicates an Adenosine ("A") base with a 2'-O-methyl modification. A005 indicates an A base with 2'-O-methoxyethyl modification. G005 indicates a Guanosine ("G") base with a 2'O-methyl modification. G004 indicates a G base with a 2'O-methyl modification.

"p" indicates phosphate.

TABLE 5A

| Position_NM_001430 | MODIFIED_SENSE_SEQUENCE | SEQ ID NO: | MODIFIED_ANTISENSE_SEQUENCE | SEQ ID NO: |
|---|---|---|---|---|
| 842 | A pU004 pG pG pC pG pA pC pA pU004 pG pA pU004 pC pU004 pU004 pU004 pC pU004 pU004 pU004 | 145 | A pG pA pA pA pG pA pU004 pC004 pA pU004 pG pU004 pC pG pC004 pC004 pA pU004 pU004 pU004 | 126 |
| 2802 | A pA pA pU004 pG pU004 pA pC pC pC pA pA pU004 pG pA pU004 pA pA pG pU004 pU004 | 146 | C pU pU004 pA pU004 pC004 pA pU004 pU004 pG pG pG pU004 pA pC004 pA pU004 pU004 pU004 pU004 pU004 | 127 |
| 3040 | G pA pA pC pU004 pG pA pC pC pA pG pA pU004 pA pU004 pG pA pC pU004 pU004 pU004 | 147 | A pG pU004 pC004 pA pU004 pA pU004 pC004 pU004 pG pG pU004 pC pA pG pU004 pU004 pC004 pU004 pU004 | 128 |
| 3304 | A pG pA pU004 pG pC pU004 pC pA pC pU004 pU004 pU004 pA pU004 pU004 pA pU004 pC pU004 pU004 | 148 | G pA pU004 pA pA pU004 pA pA pA pG pU004 pG pA pG pC004 pA pU004 pC004 pU004 pU004 pU004 | 129 |
| 3310 | U004 pC pA pC pU004 pU004 pU004 pA pU004 pU004 pA pU004 pC pC pC pU004 pA pU004 pU004 pU004 pU004 | 149 | A pA pU004 pA pG pG pG pA pU004 pA pA pU004 pA pA pA pG pU004 pG pA pU004 pU004 | 130 |

TABLE 5A-continued

| Position_NM_001430 | MODIFIED_SENSE_SEQUENCE | SEQ ID NO: | MODIFIED_ANTISENSE_SEQUENCE | SEQ ID NO: |
|---|---|---|---|---|
| 3345 | G pU004 pU004 pU004 pU004 pA pC pC pU004 pG pU004 pU004 pC pU004 pG pA pA pA pU004 pU004 pU004 | 150 | A pU pU004 pU004 pC004 pA pG pA pA pC004 pA pG pG pU pA pA pA pA pC004 pU004 pU004 | 131 |
| 3354 | G pU004 pU004 pC pU004 pG pA pA pA pU004 pG pU004 pU004 pC pU004 pU004 pA pA pA pU004 pU004 | 151 | U pU pU004 pA pA pG pA pA pC004 pA pU004 pU004 pU004 pC pA pG pA pA pC004 pU004 pU004 | 132 |
| 3735 | A pC pU004 pC pC pA pA pC pG pU004 pA pU004 pG pU004 pG pG pU004 pU004 pA pU004 pU004 | 152 | U pA pA pC004 pC004 pA pC004 pA pU004 pA pC004 pG pU004 pU pG pG pA pG pU004 pU004 pU004 | 133 |
| 3739 | C pA pA pC pG pU004 pA pU004 pG pU004 pG pG pU004 pU004 pA pU004 pC pU004 pG pU004 pU004 | 153 | C pA pG pA pU004 pA pA pC004 pC004 pA pC004 pA pU004 pA pC004 pG pU004 pU004 pG pU004 pU004 | 134 |
| 3875 | U004 pG pG pG pU004 pU004 pA pA pG pU004 pG pU004 pU004 pU004 pA pU004 pC pA pU004 pU004 pU004 | 154 | A pU pG pA pU004 pA pA pA pC004 pA pC004 pU004 pU004 pA pA pC004 pC004 pC004 pA pU004 pU004 | 135 |
| 4153 | C pA pU004 pU004 pC pU004 pC pU004 pA pU004 pG pU004 pA pC pU004 pA pU004 pG pU004 pU004 pU004 | 155 | A pC pA pU004 pA pG pU004 pA pC004 pA pU004 pA pG pA pG pA pA pU004 pG pU004 pU004 | 136 |
| 4157 | C pU004 pC pU004 pA pU004 pG pU004 pA pC pU004 pA pU004 pG pU004 pA pU004 pG pU004 pU004 pU004 | 156 | A pC pA pU004 pA pC004 pA pU004 pA pG pU004 pA pC004 pA pU004 pA pG pA pG pU004 pU004 | 137 |
| 5049 | C pA pA pC pG pU004 pA pA pC pG pA pU004 pU004 pU004 pC pA pU004 pG pA pU004 pU004 | 157 | U pC pA pU004 pG pA pA pA pU004 pC004 pG pU004 pU004 pA pC004 pG pU004 pU004 pG pU004 pU004 | 138 |
| 5057 | C pG pA pU004 pU004 pU004 pC pA pU004 pG pA pA pC pG pU004 pU004 pA pU004 pU004 pU004 pU004 | 158 | A pA pU004 pA pA pC004 pG pU004 pU004 pC004 pA pU004 pG pA pA pA pU004 pC004 pG pU004 pU004 | 139 |
| 5058 | G pA pU004 pU004 pU004 pC pA pU004 pG pA pA pC pG pU004 pU004 pA pU004 pU004 pA pU004 pU004 | 159 | U pA pA pU004 pA pA pC004 pG pU004 pU004 pC004 pA pU004 pG pA pA pA pU004 pC004 pU004 pU004 | 140 |
| 5059 | A pU004 pU004 pU004 pC pA pU004 pG pA pA pC pG pU004 pU004 pA pU004 pU004 pA pU004 pU004 pU004 | 160 | A pU pA pA pU004 pA pA pC004 pG pU004 pU004 pC004 pA pU pG pA pA pA pU004 pU004 pU004 | 141 |
| 5108 | C pU004 pG pU004 pA pU004 pG pG pG pA pG pC pU004 pU004 pA pA pC pU004 pU004 pU004 pU004 | 161 | A pA pG pU004 pU004 pA pA pG pC004 pU004 pC004 pC004 pC004 pA pU004 pA pC004 pA pG pU004 pU004 | 142 |
| 5144 | U004 pG pA pC pA pC pU004 pG pG pU004 pA pU004 pC pU004 pU004 pA pU004 pU004 pA pU004 pU004 | 162 | U pA pA pU004 pA pA pG pA pU004 pA pC004 pC004 pA pG pU004 pG pU004 pC004 pA pU004 pU004 | 143 |
| 5149 | C pU004 pG pG pU004 pA pU004 pC pU004 pU004 pA pU004 pU004 pA pA pA pG pU004 pA pU004 pU004 | 163 | U pA pC004 pU004 pU004 pU004 pA pA pU004 pA pA pG pA pU pA pC004 pC004 pA pG pU004 pU004 | 144 |

Table 5B lists example modified variants with the A85 S26 modifications:

A85: In guide strand all U as 2'-OMe-U, except positions 1, 2 and 14; 3' overhangs as 2'-OMe-U 2'-OMe-U S26: In sense strand all U as 2'-OMe-U and all C as 2'-OMe-C; 3' overhangs as 2'-OMe-U 2'-OMe-U

TABLE 5B

EPAS1 RNAi agents (example modified variants).

| Position_NM_001430 | Duplex Concept nickname_A85S26 | Sense Concept modified-sequence-string_A85S26 |
|---|---|---|
| 842 | Homo Sapiens_EPAS1_842_A85_S26 | ApU004 pGpGpC004 pGpApC004 pApU004 pGpApU004 pC004 pU004 pU004 pU004 pC004 pU004 pU004 pU004 |
| 2802 | Homo Sapiens_EPAS1_2802_A85_S26 | ApApApU004 pGpU004 pApC004 pC004 pC004 pApApU004 pGpApU004 pApApGpU004 pU004 |
| 3040 | Homo Sapiens_EPAS1_3040_A85_S26 | GpApApC004 pU004 pGpApC004 pC004 pApGpApU004 pApU004 pGpApC004 pU004 pU004 pU004 |
| 3304 | hs_EPAS1_3304_A85_S26 | ApGpApU004 pGpC004 pU004 pC004 pApC004 pU004 pU004 pU004 pApU004 pU004 pApU004 pC004 pU004 pU004 |
| 3310 | Homo Sapiens_EPAS1_3310_A85_S26 | U004 pC004 pApC004 pU004 pU004 pU004 pApU004 pU004 pApU004 pC004 pC004 pC004 pU004 pApU004 pU004 pU004 pU004 |
| 3345 | Homo Sapiens_EPAS1_3345_A85_S26 | GpU004 pU004 pU004 pU004 pApC004 pC004 pU004 pGpU004 pU004 pC004 pU004 pGpApApApU004 pU004 pU004 |
| 3354 | Homo Sapiens_EPAS1_3354_A85_S26 | GpU004 pU004 pC004 pU004 pGpApApApU004 pGpU004 pU004 pC004 pU004 pU004 pApApApU004 pU004 |
| 3735 | hs_EPAS1_3735_A85_S26 | ApC004 pU004 pC004 pC004 pApApC004 pGpU004 pApU004 pGpU004 pGpGpU004 pU004 pApU004 pU004 |
| 3739 | Homo Sapiens_EPAS1_3739_A85_S26 | C004 pApApC004 pGpU004 pApU004 pGpU004 pGpGpU004 pU004 pApU004 pC004 pU004 pGpU004 pU004 |
| 3875 | hs_EPAS1_3875_A85_S26 | U004 pGpGpGpU004 pU004 pApApGpU004 pGpU004 pU004 pU004 pApU004 pC004 pApU004 pU004 pU004 |
| 4153 | Homo Sapiens_EPAS1_4153_A85_S26 | C004 pApU004 pU004 pC004 pU004 pC004 pU004 pApU004 pGpU004 pApC004 pU004 pApU004 pGpU004 pU004 pU004 |
| 4157 | Homo Sapiens_EPAS1_4157_A85_S26 | C004 pU004 pC004 pU004 pApU004 pGpU004 pApC004 pU004 pApU004 pGpU004 pApU004 pGpU004 pU004 pU004 |
| 5049 | hs_EPAS1_5049_A85_S26 | C004 pApApC004 pGpU004 pApApC004 pGpApU004 pU004 pU004 pC004 pApU004 pGpApU004 pU004 |

TABLE 5B-continued

| EPAS1 RNAi agents (example modified variants). | | |
|---|---|---|
| 5057 | Homo Sapiens_EPAS1_5057_A85_S26 | C004 pGpApU004 pU004 pU004 pC004 pApU004 pGpApApC004 pGpU004 pU004 pApU004 pU004 pU004 pU004 |
| 5058 | Homo Sapiens_EPAS1_5058_A85_S26 | GpApU004 pU004 pU004 pC004 pApU004 pGpApApC004 pGpU004 pU004 pApU004 pU004 pApU004 pU004 |
| 5059 | Homo Sapiens_EPAS1_5059_A85_S26 | ApU004 pU004 pU004 pC004 pApU004 pGpApApC004 pGpU004 pU004 pApU004 pU004 pApU004 pU004 pU004 |
| 5108 | Homo Sapiens_EPAS1_5108_A85_S26 | C004 pU004 pGpU004 pApU004 pGpGpGpApGpC004 pU004 pU004 pApApC004 pU004 pU004 pU004 pU004 |
| 5144 | Homo Sapiens_EPAS1_5144_A85_S26 | U004 pGpApC004 pApC004 pU004 pGpGpU004 pApU004 pC004 pU004 pU004 pApU004 pU004 pApU004 pU004 |
| 5149 | hs_EPAS1_5149_A85_S26 | C004 pU004 pGpGpU004 pApU004 pC004 pU004 pU004 pApU004 pU004 pApApApGpU004 pApU004 pU004 |

| Position_NM_001430 | | Antisense Concept modified-sequence-string_A85S26 | |
|---|---|---|---|
| 842 | 77 | ApGpApApApGpApU004 pCpApU004 pGpU004 pCpGpCpCpApU004 pU004 pU004 | 96 |
| 2802 | 78 | CpUpU004 pApU004 pCpApU004 pU004 pGpGpGpU004 pApCpApU004 pU004 pU004 pU004 pU004 | 97 |
| 3040 | 79 | ApGpU004 pCpApU004 pApU004 pCpU004 pGpGpU004 pCpApGpU004 pU004 pCpU004 pU004 | 98 |
| 3304 | 80 | GpApU004 pApApU004 pApApApGpU004 pGpApGpCpApU004 pCpU004 pU004 pU004 | 99 |
| 3310 | 81 | ApApU004 pApGpGpGpApU004 pApApU004 pApApApGpU004 pGpApU004 pU004 | 100 |
| 3345 | 82 | ApUpU004 pU004 pCpApGpApApCpApGpGpUpApA pApApCpU004 pU004 | 101 |
| 3354 | 83 | UpUpU004 pApApGpApApCpApU004 pU004 pU004 pCpApGpApApCpU004 pU004 | 102 |
| 3735 | 84 | UpApApCpCpApCpApU004 pApCpGpU004 pUpGpGpApGpU004 pU004 pU004 | 103 |
| 3739 | 85 | CpApGpApU004 pApApCpCpApCpApU004 pApCpGpU004 pU004 pGpU004 pU004 | 104 |

TABLE 5B-continued

| EPAS1 RNAi agents (example modified variants). | | | |
|---|---|---|---|
| 3875 | 86 | ApUpGpApU004 pApApApCpApCpU004 pU004 pApApCpCpCpApU004 pU004 | 105 |
| 4153 | 87 | ApCpApU004 pApGpU004 pApCpApU004 pApGpApGpApApU004 pGpU004 pU004 | 106 |
| 4157 | 88 | ApCpApU004 pApCpApU004 pApGpU004 pApCpApU004 pApGpApGpU004 pU004 | 107 |
| 5049 | 89 | UpCpApU004 pGpApApApU004 pCpGpU004 pU004 pApCpGpU004 pU004 pGpU004 pU004 | 108 |
| 5057 | 90 | ApApU004 pApApCpGpU004 pU004 pCpApU004 pGpApApApU004 pCpGpU004 pU004 | 109 |
| 5058 | 91 | UpApApU004 pApApCpGpU004 pU004 pCpApU004 pGpApApApU004 pCpU004 pU004 | 110 |
| 5059 | 92 | ApUpApApU004 pApApCpGpU004 pU004 pCpApUpGpApApApU004 pU004 pU004 | 111 |
| 5108 | 93 | ApApGpU004 pU004 pApApGpCpU004 pCpCpCpApU004 pApCpApGpU004 pU004 | 112 |
| 5144 | 94 | UpApApU004 pApApGpApU004 pApCpCpApGpU004 pGpU004 pCpApU004 pU004 | 113 |
| 5149 | 95 | UpApCpU004 pU004 pU004 pApApU004 pApApGpApUpApCpCpApGpU004 pU004 | 114 |

In the duplexes listed in this table, the nickname comprises the term *Homo sapiens* or "hs", indicating the source of the sequence. The position is also indicated. Also indicated is the modification scheme (e.g., "A85 S26"). This modification scheme is:

A85: In guide strand all U as 2'-OMe-U, except pos. 1, 2 and 14; 3' overhangs as 2'-OMe-U 2'-OMe-U S26: In sense strand all U as 2'-OMe-U and all C as 2'-OMe-C; 3' overhangs as 2'-OMe-U 2'-OMe-U In addition, in the nicknames, the underscores ("_") and spaces (" ") are irrelevant. The modifications designated "004" are also diagrammed in FIG. 1.

The duplexes were prepared, as described in Example 2.

Additional example modified variants of EPAS1 sequences are shown in TABLES 5C to 5E, below.

Table 5C presents additional modified variants with the A51 S53 modifications. Position ("Pos.") is provided, as are the Duplex name and the sequence of the example modified sense and antisense sequence. 004 (2'-OMe) and other terms are defined elsewhere herein and in FIG. 1.

TABLE 5C

EPAS1 RNAi agents (example modified variants)

| Pos. | Duplex nickname | MODIFIED_SENSE_SEQUENCE | SEQ ID NO: | MODIFIED_ANTISENSE_SEQUENCE | SEQ ID NO: |
|---|---|---|---|---|---|
| 842 | hs_EPAS1_842_A51S53 | A pU004 pG pG pC pG pA pC pA pU004 pG pA pU004 pC pU004 pU004 pU004 pC pU004 pU004 pU004 | 164 | A pG pA pA pA pG pA pU004 pC004 pA pU004 pG pU004 pC pG pC004 pC004 pA pU004 pU004 pU004 | 182 |

TABLE 5C-continued

EPAS1 RNAi agents (example modified variants)

| Pos. | Duplex nickname | MODIFIED_SENSE_SEQUENCE | SEQ ID NO: | MODIFIED_ANTISENSE_SEQUENCE | SEQ ID NO: |
|---|---|---|---|---|---|
| 2802 | hs_EPAS1_2802_A51S53 | A pA pA pU004 pG pU004 pA pC pC pC pA pA pU004 pG pA pU004 pA pA pG pU004 pU004 | 165 | C pU pU004 pA pU004 pC004 pA pU004 pU004 pG pG pG pU004 pA pC004 pA pU004 pU004 pU004 pU004 pU004 | 183 |
| 3040 | hs_EPAS1_3040_A51S53 | G pA pA pC pU004 pG pA pC pC pA pG pA pU004 pA pU004 pG pA pC pU004 pU004 pU004 | 166 | A pG pU004 pC004 pA pU004 pA pU004 pC004 pU004 pG pG pU004 pC pA pG pU004 pU004 pC004 pU004 pU004 | 184 |
| 3304 | hs_EPAS1_3304_A51S53 | A pG pA pU004 pG pC pU004 pC pA pC pU004 pU004 pU004 pA pU004 pU004 pA pU004 pC pU004 pU004 | 167 | G pA pU004 pA pA pU004 pA pA pA pG pU004 pG pA pG pC004 pA pU004 pC004 pU004 pU004 pU004 | 185 |
| 3310 | hs_EPAS1_3310_A51S53 | U004 pC pA pC pU004 pU004 pU004 pA pU004 pU004 pA pU004 pC pC pC pU004 pA pU004 pU004 pU004 pU004 | 168 | A pA pU004 pA pG pG pG pA pU004 pA pA pU004 pA pA pA pG pU004 pG pA pU004 pU004 | 186 |
| 3345 | hs_EPAS1_3345_A51S53 | G pU004 pU004 pU004 pU004 pA pC pC pU004 pG pU004 pU004 pC pU004 pG pA pA pA pU004 pU004 pU004 | 169 | A pU pU004 pU004 pC004 pA pG pA pA pC004 pA pG pG pU pA pA pA pA pC004 pU004 pU004 | 187 |
| 3354 | hs_EPAS1_3354_A51S53 | G pU004 pU004 pC pU004 pG pA pA pA pU004 pG pU004 pU004 pC pU004 pU004 pA pA pA pU004 pU004 | 170 | U pU pU004 pA pA pG pA pA pC004 pA pU004 pU004 pU004 pC pA pG pA pA pC004 pU004 pU004 | 188 |
| 3735 | hs_EPAS1_3735_A51S53 | A pC pU004 pC pC pA pA pC pG pU004 pA pU004 pG pU004 pG pG pU004 pU004 pA pU004 pU004 | 171 | U pA pA pC004 pC004 pA pC004 pA pU004 pA pC004 pG pU004 pU pG pG pA pG pU004 pU004 pU004 | 189 |
| 3739 | hs_EPAS1_3739_A51S53 | C pA pA pC pG pU004 pA pU004 pG pU004 pG pG pU004 pU004 pA pU004 pC pU004 pG pU004 pU004 | 172 | C pA pG pA pU004 pA pA pC004 pC004 pA pC004 pA pU004 pA pC004 pG pU004 pU004 pG pU004 pU004 | 190 |
| 3875 | hs_EPAS1_3875_A51S53 | U004 pG pG pG pU004 pU004 pA pA pG pU004 pG pU004 pU004 pU004 pA pU004 pC pA pU004 pU004 pU004 | 173 | A pU pG pA pU004 pA pA pA pC004 pA pC004 pU004 pU004 pA pA pC004 pC004 pC004 pA pU004 pU004 | 191 |
| 4157 | hs_EPAS1_4157_A51S53 | C pU004 pC pU004 pA pU004 pG pU004 pA pC pU004 pA pU004 pG pU004 pA pU004 pG pU004 pU004 pU004 | 174 | A pC pA pU004 pA pC004 pA pU004 pA pG pU004 pA pC004 pA pU004 pA pG pA pG pU004 pU004 | 192 |
| 5049 | hs_EPAS1_5049_A51S53 | C pA pA pC pG pU004 pA pA pC pG pA pU004 pU004 pU004 pC pA pU004 pG pA pU004 pU004 | 175 | U pC pA pU004 pG pA pA pA pU004 pC004 pG pU004 pU004 pA pC004 pG pU004 pU004 pG pU004 pU004 | 193 |
| 5057 | hs_EPAS1_5057_A51S53 | C pG pA pU004 pU004 pU004 pC pA pU004 pG pA pA pC pG pU004 pU004 pA pU004 pU004 pU004 pU004 | 176 | A pA pU004 pA pA pC004 pG pU004 pU004 pC004 pA pU004 pG pA pA pA pU004 pC004 pG pU004 pU004 | 194 |
| 5058 | hs_EPAS1_5058_A51S53 | G pA pU004 pU004 pU004 pC pA pU004 pG pA pA pC pG pU004 pU004 pA pU004 pU004 pA pU004 pU004 | 177 | U pA pA pU004 pA pA pC004 pG pU004 pU004 pC004 pA pU004 pG pA pA pA pU004 pC004 pU004 pU004 | 195 |
| 5059 | hs_EPAS1_5059_A51S53 | A pU004 pU004 pU004 pC pA pU004 pG pA pA pC pG pU004 pU004 pA pU004 pU004 pA pU004 pU004 pU004 | 178 | A pU pA pA pU004 pA pA pC004 pG pU004 pU004 pC004 pA pU pG pA pA pA pU004 pU004 pU004 | 196 |
| 5108 | hs_EPAS1_5108_A51S53 | C pU004 pG pU004 pA pU004 pG pG pG pA pG pC pU004 pU004 pA pA pC pU004 pU004 pU004 pU004 | 179 | A pA pG pU004 pU004 pA pA pG pC004 pU004 pC004 pC004 pC004 pA pU004 pA pC004 pA pG pU004 pU004 | 197 |

TABLE 5C-continued

| EPAS1 RNAi agents (example modified variants) | | | | | |
|---|---|---|---|---|---|
| Pos. | Duplex nickname | MODIFIED_SENSE_SEQUENCE | SEQ ID NO: | MODIFIED_ANTISENSE_SEQUENCE | SEQ ID NO: |
| 5144 | hs_EPAS1_5144_A51S53 | U004 pG pA pC pA pC pU004 pG pG pU004 pA pU004 pC pU004 pU004 pA pU004 pU004 pA pU004 pU004 | 180 | U pA pA pU004 pA pA pG pA pU004 pA pC004 pC004 pA pG pU004 pG pU004 pC004 pA pU004 pU004 | 198 |
| 5149 | hs_EPAS1_5149_A51S53 | C pU004 pG pG pU004 pA pU004 pC pU004 pU004 pA pU004 pU004 pA pA pA pG pU004 pA pU004 pU004 | 181 | U pA pC004 pU004 pU004 pU004 pA pA pU004 pA pA pG pA pU pA pC004 pC004 pA pG pU004 pU004 | 199 |

Table 5D presents example modified EPAS1 RNAi agents, shown as 19-mer modified sequences. Table 5E shows related sequences as 21-mer sequences (including a dinucleotide overhang).

TABLE 5D

| EPAS1 RNAi agents (example modified variants) | | | | |
|---|---|---|---|---|
| Nickname_siRNA | 19-mer_guide_modified | SEQ ID NO: | 19-mer_sense_mod | SEQ ID NO: |
| hs_EPAS1_842_A51S53 | AGAAAGAtcAtGtCGccAt | 200 | AtGGCGACAtGAtCtttCt | 225 |
| hs_EPAS1_2802_A51S53 | CTtAtcAttGGGtAcAttt | 201 | AAAtGtACCCAAtGAtAAG | 226 |
| hs_EPAS1_3040_A51S53 | AGtcAtAtctGGtCAGttc | 202 | GAACtGACCAGAtAtGACt | 227 |
| hs_EPAS1_3304_A51S53 | GAtAAtAAAGtGAGcAtct | 203 | AGAtGCtCACtttAttAtC | 228 |
| hs_EPAS1_3310_A51S53 | AAtAGGGAtAAtAAAGtGA | 204 | tCACtttAttAtCCCtAtt | 229 |
| hs_EPAS1_3345_A51S53 | ATttcAGAAcAGGTAAAAc | 205 | GttttACCtGttCtGAAAt | 230 |
| hs_EPAS1_3354_A51S53 | TTtAAGAAcAtttCAGAAc | 206 | GttCtGAAAtGttCttAAA | 231 |
| hs_EPAS1_3735_A51S53 | TAAccAcAtAcGtTGGAGt | 207 | ACtCCAACGtAtGtGGttA | 232 |
| hs_EPAS1_3739_A51S53 | CAGAtAAccAcAtAcGttG | 208 | CAACGtAtGtGGttAtCtG | 233 |
| hs_EPAS1_3742_A51S53 | TCAcAGAtAAccACAtAcG | 209 | CGtAtGtGGttAtCtGtGA | 234 |
| hs_EPAS1_3743_A51S53 | TTcAcAGAtAAccAcAtAc | 210 | GtAtGtGGttAtCtGtGAA | 235 |
| hs_EPAS1_3747_A51S53 | AActttcAcAGAtAAccAc | 211 | GtGGttAtCtGtGAAAGtt | 236 |
| hs_EPAS1_3778_A51S53 | AAAcAccAGtttAGGAAAA | 212 | ttttCCtAAACtGGtGttt | 237 |
| hs_EPAS1_3870_A51S53 | AAAcActtAAcccAGAtAt | 213 | AtAtCtGGGttAAGtGttt | 238 |
| hs_EPAS1_3871_A51S53 | TAAAcActtAAccCAGAtA | 214 | tAtCtGGGttAAGtGtttA | 239 |
| hs_EPAS1_3875_A51S53 | ATGAtAAAcActtAAcccA | 215 | tGGGttAAGtGtttAtCAt | 240 |
| hs_EPAS1_4153_A51S53 | ACAtAGtAcAtAGAGAAtG | 216 | CAttCtCtAtGtACtAtGt | 241 |
| hs_EPAS1_4157_A51S53 | ACAtAcAtAGtAcAtAGAG | 217 | CtCtAtGtACtAtGtAtGt | 242 |
| hs_EPAS1_5049_A51S53 | TCAtGAAAtcGttAcGttG | 218 | CAACGtAACGAtttCAtGA | 243 |
| hs_EPAS1_5057_A51S53 | AAtAAcGttcAtGAAAtcG | 219 | CGAtttCAtGAACGttAtt | 244 |
| hs_EPAS1_5058_A51S53 | TAAtAAcGttcAtGAAAtc | 220 | GAtttCAtGAACGttAttA | 245 |
| hs_EPAS1_5059_A51S53 | ATAAtAAcGttcATGAAAt | 221 | AtttCAtGAACGttAttAt | 246 |
| hs_EPAS1_5108_A51S53 | AAGttAAGctcccAtAcAG | 222 | CtGtAtGGGAGCttAACtt | 247 |
| hs_EPAS1_5144_A51S53 | TAAtAAGAtAccAGtGtcA | 223 | tGACACtGGtAtCttAttA | 248 |
| hs_EPAS1_5149_A51S53 | TActttAAtAAGATAccAG | 224 | CtGGtAtCttAttAAAGtA | 249 |

Table 5E presents example modified EPAS1 RNAi agents, shown as 21-mer modified sequences (including a dinucleotide overhang). Table 5D shows related sequences as 21-mer sequences A modified variant of EPAS1 RNAi agent 5049 [wherein bold font nucleotides at positions 4, 9, 10, 12, 13, 15, 17 and 18 (counting 5' to 3') in the Guide Strand, and 6, 12-14, 17, and 20-21 (counting 5' to 3') in the Sense strand are 2'-OMe]

TABLE 5E

EPAS1 RNAi agents (example modified variants)

| Nickname_siRNA | 21-mer_guide_modified | SEQ ID NO: | 21-mer_sense_mod | SEQ ID NO: |
|---|---|---|---|---|
| hs_EPAS1_842_A51S53 | AGAAAGAtcAtGtCGccAtuu | 250 | AtGGCGACAtGAtCtttCtuu | 275 |
| hs_EPAS1_2802_A51S53 | CTtAtcAttGGGtAcAtttuu | 251 | AAAtGtACCCAAtGAtAAGuu | 276 |
| hs_EPAS1_3040_A51S53 | AGtcAtAtctGGtCAGttcuu | 252 | GAACtGACCAGAtAtGACtuu | 277 |
| hs_EPAS1_3304_A51S53 | GAtAAtAAAGtGAGcAtctuu | 253 | AGAtGCtCACtttAttAtCuu | 278 |
| hs_EPAS1_3310_A51S53 | AAtAGGGAtAAtAAAGtGAuu | 254 | tCACtttAttAtCCCtAttuu | 279 |
| hs_EPAS1_3345_A51S53 | ATttcAGAAcAGGTAAAAcuu | 255 | GttttACCtGttCtGAAAtuu | 280 |
| hs_EPAS1_3354_A51S53 | TTtAAGAAcAtttCAGAAcuu | 256 | GttCtGAAAtGttCttAAAuu | 281 |
| hs_EPAS1_3735_A51S53 | TAAccAcAtAcGtTGGAGtuu | 257 | ACtCCAACGtAtGtGGttAuu | 282 |
| hs_EPAS1_3739_A51S53 | CAGAtAAccAcAtAcGttGuu | 258 | CAACGtAtGtGGttAtCtGuu | 283 |
| hs_EPAS1_3742_A51S53 | TCAcAGAtAAccACAtAcGuu | 259 | CGtAtGtGGttAtCtGtGAuu | 284 |
| hs_EPAS1_3743_A51S53 | TTcAcAGAtAAccAcAtAcuu | 260 | GtAtGtGGttAtCtGtGAAuu | 285 |
| hs_EPAS1_3747_A51S53 | AActttcAcAGAtAAccAcuu | 261 | GtGGttAtCtGtGAAAGttuu | 286 |
| hs_EPAS1_3778_A51S53 | AAAcAccAGtttAGGAAAAuu | 262 | ttttCCtAAACtGGtGtttuu | 287 |
| hs_EPAS1_3870_A51S53 | AAAcActtAAcccAGAtAtuu | 263 | AtAtCtGGGttAAGtGtttuu | 288 |
| hs_EPAS1_3871_A51S53 | TAAAcActtAAccCAGAtAuu | 264 | tAtCtGGGttAAGtGtttAuu | 289 |
| hs_EPAS1_3875_A51S53 | ATGAtAAAcActtAAcccAuu | 265 | tGGGttAAGtGtttAtCAtuu | 290 |
| hs_EPAS1_4153_A51S53 | ACAtAGtAcAtAGAGAAtGuu | 266 | CAttCtCtAtGtACtAtGtuu | 291 |
| hs_EPAS1_4157_A51S53 | ACAtAcAtAGtAcAtAGAGuu | 267 | CtCtAtGtACtAtGtAtGtuu | 292 |
| hs_EPAS1_5049_A51S53 | TCAtGAAAtcGttAcGttGuu | 268 | CAACGtAACGAtttCAtGAuu | 293 |
| hs_EPAS1_5057_A51S53 | AAtAAcGttcAtGAAAtcGuu | 269 | CGAtttCAtGAACGttAttuu | 294 |
| hs_EPAS1_5058_A51S53 | TAAtAAcGttcAtGAAAtcuu | 270 | GAtttCAtGAACGttAttAuu | 295 |
| hs_EPAS1_5059_A51S53 | ATAAtAAcGttcATGAAAtuu | 271 | AtttCAtGAACGttAttAtuu | 296 |
| hs_EPAS1_5108_A51S53 | AAGttAAGctcccAtAcAGuu | 272 | CtGtAtGGGAGCttAACttuu | 297 |
| hs_EPAS1_5144_A51S53 | TAAtAAGAtAccAGtGtcAuu | 273 | tGACACtGGtAtCttAttAuu | 298 |
| hs_EPAS1_5149_A51S53 | TActttAAtAAGATAccAGuu | 274 | CtGGtAtCttAttAAAGtAuu | 299 |

Additional Modified Sequences

Below are listed modified variants of EPAS1 RNAi agent sequences:

is presented above, wherein the Guide (Anti-sense) strand is SEQ ID NO: 300 and the sense strand is SEQ ID NO: 301.

| | | | | | | | | | | | | | | | | | | | | | |
|---|---|---|---|---|---|---|---|---|---|---|---|---|---|---|---|---|---|---|---|---|---|
| siRNA 5049 | | | 1 | 2 | 3 | 4 | 5 | 6 | 7 | 8 | 9 | 10 | 11 | 12 | 13 | 14 | 15 | 16 | 17 | 18 | 19 | | |
| Guide strand | | | U | C | A | u | G | A | A | A | u | c | G | u | u | A | c | G | u | u | G | u | u |
| Sense strand | u | u | A | G | u | A | C | u | u | u | A | G | c | A | A | u | G | C | A | A | C | | |

| siRNA 3875 | | | 1 | 2 | 3 | 4 | 5 | 6 | 7 | 8 | 9 | 10 | 11 | 12 | 13 | 14 | 15 | 16 | 17 | 18 | 19 | | |
|---|---|---|---|---|---|---|---|---|---|---|---|---|---|---|---|---|---|---|---|---|---|---|---|
| Guide strand | | | A | U | G | A | u | A | A | A | C | A | C | u | u | A | A | C | C | C | A | u | u |
| Sense strand | u | u | u | A | c | u | A | u | u | u | G | u | G | A | A | u | u | G | G | G | u | | |

A modified variant of EPAS1 RNAi agent 3875 [wherein bold font nucleotides at positions 5, 12, 13, and 20-21 (counting 5' to 3') in the Guide strand, and positions 1, 5-6, 10, 12-14, 16-17, and 19-21 (counting 5' to 3') in the Sense strand are 2'-OMe] is presented above, wherein the Guide (Anti-sense) strand is SEQ ID NO: 302 and the sense strand is SEQ ID NO: 305.

| | | | 1 | 2 | 3 | 4 | 5 | 6 | 7 | 8 | 9 | 10 | 11 | 12 | 13 | 14 | 15 | 16 | 17 | 18 | 19 | | |
|---|---|---|---|---|---|---|---|---|---|---|---|---|---|---|---|---|---|---|---|---|---|---|---|
| Guide strand | | | U | C | A | u | G | A | A | A | u | c | G | u | u | A | c | G | u | u | G | A | C |
| Sense strand | C | A | A | G | u | A | C | u | u | u | A | G | C | A | A | u | G | C | A | A | C | | |

A modified variant of EPAS1 RNAi agent 5049 [wherein bold font nucleotides at positions 4, 9-10, 12-13, 15, and 17-18 (counting 5' to 3') in the Guide Strand, and positions 6, 12-14, and 17 (counting 5' to 3') in the Sense Strand are 2'-OMe] is presented above, wherein the Guide (Anti-sense) strand is SEQ ID NO: 303 and the sense strand is SEQ ID NO: 304.

Lower case nt (e.g., "u" and "c") are 2'-OMe. It should be understood that the sequences as represented herein (e.g., SEQ ID NO: 303 or nt 1-19 or SEQ ID NO: 303) represent both modified and unmodified variants. Additional modified variants of the EPAS1 RNAi agent sequences disclosed herein can be readily produced by one of ordinary skill in the art.

Example 2

Preparation of siRNAs

Small scale synthesis is used to prepare EPAS1 siRNAs; medium and large scale syntheses can also be used to prepare these siRNAs in larger quantities.

Small Scale Synthesis and Purification Methods for the Initial Screens (1 μmole Scale).

Small scale synthesis is used to generate siRNAs.

EPAS1 sequences are synthesized on MerMade 192 synthesizer (BioAutomation, Plano, Tex.) at 1 μmol scale.

In some experiments, for all the sequences in the list, 'endolight' chemistry is applied as detailed below: All pyrimidines (cytosine and uridine) in the sense strand contain 2'-O-Methyl bases (2'-O-Methyl C and 2'-O-Methyl U). In the antisense strand, pyrimidines adjacent to (towards 5' position) ribo A nucleoside are replaced with their corresponding 2-O-Methyl nucleosides.

In some experiments, a two base dTdT extension at 3' end of both sense and antisense sequences is introduced.

The sequence file is converted to a text file to make it compatible for loading in the MerMade 192 synthesis software.

Synthesis, Cleavage and Deprotection:

The synthesis of EPAS1 sequences can use solid supported oligonucleotide synthesis using phosphoramidite chemistry.

The synthesis of the above sequences is performed at 1 μM scale in 96 well plates. The ribo and 2-O-Methyl phosphoramidite solutions are prepared at 0.1M concentration and ethyl thio tetrazole (0.6M in Acetonitrile) is used as activator. Deblock solution, oxidizer solution and capping solution are prepared according to standard processes.

The synthesized sequences are cleaved and deprotected in 96 well plates, using methylamine solution (a 3:1 mixture of aqueous and ethanolic solutions) in the first step and fluoride reagent in the second step. The crude sequences are precipitated using acetone:ethanol (80:20) mix and the pellet are re-suspended in 0.02M sodium acetate buffer. Samples from each sequence are analyzed by LC-MS to confirm the identity, UV for quantification and a selected set of samples by IEX chromatography to determine purity.

Purification and Desalting:

EPAS1 tiled sequences are purified on AKTA explorer purification system using Source 15Q column. A column temperature of 65 C is maintained during purification. Sample injection and collection are performed in 96 well (1.8 mL-deep well) plates. A single peak corresponding to the full length sequence is collected in the eluent. The purified sequences are desalted on a Sephadex G25 column using AKTA purifier. The concentration of desalted EPAS1 sequences are calculated using absorbance at 260 nm wavelength and purity was measured by ion exchange chromatography.

Annealing:

Purified desalted sense and antisense single strands are mixed in equimolar amounts and annealed to form EPAS1 duplexes. The duplexes are prepared at 10 uM concentration in 1×PBS buffer and tested by capillary gel electrophoresis for purity.

Medium Scale Synthesis and Purification (1-50 μmol)

Medium scale synthesis can also be used to generate siRNAs.

Single-stranded RNAs in scales between 1 and 50 μmol are prepared by solid phase synthesis using an ABI DNA/RNA Synthesizer 394 (Applied Biosystems) and controlled pore glass (CPG, 500 Å, loading 80-100 μmol/g) purchased from Prime Synthesis (Aston, Pa.) as the solid support. For larger scales, empty synthesis columns (10 μmol) from Glen Research Corp. and large amidite (80 mL) and reagent bottles (450 mL) are used. RNA and RNA containing 2'-O-methyl nucleotides are generated by solid phase synthesis employing the corresponding phosphoramidites and 2'-O-methyl phosphoramidites, respectively (ChemGenes, Wilmington, Mass.). These building blocks are incorporated at selected sites within the sequence of the oligoribonucleotide chain using standard nucleoside phosphoramidite chemistry such as described in Current Protocols in Nucleic Acid Chemistry, Beaucage, S. L. et al. (Edrs.), John Wiley & Sons, Inc., New York, N.Y., USA. Phosphorothioate linkages are introduced using a solution of the 0.1 M DDTT (AM Chemicals, Oceanside, Calif.) in pyridine. Further ancillary reagents are obtained from Glen Research Corp. (Sterling, Va.).

Deprotection and purification of the crude oligoribonucleotides by anion exchange HPLC are carried out according to established procedures. Yields and concentrations are determined spectrophotometrically at a wavelength of 260 nm. Double stranded RNA is generated by mixing an equimolar solution of complementary strands in annealing buffer (typically phosphate buffered solution, PBS, Ambion, Applied Biosystems, Austin, Tex.) at the desired concentration. The mixture is then heated in a water bath at 85-90° C. for 5 minutes and cooled to room temperature over a period of 3-4 hours. The RNA duplex is stored at −20° C. until use.

Example 3

Example 3A

Methodology for In Vitro Screening

Cell Culture and Transfections

In some experiments, 786-O cells are grown to near confluence at 37° C. in an atmosphere of 5% $CO_2$ in DMEM supplemented with 10% FBS, streptomycin, and glutamine before being released from the flask(s) by trypsinization. Reverse transfection is carried out by adding 15 μl of Opti-MEM/siRNA duplexes to 77.5 ul of Opti-MEM plus 2.5 μl of Lipofectamine RNAiMax per well (Invitrogen, Carlsbad Calif. cat #13778-150) into a 384-well plate and incubating at room temperature for 20 minutes. 15 ul of this complex is transferred to another 384 well plate. $2.0\times10^3$ 786-O cells are then added. Cells are incubated for 48 hours prior to the addition of Bright-Glo to each well. Single point experiments use 6.5 nM final duplex concentration for 786-O cells for each of the EPAS1 siRNAs. A subset of siRNAs that showed robust silencing in the 6.5 nM screens are assayed over a range of concentrations from 10 nM to 0.0006 nM to determine their IC50.

Hundreds of EPAS1 duplexes were tested (Table 6 and data not shown). These demonstrated a wide range of RNAi activity, from poor to excellent. A subset of 19 EPAS1 RNAi agents is shown in Table 6, below. Additional studies were performed using other modified variants of the EPAS1 RNAi agents listed herein (data not shown).

Table 6. KD (Gene Knock-down) Mediated by EPAS1 RNAi Agents.

The EPAS1 RNAi agents used in Table 6 are the modified variants shown in Table 5C.

The residual gene activity at 30 nM, 15 nM and 7.5 nM in 786-O cells and SD (standard deviation) and residual activity at 6 nM in HeLa cells and SD are presented. The numbers indicate the residual gene activity; thus, for 842, column 2 indicates that at 30 nM in 786-O cells, there was 16.8% residual EPAS1 gene activity (compared to control), or 83.2% gene knockdown (reduction in gene activity).

TABLE 6

KD (Gene knock-down) mediated by EPAS1 RNAI agents.

| Nickname_siRNA_OLD | % Residual Activity 786-O 30 nM BC: 2739-2746 | SD 786-O 30 nM BC: 2739-2746 | % Residual Activity 786-O 15 nM BC: 2705-2712 | SD 786-O 15 nM BC: 2705-2712 | Residual Activity 786-O 7.5 nM BC: 2771-2778 | SD 786-O 7.5 nM BC: 2771-2778 | % Residual Activity HeLa 6 nM BC: 2713-2720 | SD HeLa 6 nM BC: 2713-2720 |
|---|---|---|---|---|---|---|---|---|
| hs_EPAS1_842_A51S53 | 16.8 | 3.2 | 9.2 | 0.8 | 6.6 | 3.1 | 29.1 | 5.3 |
| hs_EPAS1_2802_A51S53 | 9.5 | 0.6 | 19.2 | 3.6 | 12.2 | 2.6 | 45.5 | 13.8 |
| hs_EPAS1_3040_A51S53 | 20.5 | 8.6 | 30.4 | 4 | 14.4 | 2.7 | 56 | 17.3 |
| hs_EPAS1_3304_A51S53 | 18.4 | 4 | 37.8 | 6 | 16.9 | 6.1 | 47.7 | 23.6 |
| hs_EPAS1_3310_A51S53 | 19 | 4 | 29.2 | 4.3 | 12.9 | 4.5 | 58.8 | 22.7 |
| hs_EPAS1_3345_A51S53 | 20.1 | 7.1 | 30.4 | 8.1 | 9.8 | 0.9 | 48.8 | 13.9 |
| hs_EPAS1_3354_A51S53 | 22.6 | 9.5 | 38.3 | 12.8 | 10.3 | 3 | 50.3 | 9.3 |
| hs_EPAS1_3735_A51S53 | 22.3 | 5.4 | 20.5 | 3 | 15.5 | 7.4 | 41.4 | 7.4 |
| hs_EPAS1_3739_A51S53 | 11.9 | 3.5 | 24.5 | 7 | 17.4 | 9.6 | 34.7 | 14.9 |
| hs_EPAS1_3875_A51S53 | 26.3 | 6.4 | 28 | 2.4 | 12.5 | 4.9 | 47.8 | 24.9 |
| hs_EPAS1_4157_A51S53 | 13.5 | 4.1 | 25.6 | 3.8 | 18.8 | 7.9 | 29.5 | 7.2 |
| hs_EPAS1_5049_A51S53 | 17.6 | 9.7 | 14.5 | 5.2 | 8.3 | 1.1 | 18.7 | 10.7 |
| hs_EPAS1_5057_A51S53 | 11.2 | 3.5 | 10.5 | 2.9 | 5.2 | 0.3 | 26.2 | 10 |
| hs_EPAS1_5058_A51S53 | 7.7 | 2.1 | 12.2 | 6.7 | 10.2 | 1.7 | 28 | 14.2 |
| hs_EPAS1_5059_A51S53 | 12.4 | 3.8 | 8.9 | 4.1 | 6.2 | 3.1 | 32.6 | 15.4 |
| hs_EPAS1_5108_A51S53 | 10.4 | 4.5 | 12.8 | 3.2 | 8.4 | 0.6 | 24.7 | 16.4 |
| hs_EPAS1_5144_A51S53 | 22.8 | 2.1 | 21.6 | 11 | 10 | 2.4 | 21.9 | 5.9 |
| hs_EPAS1_5149_A51S53 | 10.5 | 2.5 | 22.7 | 5.7 | 11.4 | 4.6 | 29 | 10.5 |

Example 4

EC50 (IC50) Data of EPAS1 RNAi Agents in 786-O Cells (Reporter Assay)

Of the hundreds of EPAS1 duplexes designed, constructed and screened (Example 3 and data not shown), a subset of 19 efficacious EPAS1 RNAi agents were chosen for further study, including determination of EC50.

The purpose of this screen was to determine the EC50 (effective concentration 50; or the minimum dosage of RNAi agent capable of reducing the luciferase signal by 50%. The term IC50 (inhibitory concentration) is used interchangeably with EC50 herein.

Several criteria for selection were used, included, for example, >80% KD (gene knockdown), although in some cases, a particular EPAS1 RNAi agent did not meet all criteria evaluated. 786-O HRE cells were constructed using HRE-LUC reporter gene. In these cells, the Luciferase (LUC) reporter gene is under control of the Hif Response Element (HRE).

In addition, RNAi agents are tested for an ability to decrease HRE-luc PEST but do not effect UB6-luc Pest. Successful siRNA candidates had a greater than 100 fold IC-50 window between the on-target HRE-luc PEST assay and the off-target UB6-luc PEST assay. This indicates that these siRNA sequences do not cause off-target effects on cell growth, transcription, or translation in the 786-O cell line.

To determine IC50, a serial dilution was used, comprising 8 concentrations between 10 nM and 0.0006 nM. The siRNA duplexes were transfected into cells using Lipofectamine RNAiMax (Zhao et al. 2008 Mol. Biotech. 40: 19-26).

Table 7A shows the EC50 (or IC50) of various EPAS1 duplexes. For example, in the first line of this table, 842 with the modification set A85 S26 demonstrated in one assay an IC50 of 0.093 nM, after 3 days.

TABLE 7A

IC50 DATA FOR EPAS1 RNAi AGENTS

| Position_NM_001430 | A85_S26_IC50nM_HRE |
|---|---|
| 842 | 0.093 |
| 2802 | 0.38 |
| 3040 | 1.07 |
| 3304 | 0.43 |
| 3310 | 0.13 |
| 3345 | 0.12 |
| 3354 | 0.087 |
| 3735 | 0.102 |
| 3739 | 0.11 |
| 3875 | 0.042 |
| 4153 | 0.083 |
| 4157 | 0.104 |
| 5049 | 0.075 |
| 5057 | 0.107 |
| 5058 | 0.14 |
| 5059 | 0.186 |
| 5108 | 0.27 |
| 5144 | 0.085 |
| 5149 | 0.2 |

Table 7B shows IC50 data using the EPAS1 RNAi agents with the A51 S53 modification set. In columns 2 and 3, the RNAi agents were delivered with either of two LNP formulations (lipid nanoparticle formulations designated A and B), and in column 4, naked RNAi agents were used.

TABLE 7B

IC50 DATA FOR EPAS1 RNAi AGENTS

| Nick Name | LNP A A51S53 IC50 nM | LNP B A51S53 IC50 nM | A51S53 IC50 nM HRE |
|---|---|---|---|
| 842 A51 S53 | 0.9 | 1 | 0.1 |
| 2802 A51 S53 | 1.1 | 1.1 | 0.37 |
| 3040 A51 S53 | 1 | 0.89 | 0.42 |
| 3304 A51 S53 | 1.2 | 1 | |
| 3310 A51 S53 | | | |
| 3345 A51 S53 | 0.63 | 0.5 | 0.19 |
| 3354 A51 S53 | | | 0.017 |
| 3735 A51 S53 | | | 0.079 |
| 3739 A51 S53 | 0.39 | 0.29 | 0.19 |
| 3875 A51 S53 | | | |
| 4153 A51 S53 | | | 0.046 |
| 4157 A51 S53 | | | 0.06 |
| 5049 A51 S53 | | | 0.074 |
| 5057 A51 S53 | 0.35 | 0.25 | 0.2 |
| 5058 A51 S53 | 0.83 | 0.74 | 0.2 |
| 5059 A51 S53 | 0.76 | 1.09 | 0.13 |
| 5108 A51 S53 | 0.34 | 0.33 | 0.21 |
| 5144 A51 S53 | | | 0.05 |
| 5149 A51 S53 | 0.28 | 0.32 | 0.18 |

Successful siRNA candidates had a greater than 100 fold IC-50 window between the on-target HRE-luc PEST assay and the off-target UB6-luc PEST assay. This indicates that these siRNA sequences do not cause off-target effects on cell growth, transcription, or translation in the 786-O cell line.

Example 5

In Vivo Data of EPAS1 RNAi Agents

Effect of EPAS1 RNAi agents on 786-O tumor models in nude mice.

The efficacy of various EPAS1 RNAi agents in lipid nanoparticles was tested in vivo against 786-O clear cell renal cell carcinoma (CCRCC) tumors in nude mice. The numbers in the Table 8, below, show knockdown; e.g., "0.38" indicates 38% of control.

TABLE 8

Efficacy of EPAS1 RNAi agents against 786-O tumors in nude mice.

| Nick Name | KD TUMOR DATA 537 Study 72 A51 S53 | TUMOR DATA 338 Studies 76 & 80 A51 S53 | TUMOR DATA 338 Study 88 A51 S53 |
|---|---|---|---|
| 842 A51 S53 | 0.38 | 0.21 | |
| 2802 A51 S53 | 0.46 | 0.4 | |
| 3040 A51 S53 | 0.16 | | |
| 3304 A51 S53 | 0.43 | 0.55 | |
| 3310 A51 S53 | | 0.35 | |
| 3345 A51 S53 | 0.2 | 0.33 | |
| 3354 A51 S53 | | 0.3 | |
| 3735 A51 S53 | | 0.5 | 0.3 |
| 3739 A51 S53 | 0.32 | | |
| 3875 A51 S53 | | 0.4 | 0.37 |
| 4153 A51 S53 | | 0.3 | |
| 4157 A51 S53 | | 0.3 | |
| 5049 A51 S53 | | 0.55 | |
| 5057 A51 S53 | 0.4 | | |
| 5058 A51 S53 | 0.45 | 0.4 | |
| 5059 A51 S53 | 0.47 | 0.5 | |
| 5108 A51 S53 | 0.3 | | |
| 5144 A51 S53 | | 0.3 | |
| 5149 A51 S53 | 0.4 | | |

Some of these experiments show a decrease in tumor volume, especially in the late stage (towards the end of the experiment).

In a separate in vivo testing experiment, EPAS1 RNAi agents 5049, 3875 and 3735 are tested against 786-O tumors in nude mice.

5049 displays 0.17 (17% residual gene activity, or 83% gene knockdown).

3875 displays 0.24 (24% residual gene activity, or 76% gene knockdown).

3735 displays 0.24 (24% residual gene activity, or 76% gene knockdown).

Example 6

Overlapping RNAi Agents

Some of the siRNAs listed above overlap each other in sequence. The following table presents a compilation of groups of RNAi agents, wherein each member of a group overlaps with each other member of the same group by at least 12 nt. A 12-nt portion of the overlap of the sense strands and a 12-nt portion of the overlap of the antisense strand are presented, although in some cases the overlapping portion is longer than 12 nt. Thus, for example, 3304 and 3310 share the common technical feature of the sequence of UCACUUUAUUAUC (SEQ ID NO: 115) in the sense strand, and the sequence of GAUAAUAAAGUGA (SEQ ID NO: 120) in the antisense strand. Note, of course, that various groupings comprise different numbers of overlapping siRNAs; any two siRNAs within that group overlap. Thus, 5057, 5058 and 5059 all overlap with each other, meaning that any two of that group (5057 and 5059; or 5058 and 5059; or 5058 and 5059) share a common technical feature of an overlapping portion of the sense and/or anti-sense strand sequence. The disclosure thus encompasses any pair or grouping of overlapping siRNAs, wherein the pair share a technical feature, namely, the portion of the sense and/or anti-sense strand which overlaps, as described in Table 9.

TABLE 9

OVERLAPPING siRNAs

| Position NM_001430 | Sense | SEQ ID NO: | Antisense | SEQ ID NO: |
|---|---|---|---|---|
| 3304 and 3310 | UCACUUUAUUAUC | 115 | GAUAAUAAAGUGA | 120 |
| 3735 and 3739 | CAACGUAUGUGGUUA | 116 | UAACCACAUACGUUG | 121 |
| 4153 and 4157 | CUCUAUGUACUAUGU | 117 | ACAUAGUACAUAGAG | 122 |
| 5057, 5058 and 5059 | AUUUCAUGAACGUUAUU | 118 | AAUAACGUUCAUGAAAU | 123 |
| 5144 and 5149 | CUGGUAUCUUAUUA | 119 | UAAUAAGAUACCAG | 124 |

Thus, in various aspects, the disclosure pertains to a group of overlapping RNAi agents which comprise or consist of; or which comprise a sense strand or and anti-sense strand of; or which comprise a sense strand and/or and anti-sense strand comprising at least 15 contiguous nt with 0, 1, 2 or 3 mismatches from the sense and/or anti-sense strand of: any grouping of 3304 and 3310; 3735 and 3739; 4153 and 4157; 5057 and 5059; or 5058 and 5059; or 5058 and 5059; or 5144 and 5149; and modifications and variants thereof; and any overlapping pair or group thereof.

Embodiments

1. A composition comprising an RNAi agent comprising a sense strand and an antisense strand, wherein the antisense strand comprises at least 15 contiguous nucleotides differing by 0, 1, 2, or 3 nucleotides from the antisense strand of an RNAi agent to EPAS1 provided in any of Tables 1 to 5.
2. The composition of embodiment 1, wherein the composition further comprises a second RNAi agent to EPAS1.
3. The composition of embodiment 1, wherein the antisense strand is about 30 or fewer nucleotides in length.
4. The composition of embodiment 1, wherein the sense strand and the antisense strand form a duplex region about 15 to about 30 nucleotide pairs in length.
5. The composition of embodiment 1, wherein the antisense strand and the sense strand are both about 19 to about 23 nucleotides in length.
6. The composition of embodiment 1, wherein the RNAi agent comprises a modification that causes the RNAi agent to have increased stability in a biological sample or environment.
7. The composition of embodiment 1, wherein the RNAi agent comprises a modified sugar backbone, including a phosphorothioate linkage, or a 2'-modified nucleotide.
8. The composition of embodiment 1, wherein the RNAi agent comprises:

at least one 5'-uridine-adenine-3' (5'-ua-3') dinucleotide, wherein the uridine is a 2'-modified nucleotide; at least one 5'-uridine-guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; or at least one 5'-uridine-uridine-3' (5 '-uu-3') dinucleotide, wherein the 5'-uridine is a 2'-modified nucleotide.

9. The composition of embodiment 1, wherein the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).
10. The composition of embodiment 1, wherein the RNAi agent comprises a blunt end.
11. The composition of embodiment 1, wherein the RNAi agent comprises an overhang having 1 to 4 unpaired nucleotides.
12. The composition of embodiment 1, wherein the RNAi agent comprises an overhang at the 3'-end of the antisense strand of the RNAi agent.
13. The composition of embodiment 1, wherein the RNAi agent is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.
14. The composition of embodiment 1, wherein the RNAi agent is capable of inhibiting expression of EPAS1 by at least about 50% in 786-O tumors in nude mice.

15. The composition of embodiment 1, wherein the RNAi agent is capable of inhibiting expression of EPAS1 by at least about 70% at a concentration of 10 nM in 786-O cells in vitro.
16. The composition of embodiment 1, wherein the RNAi agent is capable of inhibiting expression of EPAS1 by at least about 80% at a concentration of 10 nM in 786-O cells in vitro.
17. The composition of embodiment 1, wherein the RNAi agent is capable of inhibiting expression of EPAS1 by at least about 90% at a concentration of 10 nM in 786-O cells in vitro.
18. The composition of embodiment 1, wherein the RNAi has an EC50 of no more than about 0.1 nM.
19. The composition of embodiment 1, wherein the RNAi has an EC50 of no more than about 0.01 nM.
20. The composition of embodiment 1, wherein the RNAi has an EC50 of no more than about 0.001 nM.
21. A composition comprising an RNAi agent comprising a sense strand and an antisense strand, wherein the sense strand and antisense strand comprise at least 15 contiguous nucleotides differing by 0, 1, 2, or 3 nucleotides, from the sense and antisense strand, respectively, of an RNAi agent to EPAS1 provided in any of Tables 1 to 5.
22. The composition of embodiment 21, wherein the composition comprises a second RNAi agent to EPAS1.
23. The composition of embodiment 21, wherein the antisense strand is 30 or fewer nucleotides in length.
24. The composition of embodiment 21, wherein the sense strand and the antisense strand form a duplex region 15 to 30 nucleotide pairs in length.
25. The composition of embodiment 21, wherein the antisense strand and the sense strand are both 19 to 23 nucleotides in length.
26. The composition of embodiment 21, wherein the RNAi agent comprises a modification that causes the RNAi agent to have increased stability in a biological sample or environment.
27. The composition of embodiment 21, wherein the RNAi agent comprises a modified sugar backbone, including a phosphorothioate linkage, or a 2'-modified nucleotide.
28. The composition of embodiment 21, wherein the RNAi agent comprises:

at least one 5'-uridine-adenine-3' (5'-ua-3') dinucleotide, wherein the uridine is a 2'-modified nucleotide; at least one 5'-uridine-guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; or at least one 5'-uridine-uridine-3' (5 '-uu-3') dinucleotide, wherein the 5'-uridine is a 2'-modified nucleotide.

29. The composition of embodiment 21, wherein the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).
30. The composition of embodiment 21, wherein the RNAi agent comprises a blunt end.
31. The composition of embodiment 21, wherein the RNAi agent comprises an overhang having 1 to 4 unpaired nucleotides.
32. The composition of embodiment 21, wherein the RNAi agent comprises an overhang at the 3'-end of the antisense strand of the RNAi agent.
33. The composition of embodiment 21, wherein the RNAi agent is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.
34. The composition of embodiment 21, wherein the RNAi agent is capable of inhibiting expression of EPAS1 by at least about 50% in 786-O tumors in nude mice.
35. The composition of embodiment 21, wherein the RNAi agent is capable of inhibiting expression of EPAS1 by at least about 70% at a concentration of 10 nM in 786-O cells in vitro.
36. The composition of embodiment 21, wherein the RNAi agent is capable of inhibiting expression of EPAS1 by at least about 80% at a concentration of 10 nM in 786-O cells in vitro.
37. The composition of embodiment 21, wherein the RNAi agent is capable of inhibiting expression of EPAS1 by at least about 90% at a concentration of 10 nM in 786-O cells in vitro.
38. The composition of embodiment 21, wherein the RNAi has an EC50 of no more than about 0.1 nM.
39. The composition of embodiment 21, wherein the RNAi has an EC50 of no more than about 0.01 nM.
40. The composition of embodiment 21, wherein the RNAi has an EC50 of no more than about 0.001 nM.
41. A method of treating a EPAS1-related disease in an individual, comprising the step of administering to the individual a therapeutically effective amount of a composition comprising an RNAi agent comprising a sense strand and an antisense strand, wherein the antisense strand comprises at least 15 contiguous nucleotides differing by 0, 1, 2, or 3 nucleotides from the antisense strand of an RNAi agent to EPAS1 provided in any of Tables 1 to 5.
42. The method of embodiment 41, wherein the EPAS1-related disease is cancer, metastases, astrocytoma, bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, non-small cell lung cancer, melanoma, multiple myeloma, ovarian cancer, rectal cancer, renal cancer, clear cell renal cell carcinoma (and metastases of this and other cancers), gingivitis, psoriasis, Kaposi's sarcoma-associated herpesvirus, preemclampsia, inflammation, chronic inflammation, neovascular diseases, or rheumatoid arthritis.
43. The method of embodiment 41, wherein the EPAS1-related disease is cancer.
44. The method of embodiment 41, wherein the method further comprises the step of administering an additional treatment.
45. The method of embodiment 44, wherein administration of the composition comprising the RNAi agent and the additional treatment is simultaneous, concurrent, separate or sequential.
46. The method of embodiment 41, wherein the EPAS1-related disease is a cancer, metastases, astrocytoma, bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, non-small cell lung cancer, melanoma, multiple myeloma, ovarian cancer, rectal cancer, renal cancer, clear cell renal cell carcinoma (and metastases of this and other cancers), gingivitis, psoriasis, Kaposi's sarcoma-associated herpesvirus, preemclampsia, inflammation, chronic inflammation, neovascular diseases, or rheumatoid arthritis.

47. The method of embodiment 41, where the EPAS1-related disease is cancer.

48. The method of embodiment 41, wherein the method further comprises the step of administering an additional treatment.

49. The method of embodiment 41, wherein administration of the composition comprising the RNAi agent and the additional treatment is simultaneous, concurrent, separate or sequential 50. The method of embodiment 41, wherein the EPAS1-related disease is cancer, metastases, astrocytoma, bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, non-small cell lung cancer, melanoma, multiple myeloma, ovarian cancer, rectal cancer, renal cancer, clear cell renal cell carcinoma (and metastases of this and other cancers), gingivitis, psoriasis, Kaposi's sarcoma-associated herpesvirus, preemclampsia, inflammation, chronic inflammation, neovascular diseases, or rheumatoid arthritis.

51. The method of embodiment 41, wherein the EPAS1-related disease is cancer.

52. The method of embodiment 41, wherein the composition comprises a second RNAi agent to EPAS1.

53. A method of inhibiting the expression of EPAS1 in an individual, comprising the step of administering to the individual a therapeutically effective amount of a composition comprising an RNAi agent comprising a sense strand and an antisense strand, wherein the antisense strand comprises at least 15 contiguous nucleotides differing by 0, 1, 2, or 3 nucleotides from the antisense strand of an RNAi agent to EPAS1 provided in any of Tables 1 to 5.

54. The method of embodiment 53, wherein the individual is afflicted with or susceptible to an EPAS1-related disease.

55. The method of embodiment 53, wherein the EPAS1-related disease is cancer, metastases, astrocytoma, bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, non-small cell lung cancer, melanoma, multiple myeloma, ovarian cancer, rectal cancer, renal cancer, clear cell renal cell carcinoma (and metastases of this and other cancers), gingivitis, psoriasis, Kaposi's sarcoma-associated herpesvirus, preemclampsia, inflammation, chronic inflammation, neovascular diseases, or rheumatoid arthritis.

56. The method of embodiment 53, wherein the EPAS1-related disease is cancer

57. The method of embodiment 53, wherein the method further comprises the step of administering an additional disease treatment.

58. The method of embodiment 53, wherein the method further comprises the step of administering an additional disease treatment, wherein administration of the composition comprising the RNAi agent and the additional disease treatment is simultaneous, concurrent, separate or sequential.

59. The method of embodiment 53, wherein the EPAS1-related disease is cancer, metastases, astrocytoma, bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, non-small cell lung cancer, melanoma, multiple myeloma, ovarian cancer, rectal cancer, renal cancer, clear cell renal cell carcinoma (and metastases of this and other cancers), gingivitis, psoriasis, Kaposi's sarcoma-associated herpesvirus, preemclampsia, inflammation, chronic inflammation, neovascular diseases, or rheumatoid arthritis.

60. The method of embodiment 53, where the EPAS1-related disease is cancer

61. The method of embodiment 53, wherein the method further comprises the step of administering an additional disease treatment.

62. The method of embodiment 53, wherein the method further comprises the step of administering an additional disease treatment, wherein administration of the composition comprising the RNAi agent and the additional disease treatment is simultaneous, concurrent, separate or sequential.

63. The method of embodiment 53, wherein the EPAS1-related disease is cancer, metastases, astrocytoma, bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, non-small cell lung cancer, melanoma, multiple myeloma, ovarian cancer, rectal cancer, renal cancer, clear cell renal cell carcinoma (and metastases of this and other cancers), gingivitis, psoriasis, Kaposi's sarcoma-associated herpesvirus, preemclampsia, inflammation, chronic inflammation, neovascular diseases, or rheumatoid arthritis.

64. The method of embodiment 53, wherein the EPAS1-related disease is cancer.

65. The method of embodiment 53, wherein the composition further comprises a second RNAi agent to EPAS1.

66. The composition according to embodiment 1 or embodiment 21, for use in a method of treating a EPAS1-related disease in an individual, the method comprising the step of administering to the individual a therapeutically effective amount of a composition according to embodiment 1 or embodiment 21.

67. The composition according to embodiment 1 or embodiment 21, for use in a method of inhibiting the expression of EPAS1 in an individual, the method comprising the step of administering to the individual a therapeutically effective amount of a composition according to embodiment 1 or embodiment 21.

68. The use of a composition according to embodiment 1 or embodiment 21, in the manufacture of a medicament for treatment of an EPAS1-related disease.

69. The use of embodiment 68, wherein the EPAS1-related disease is cancer, metastases, astrocytoma, bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, non-small cell lung cancer, melanoma, multiple myeloma, ovarian cancer, rectal cancer, renal cancer, clear cell renal cell carcinoma (and metastases of this and other cancers), gingivitis, psoriasis, Kaposi's sarcoma-associated herpesvirus, preemclampsia, inflammation, chronic inflammation, neovascular diseases, or rheumatoid arthritis.

70. The composition of embodiment 1 or embodiment 21, for use in the treatment of an EPAS1-related disease.
71. The use of embodiment 70, wherein the EPAS1-related disease is cancer
72. A method of inhibiting the expression of EPAS1 in an cell, comprising the step of introducing into the cell a composition comprising an RNAi agent comprising a sense strand and an antisense strand, wherein the antisense strand comprises at least 15 contiguous nucleotides differing by 0, 1, 2, or 3 nucleotides from the antisense strand of an RNAi agent to EPAS1 provided in any of Tables 1 to 5.
73. The composition of embodiment 1, wherein all pyrimidines are 2' O-methyl-modified nucleosides.
74. The composition of embodiment 21, wherein all pyrimidines are 2' O-methyl-modified nucleosides.

Unless defined otherwise, the technical and scientific terms used herein have the same meaning as that usually understood by a specialist familiar with the field to which the disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein. Unless indicated otherwise, each of the references cited herein is incorporated in its entirety by reference.

Claims to the invention are non-limiting and are provided below.

It is also noted that where the Claims recite a particular SEQ ID NO, claimed molecules of the recited sequence encompass molecules which are not modified or are modified by any known modification (e.g., with or without 2'-modifications, terminal dinucleotides, 3' end caps, etc.), unless the Claims recite otherwise. Although particular aspects and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of nucleic acid starting material, clone of interest, or library type is believed to be a matter of routine for a person of ordinary skill in the art with knowledge of the aspects described herein. Other aspects, advantages, and modifications considered to be within the scope of the following claims. Those skilled in the art will recognize or be able to ascertain, using no more than routine experimentation, many equivalents of the specific aspects of the invention described herein. Such equivalents are intended to be encompassed by the following claims. Redrafting of claim scope in later filed corresponding applications may be due to limitations by the patent laws of various countries and should not be interpreted as giving up subject matter of the claims.

We claim:

1. A composition comprising an RNAi agent for inhibiting expression of an EPAS1(Hif2 alpha) gene, wherein the RNAi agent comprises a sense strand and an antisense strand, wherein the antisense strand comprises the sequence of 5'-UCAUGAAAUCGUUACGUUG-3' (SEQ ID NO: 70), and the sense strand comprises the sequence of 5'-CAACGUAACGAUUUCAUGA-3' (SEQ ID NO: 51), and wherein the RNAi agent comprises at least one sugar backbone modification or at least one 2'-modified nucleotide.

2. The composition of claim 1, wherein the composition further comprises a second RNAi agent that inhibits the EPAS1 (Hif2 alpha) gene.

3. The composition of claim 1, wherein the antisense strand is about 30 or fewer nucleotides in length.

4. The composition of claim 1, wherein the sense strand and the antisense strand form a duplex region about 15 to about 30 nucleotide pairs in length.

5. The composition of claim 1, wherein the antisense strand and the sense strand are both about 19 to about 23 nucleotides in length.

6. The composition of claim 1, wherein the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOPE), and 2'-O-N-methylacetamido (2'-O-NMA).

7. The composition of claim 1, wherein the RNAi agent comprises a blunt end.

8. The composition of claim 1, wherein the RNAi agent comprises an overhang having 1 to 4 unpaired nucleotides.

9. The composition of claim 1, wherein the RNAi agent is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and transferrin.

10. The composition of claim 1, wherein the antisense strand is: U pC pA pU004 pG pA pA pA pU004 pC004 pG pU004 pU004 pA pC004 pG pU004 pU004 pG pU004 pU004 (SEQ ID NO: 138), and wherein the sense strand is: C pA pA pC pG pU004 pA pA pC pG pA pU004 pU004 pU004 pC pA pU004 pG pA pU004 pU004 (SEQ ID NO: 157), wherein p is a phosphate linkage, U is uridine, C is cytidine, A is adenosine, G is guanosine, U004 is 2'-O-methyl uridine modified nucleotide, and C004 is 2'-O-methyl cytosine modified nucleotide.

11. The composition of claim 1, wherein the antisense strand is: U pC pA pU004pG pA pA pA pU004 pC pG pU004 pU004 pA pC pG pU004 pU004 pG pU004 pU004 (SEQ ID NO: 108), and the sense strand is: C004 pA pA pC004 pG pU004 pA pA pC004 pG pA pU004 pU004 pU004 pC004 pA pU004 pG pA pU004 pU004 (SEQ ID NO: 89), wherein p is a phosphate linkage, U is uridine, C is cytidine, A is adenosine, G is guanosine, U004 is 2'-O-methyl uridine modified nucleotide, and C004 is 2'-O-methyl cytosine modified nucleotide.

12. The composition of claim 1, wherein the antisense strand is: U pC pA pU004 pG pA pA pA pU004 pC004 pG pU004 pU004 pA pC004 pG pU004 pU004 pG pU004 pU004(SEQ ID NO: 193), and the sense strand is: C pA pA pC pG pU004 pA pA pC pG pA pU004pU004 pU004 pC pA pU004 pG pA pU004 pU004 (SEQ ID NO: 175), wherein p is a phosphate linkage, U is uridine, C is cytidine, A is adenosine, G is guanosine, U004 is 2'-O-methyl uridine modified nucleotide, and C004 is 2'-O-methyl cytosine modified nucleotide.

13. A method of inhibiting the expression of an EPAS 1 (Hif2 alpha) gene in a subject, comprising administering to the subject a therapeutically effective amount of the composition of claim 1.

14. The method of claim 13, wherein the individual is afflicted with or susceptible to an EPAS 1-related disease.

15. The method of claim 14, wherein the EPAS1-related disease is cancer, metastases, astrocytoma, bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, non-small cell lung cancer, melanoma, multiple myeloma, ovarian cancer, rectal cancer, renal cancer, clear cell renal cell carcinoma (and metastases of this and other cancers), gingivitis, psoriasis, Kaposi's sarcoma-associated herpesvirus, preeclampsia, inflammation, chronic inflammation, neovascular diseases, or rheumatoid arthritis.

16. The method of claim 14, wherein the EPAS1-related disease is cancer.

17. The method of claim 13, wherein the method further comprises administering an additional disease treatment.

18. The method of claim 13, wherein the composition further comprises a second RNAi agent to EPAS1 (Hif2 alpha).

19. A method of treating a subject afflicted with or susceptible to an EPAS1-related disease, or preventing, modulating, or ameliorating in a subject a pathological state mediated at least in part by EPAS1 (Hif2 alpha) gene expression, the method comprising administering to the subject a therapeutically effective amount of the composition of claim 1.

20. The method of claim 19, wherein the EPAS1-related disease is cancer, metastases, astrocytoma, bladder cancer, breast cancer, chondrosarcoma, colorectal carcinoma, gastric carcinoma, glioblastoma, head and neck squamous cell carcinoma, hepatocellular carcinoma, lung adenocarcinoma, neuroblastoma, non-small cell lung cancer, melanoma, multiple myeloma, ovarian cancer, rectal cancer, renal cancer, clear cell renal cell carcinoma (and metastases of this and other cancers), gingivitis, psoriasis, Kaposi's sarcoma-associated herpesvirus, preeclampsia, inflammation, chronic inflammation, neovascular diseases, or rheumatoid arthritis.

* * * * *

SEQUENCE LISTING

```
<160> NUMBER OF SEQ ID NOS: 305

<210> SEQ ID NO 1
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1

atggcgacat gatctttct                                              19


<210> SEQ ID NO 2
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2

aaatgtaccc aatgataag                                              19


<210> SEQ ID NO 3
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 3
gaactgacca gatatgact 19

<210> SEQ ID NO 4
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 4
agatgctcac tttattatc 19

<210> SEQ ID NO 5
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 5
tcactttatt atccctatt 19

<210> SEQ ID NO 6
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 6
gttttacctg ttctgaaat 19

<210> SEQ ID NO 7
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 7
gttctgaaat gttcttaaa 19

<210> SEQ ID NO 8
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 8
actccaacgt atgtggtta 19

<210> SEQ ID NO 9
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 9
caacgtatgt ggttatctg 19

<210> SEQ ID NO 10
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 10
tgggttaagt gtttatcat 19

<210> SEQ ID NO 11
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 11
cattctctat gtactatgt 19

<210> SEQ ID NO 12
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 12
ctctatgtac tatgtatgt 19

<210> SEQ ID NO 13
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 13
caacgtaacg atttcatga 19

<210> SEQ ID NO 14
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 14
cgatttcatg aacgttatt 19

<210> SEQ ID NO 15
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 15
gatttcatga acgttatta 19

<210> SEQ ID NO 16
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 16
atttcatgaa cgttattat 19

<210> SEQ ID NO 17
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 17
ctgtatggga gcttaactt 19

<210> SEQ ID NO 18
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 18
tgacactggt atcttatta 19

<210> SEQ ID NO 19
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 19
ctggtatctt attaaagta 19

<210> SEQ ID NO 20
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 20
agaaagatca tgtcgccat 19

<210> SEQ ID NO 21
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 21
cttatcattg ggtacattt 19

<210> SEQ ID NO 22
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 22
agtcatatct ggtcagttc 19

<210> SEQ ID NO 23
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 23
gataataaag tgagcatct 19

<210> SEQ ID NO 24
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 24
aatagggata ataaagtga 19

<210> SEQ ID NO 25
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 25
atttcagaac aggtaaaac 19

<210> SEQ ID NO 26
<211> LENGTH: 19
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 26
tttaagaaca tttcagaac 19

<210> SEQ ID NO 27
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 27
taaccacata cgttggagt 19

<210> SEQ ID NO 28
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 28
cagataacca catacgttg 19

<210> SEQ ID NO 29
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 29
atgataaaca cttaaccca 19

<210> SEQ ID NO 30
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 30
acatagtaca tagagaatg 19

<210> SEQ ID NO 31
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 31
acatacatag tacatagag 19

<210> SEQ ID NO 32
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 32
tcatgaaatc gttacgttg 19

<210> SEQ ID NO 33
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 33
aataacgttc atgaaatcg 19

<210> SEQ ID NO 34
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 34
taataacgtt catgaaatc 19

<210> SEQ ID NO 35
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 35
ataataacgt tcatgaaat 19

<210> SEQ ID NO 36
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 36
aagttaagct cccatacag 19

<210> SEQ ID NO 37
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 37
taataagata ccagtgtca 19

<210> SEQ ID NO 38
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 38
tactttaata agataccag 19

<210> SEQ ID NO 39
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 39
auggcgacau gaucuuucu 19

<210> SEQ ID NO 40
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 40
aaauguaccc aaugauaag 19

<210> SEQ ID NO 41
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 41
gaacugacca gauaugacu 19

<210> SEQ ID NO 42
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 42
agaugcucac uuuauuauc 19

<210> SEQ ID NO 43
<211> LENGTH: 19

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43

ucacuuuauu aucccuauu                                                19


<210> SEQ ID NO 44
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44

guuuuaccug uucugaaau                                                19


<210> SEQ ID NO 45
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45

guucugaaau guucuuaaa                                                19


<210> SEQ ID NO 46
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46

acuccaacgu augugguua                                                19


<210> SEQ ID NO 47
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47

caacguaugu gguuaucug                                                19


<210> SEQ ID NO 48
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
```

uggguuaagu guuuaucau 19

<210> SEQ ID NO 49
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 49
cauucucuau guacuaugu 19

<210> SEQ ID NO 50
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 50
cucuauguac uauguaugu 19

<210> SEQ ID NO 51
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 51
caacguaacg auuucauga 19

<210> SEQ ID NO 52
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 52
cgauuucaug aacguuauu 19

<210> SEQ ID NO 53
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 53
gauuucauga acguuauua 19

<210> SEQ ID NO 54
<211> LENGTH: 19
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 54

auuucaugaa cguuauuau                                              19


<210> SEQ ID NO 55
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55

cuguauggga gcuuaacuu                                              19


<210> SEQ ID NO 56
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56

ugacacuggu aucuuauua                                              19


<210> SEQ ID NO 57
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57

cugguaucuu auuaaagua                                              19


<210> SEQ ID NO 58
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58

agaaagauca ugucgccau                                              19


<210> SEQ ID NO 59
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59

cuuaucauug gguacauuu                                              19


<210> SEQ ID NO 60
```

<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 60
agucauaucu ggucaguuc 19

<210> SEQ ID NO 61
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 61
gauaauaaag ugagcaucu 19

<210> SEQ ID NO 62
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 62
aauagggaua auaaaguga 19

<210> SEQ ID NO 63
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 63
auuucagaac agguaaaac 19

<210> SEQ ID NO 64
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 64
uuuaagaaca uuucagaac 19

<210> SEQ ID NO 65
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 65
uaaccacaua cguuggagu 19

<210> SEQ ID NO 66
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 66
cagauaacca cauacguug 19

<210> SEQ ID NO 67
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 67
augauaaaca cuuaaccca 19

<210> SEQ ID NO 68
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 68
acauaguaca uagagaaug 19

<210> SEQ ID NO 69
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 69
acauacauag uacauagag 19

<210> SEQ ID NO 70
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 70
ucaugaaauc guuacguug 19

<210> SEQ ID NO 71
<211> LENGTH: 19
<212> TYPE: RNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 71
aauaacguuc augaaaucg 19

<210> SEQ ID NO 72
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 72
uaauaacguu caugaaauc 19

<210> SEQ ID NO 73
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 73
auaauaacgu ucaugaaau 19

<210> SEQ ID NO 74
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 74
aaguuaagcu cccauacag 19

<210> SEQ ID NO 75
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 75
uaauaagaua ccaguguca 19

<210> SEQ ID NO 76
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 76
uacuuuaaua agauaccag 19

<210> SEQ ID NO 77
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 77
auggcgacau gaucuuucuu u 21

<210> SEQ ID NO 78
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 78
aaauguaccc aaugauaagu u 21

<210> SEQ ID NO 79
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 79
gaacugacca gauaugacuu u 21

<210> SEQ ID NO 80
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 80
agaugcucac uuuauuaucu u 21

<210> SEQ ID NO 81
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 81
ucacuuuauu aucccuauuu u 21

<210> SEQ ID NO 82
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 82
guuuuaccug uucugaaauu u 21

<210> SEQ ID NO 83
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 83
guucugaaau guucuuaaau u 21

<210> SEQ ID NO 84
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 84
acuccaacgu augugguuau u 21

<210> SEQ ID NO 85
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 85
caacguaugu gguuaucugu u 21

<210> SEQ ID NO 86
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 86
uggguuaagu guuuaucauu u 21

<210> SEQ ID NO 87
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 87
cauucucuau guacuauguu u 21

<210> SEQ ID NO 88
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
cucuauguac uauguauguu u 21

<210> SEQ ID NO 89
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
caacguaacg auuucaugau u 21

<210> SEQ ID NO 90
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
cgauuucaug aacguuauuu u 21

<210> SEQ ID NO 91
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
gauuucauga acguuauuau u 21

<210> SEQ ID NO 92
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
auuucaugaa cguuauuauu u 21

<210> SEQ ID NO 93
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
cuguauggga gcuuaacuuu u 21

```
<210> SEQ ID NO 94
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94

ugacacuggu aucuuauuau u                                              21


<210> SEQ ID NO 95
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95

cugguaucuu auuaaaguau u                                              21


<210> SEQ ID NO 96
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96

agaaagauca ugucgccauu u                                              21


<210> SEQ ID NO 97
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97

cuuaucauug gguacauuuu u                                              21


<210> SEQ ID NO 98
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98

agucauaucu ggucaguucu u                                              21


<210> SEQ ID NO 99
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 99
gauaauaaag ugagcaucuu u 21

<210> SEQ ID NO 100
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 100
aauagggaua auaaagugau u 21

<210> SEQ ID NO 101
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 101
auuucagaac agguaaaacu u 21

<210> SEQ ID NO 102
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 102
uuuaagaaca uuucagaacu u 21

<210> SEQ ID NO 103
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 103
uaaccacaua cguuggaguu u 21

<210> SEQ ID NO 104
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 104
cagauaacca cauacguugu u 21

<210> SEQ ID NO 105
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105

augauaaaca cuuaacccau u                                              21


<210> SEQ ID NO 106
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106

acauaguaca uagagaaugu u                                              21


<210> SEQ ID NO 107
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107

acauacauag uacauagagu u                                              21


<210> SEQ ID NO 108
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108

ucaugaaauc guuacguugu u                                              21


<210> SEQ ID NO 109
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109

aauaacguuc augaaaucgu u                                              21


<210> SEQ ID NO 110
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110

uaauaacguu caugaaaucu u                                              21
```

<210> SEQ ID NO 111
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 111
auaauaacgu ucaugaaauu u 21

<210> SEQ ID NO 112
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 112
aaguuaagcu cccauacagu u 21

<210> SEQ ID NO 113
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 113
uaauaagaua ccagugucau u 21

<210> SEQ ID NO 114
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 114
uacuuuaaua agauaccagu u 21

<210> SEQ ID NO 115
<211> LENGTH: 13
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 115
ucacuuuauu auc 13

<210> SEQ ID NO 116
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 116
caacguaugu gguua 15

<210> SEQ ID NO 117
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 117
cucuauguac uaugu 15

<210> SEQ ID NO 118
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 118
auuucaugaa cguuauu 17

<210> SEQ ID NO 119
<211> LENGTH: 14
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 119
cugguaucuu auua 14

<210> SEQ ID NO 120
<211> LENGTH: 13
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 120
gauaauaaag uga 13

<210> SEQ ID NO 121
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 121
uaaccacaua cguug 15

<210> SEQ ID NO 122
<211> LENGTH: 15

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122

acauaguaca uagag                                                    15


<210> SEQ ID NO 123
<211> LENGTH: 17
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123

aauaacguuc augaaau                                                  17


<210> SEQ ID NO 124
<211> LENGTH: 14
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124

uaauaagaua ccag                                                     14


<210> SEQ ID NO 125
<211> LENGTH: 5186
<212> TYPE: DNA
<213> ORGANISM: Macaca fasicularis
<220> FEATURE:
<221> NAME/KEY: modified_base
<222> LOCATION: (1)..(62)
<223> OTHER INFORMATION: a, c, t, g, unknown or other
<220> FEATURE:
<221> NAME/KEY: modified_base
<222> LOCATION: (255)..(284)
<223> OTHER INFORMATION: a, c, t, g, unknown or other
<220> FEATURE:
<221> NAME/KEY: modified_base
<222> LOCATION: (2402)..(2402)
<223> OTHER INFORMATION: a, c, t, g, unknown or other
<220> FEATURE:
<221> NAME/KEY: modified_base
<222> LOCATION: (2481)..(2508)
<223> OTHER INFORMATION: a, c, t, g, unknown or other
<220> FEATURE:
<221> NAME/KEY: modified_base
<222> LOCATION: (3351)..(3472)
<223> OTHER INFORMATION: a, c, t, g, unknown or other
<220> FEATURE:
<221> NAME/KEY: modified_base
<222> LOCATION: (3544)..(3672)
<223> OTHER INFORMATION: a, c, t, g, unknown or other
<220> FEATURE:
<221> NAME/KEY: modified_base
<222> LOCATION: (3812)..(3820)
<223> OTHER INFORMATION: a, c, t, g, unknown or other
<220> FEATURE:
<221> NAME/KEY: modified_base
<222> LOCATION: (4470)..(4575)
<223> OTHER INFORMATION: a, c, t, g, unknown or other
<220> FEATURE:
<221> NAME/KEY: modified_base
<222> LOCATION: (4848)..(4865)
```

<223> OTHER INFORMATION: a, c, t, g, unknown or other
<220> FEATURE:
<221> NAME/KEY: modified_base
<222> LOCATION: (5142)..(5186)
<223> OTHER INFORMATION: a, c, t, g, unknown or other

<400> SEQUENCE: 125

```
nnnnnnnnnn nnnnnnnnnn nnnnnnnnnn nnnnnnnnnn nnnnnnnnnn nnnnnnnnnn     60

nnctcggcag tctcctgaga ctgtatggtc agctcagccc agcctccgac tccttccgac    120

tcccagcatt cgagccactt tttttttcc ttgaaaactc agaaaagtga ctctttttcc    180

agggaaaaag gaacttgggt tcccttctcg ccgtcctttt ttcgggtctg acagcctcca    240

cccactcctt ccccnnnnnn nnnnnnnnnn nnnnnnnnnn nnnncgtcac ctttctccac    300

ccccaccccc gcacctagcc cgccgcgcgc caccttccac ctgactgcgc ggggcgctcg    360

ggacctgcgc gcacctcgga ccttcaccac ccgccccggc cgccgggagc ggacgagggc    420

cacagctccc cacccgccgg gaagcccagg tgctcggcgt ctgaacgtct caaagggcca    480

cagcgacaat gacagctgac aaggagaaga aaaggagtag ctcggagagg aggaaggaga    540

agtcccggga tgccgcacgg tgccggcgga gcaaggagac ggaggtgttc tacgagctgg    600

cccatgagct gcctctgccc cacagcgtga gctcccatct ggacaaggcc tccatcatgc    660

gactggcgat cagcttcctg cgaacacaca agctcctctc ctcagtttgc tctgaaaatg    720

agtctgaagc tgaagctgac cagcagatgg acaacttgta cctgaaagcc ttggagggtt    780

tcattgccgt ggtgacccaa gatggcgaca tgatctttct gtcagaaaac atcagcaagt    840

tcatgggact tacacaggtg gagctaacag gacatagtat ctttgacttc actcatccct    900

gcgaccacga ggagattcgt gagaacctga gtctcaaaaa tggctctggt tttgggaaaa    960

aaagcaaaga catgtccaca gagcgggact tcttcatgag gatgaagtgc acggtcacca   1020

acagaggccg tactgtcaac ctcaagtcag ccacctggaa ggtcttgcac tgcacgggcc   1080

aagtgaaagt ctacaacaac tgccctcctc acaatagtct gtgtggctac aaggagcccc   1140

tgctgtcctg cctcatcatc atgtgtgaac cgatccagca cccatcccac atggacattc   1200

ccctggacag caagaccttc ctgagccgcc acagcatgga catgaagttc acctactgtg   1260

atgacagaat cacagaactg attggttacc accctgagga gctgcttggc cgctcagcct   1320

atgaattcta ccatgcgcta gactccgaga acatgaccaa gagtcaccag aacttgtgca   1380

ccaagggcca ggtggtaagt ggccagtacc ggatgctcgc aaagcatggg ggctacgtgt   1440

ggctggaaac ccaggggaca gtcatctaca accctcgcaa cctgcagccc cagtgcatca   1500

tgtgtgtcaa ctacgttctg agtgagattg agaagaatga cgtggtgttc tccatggacc   1560

agacggaatc cctgttcaag ccccacctga tggccatgaa cggcatcttt gatagcagtg   1620

gcaagggggc tgtgtctgag aagagtaact tcctattcac caagctaaag gaggagcctg   1680

aggagctggc ccagctggct cccaccccag gagacgccat catctctctg gatttcggga   1740

atcagaactt cgaggaatcc tcagcctatg gcaaggccat cctgcccccg agccagccgt   1800

gggccacaga gttgaggagc cacagcaccc agagcgaggc tgggagcctg cctgccttca   1860

ccgtgcccca ggcagccgcc ccgggcagca ccaccccccag tgccaccagc agcagcagca   1920

gctgctccac gcccaatagc cctgaagact attatacatc tttggataac gacctgaaga   1980

ttgaagtgat tgagaagctc ttcgccatgg acacagaggc caaggaccaa tgcagtaccc   2040

agacggattt caatgagctg gacttggaga cactggcacc ctatattccc atggatgggg   2100

aagacttcca gctgagcccc atctgccccg aggagcggct cttggcggag aacccacagt   2160
```

-continued

```
ccacccccca gcactgcttc agtgccatga caaacatctt ccagccactg gcccctgtag   2220
ccccgcacag tcccttcctc ctggacaagt ttcagcagca gctggagagc aagaagacag   2280
agcccgagca ccggcccatg tcctccatct tctttgatgc cggaagcaaa gcatccctgc   2340
caccatgctg tggccaggcc agcacccctc tctcttccat gggggcaga tccaataccc   2400
antggccccc agatccacca ttacattttg ggcccacaaa gtgggccgtc ggggatcagc   2460
gcacagagtt cctgggagcg nnnnnnnnnn nnnnnnnnnn nnnnnnnncc catatctcca   2520
cattcaagac aaggtctgca aagggttttg gggctcgagg cccagacgtg ctgagcccgg   2580
ccatggtagc cctctccaac aagctgaagc tgaagcgaca gctggagtat gaagagcaag   2640
ccttccagga cctgagtggg ggggacccac ctggtggcag cacttcacat ttgatgtgga   2700
aacggatgaa gaacctcagg ggtgggagct gccctttgat gccggacaag ccactgagcg   2760
caaatgtccc caatggtaag ttcacccaaa atcctgtgag gggcctgggc catcccctga   2820
gacatctgcc gctgccacag cctccatctg ccgtcagtcc cggggagaac agcaagagca   2880
ggttccccgc acagtgctat gccacccagt accaggacta cagcctgtcg tcagcccaca   2940
aggtgtcagg catggcaagc cggctgctcg ggccctcgtt tgagtcctac ctgctgcctg   3000
aactgaccag atatgactgt gaggtgaacg tgcccgtgct gggaagctcc acgctcctgc   3060
aaggaggga cctcctcaga gccctggacc aggccacctg agccaggcct tccacctggg   3120
cagcacctct gccgacaccg tcccaccagc ttcactctct ccatctgttt ttgtaactag   3180
gtatttctaa caccagcaca ctatttacaa gatggactta cctggcagac ttgcccaggt   3240
caccacgcag tggccttttt ctgagatgct cactttatta tccctatttt taaagtacac   3300
aattgtttta cctgttctga aatgttctta aattttgtaa tatttttttt nnnnnnnnnn   3360
nnnnnnnnnn nnnnnnnnnn nnnnnnnnnn nnnnnnnnnn nnnnnnnnnn nnnnnnnnnn   3420
nnnnnnnnnn nnnnnnnnnn nnnnnnnnnn nnnnnnnnnn nnnnnnnnnn nngcgttagc   3480
ttcattttac taaaaagatt cctcgttact gttgttgcca aagagaaaca aaaatgatgt   3540
tgcnnnnnnn nnnnnnnnnn nnnnnnnnnn nnnnnnnnnn nnnnnnnnnn nnnnnnnnnn   3600
nnnnnnnnnn nnnnnnnnnn nnnnnnnnnn nnnnnnnnnn nnnnnnnnnn nnnnnnnnnn   3660
nnnnnnnnnn nnaaaaaaga aatgtgaagg gtcaactcca acgtatgtgg ttatctgtga   3720
aggctgcata gcgtggcttt tcctaaactg gtgtttttcc cccgcattcg gtggattttt   3780
tattattatt caaaaacata actgagtttt tnnnnnnnnn agaaaattta tatctgggtt   3840
aagtgtttat catatatatg ggtactctgt aatatctaaa accttagaaa cggaaatgga   3900
atcctgctca caaaatcact ttaagatctt ttcaaagctg ttaatttttc ttggtgttgt   3960
ggacactgca gacttgtcca gtgctcccac agcctgtacg gacactgtgg aaggcctccc   4020
tctgtcggct ttttgccatc tgtgatatgc cataggtgtg acaatccgag cagtggagtc   4080
attcagtggg agcactgcgc gctatcccct catgttctct atgtactatg tatgtatgta   4140
ttattattat tgctgccaag agggtctgat ggcacgttgt ggggtcgggg ggtggggcgg   4200
ggaagtgctc taacttttct taaggttttg ttgctagccc ttcaagtgca ctgagctatg   4260
tgactcggat ggtctttcac acggcacatt tagacatttc cagaactacc atgagatggt   4320
ttagatggga attcatgcaa atgaggggtc agaaatggta tagtgacccg gtccacgtcc   4380
tccaagctca cgaccttgga gccccgtgga gctggactga ggaggaggct gcacagcggg   4440
agagcagctg gtccagacca gccttgcagn nnnnnnnnnn nnnnnnnnnn nnnnnnnnnn   4500
```

```
nnnnnnnnnn nnnnnnnnnn nnnnnnnnnn nnnnnnnnnn nnnnnnnnnn nnnnnnnnnn   4560

nnnnnnnnnn nnnnnaagca ctgaaaatag cgttcccaga gcacattgca actcactggg   4620

taagagggac gacacctctg gtttttcaat accaattaca tggaactttt ctgtaatggg   4680

tacaacgaag aagtttctaa aaacacacac aaagcacatt aggccaacta tttagtaagc   4740

ccggatggac ttattgccag aaacaaaaag tagctttcaa aagaaattta agttatatga   4800

gaaattcctt agtcatggtg ttgtctaaat catattttag ctgcacgnnn nnnnnnnnnn   4860

nnnnnaggca gaacttgaag ggttactgac atgtaaatgc tggtatttga tttcctgtgt   4920

gtgttgccct ggcattaagg gcattttacc cttgcagttt tactaaaaca ctgaaaaata   4980

ttccaagctt catattaacc ctacctgtca acgtaacgat ttcatgaaca ttattatatt   5040

gtcgaattcc tactgacaac attataactg tatgggagct taactttata aggaaatgta   5100

ttttgacact ggtatcttat taaagtattc tgatcctaaa annnnnnnnn nnnnnnnnnn   5160

nnnnnnnnnn nnnnnnnnnn nnnnnn                                        5186
```

<210> SEQ ID NO 126
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 126
agaaagauca ugucgccauu u 21

<210> SEQ ID NO 127
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 127
cuuaucauug gguacauuuu u 21

<210> SEQ ID NO 128
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 128
agucauaucu ggucaguucu u 21

<210> SEQ ID NO 129
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 129
gauaauaaag ugagcaucuu u 21

<210> SEQ ID NO 130
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 130
aauagggaua auaaagugau u 21

<210> SEQ ID NO 131
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 131
auuucagaac agguaaaacu u 21

<210> SEQ ID NO 132
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 132
uuuaagaaca uuucagaacu u 21

<210> SEQ ID NO 133
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 133
uaaccacaua cguuggaguu u 21

<210> SEQ ID NO 134
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 134
cagauaacca cauacguugu u 21

<210> SEQ ID NO 135
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 135
augauaaaca cuuaacccau u 21

<210> SEQ ID NO 136
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 136
acauaguaca uagagaaugu u 21

<210> SEQ ID NO 137
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 137
acauacauag uacauagagu u 21

<210> SEQ ID NO 138
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 138
ucaugaaauc guuacguugu u 21

<210> SEQ ID NO 139
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 139
aauaacguuc augaaaucgu u 21

<210> SEQ ID NO 140
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 140
uaauaacguu caugaaaucu u 21

<210> SEQ ID NO 141
<211> LENGTH: 21

<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 141
auaauaacgu ucaugaaauu u 21

<210> SEQ ID NO 142
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 142
aaguuaagcu cccauacagu u 21

<210> SEQ ID NO 143
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 143
uaauaagaua ccagugucau u 21

<210> SEQ ID NO 144
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 144
uacuuuaaua agauaccagu u 21

<210> SEQ ID NO 145
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 145
auggcgacau gaucuuucuu u 21

<210> SEQ ID NO 146
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 146

-continued

```
aaauguaccc aaugauaagu u                                              21


<210> SEQ ID NO 147
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147

gaacugacca gauaugacuu u                                              21


<210> SEQ ID NO 148
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148

agaugcucac uuuauuaucu u                                              21


<210> SEQ ID NO 149
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149

ucacuuuauu aucccuauuu u                                              21


<210> SEQ ID NO 150
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150

guuuuaccug uucugaaauu u                                              21


<210> SEQ ID NO 151
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151

guucugaaau guucuuaaau u                                              21


<210> SEQ ID NO 152
<211> LENGTH: 21
<212> TYPE: RNA
<213> ORGANISM: Artificial Sequence
<220> FEATURE:
<221> NAME/KEY: source
```

<223> OTHER INFORMATION: /note="Description of Artificial Sequence:
      Synthetic oligonucleotide"

<400> SEQUENCE: 152
acuccaacgu augugguuau u                                              21

<210> SEQ ID NO 153
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
caacguaugu gguuaucugu u                                              21

<210> SEQ ID NO 154
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
uggguuaagu guuuaucauu u                                              21

<210> SEQ ID NO 155
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
cauucucuau guacuauguu u                                              21

<210> SEQ ID NO 156
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
cucuauguac uauguauguu u                                              21

<210> SEQ ID NO 157
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
caacguaacg auuucaugau u                                              21

<210> SEQ ID NO 158

<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 158
cgauuucaug aacguuauuu u 21

<210> SEQ ID NO 159
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 159
gauuucauga acguuauuau u 21

<210> SEQ ID NO 160
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 160
auuucaugaa cguuauuauu u 21

<210> SEQ ID NO 161
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 161
cuguauggga gcuuaacuuu u 21

<210> SEQ ID NO 162
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 162
ugacacuggu aucuuauuau u 21

<210> SEQ ID NO 163
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 163
cugguaucuu auuaaaguau u 21

<210> SEQ ID NO 164
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 164
auggcgacau gaucuuucuu u 21

<210> SEQ ID NO 165
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 165
aaauguaccc aaugauaagu u 21

<210> SEQ ID NO 166
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 166
gaacugacca gauaugacuu u 21

<210> SEQ ID NO 167
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 167
agaugcucac uuuauuaucu u 21

<210> SEQ ID NO 168
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 168
ucacuuuauu aucccuauuu u 21

<210> SEQ ID NO 169
<211> LENGTH: 21
<212> TYPE: RNA
<213> ORGANISM: Artificial Sequence
<220> FEATURE:

-continued

<221> NAME/KEY: source
<223> OTHER INFORMATION: /note="Description of Artificial Sequence: Synthetic oligonucleotide"

<400> SEQUENCE: 169
guuuuaccug uucugaaauu u 21

<210> SEQ ID NO 170
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 170
guucugaaau guucuuaaau u 21

<210> SEQ ID NO 171
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 171
acuccaacgu augugguuau u 21

<210> SEQ ID NO 172
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 172
caacguaugu gguuaucugu u 21

<210> SEQ ID NO 173
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 173
uggguuaagu guuuaucauu u 21

<210> SEQ ID NO 174
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 174
cucuauguac uauguauguu u 21

-continued

<210> SEQ ID NO 175
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 175
caacguaacg auuucaugau u 21

<210> SEQ ID NO 176
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 176
cgauuucaug aacguuauuu u 21

<210> SEQ ID NO 177
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 177
gauuucauga acguuauuau u 21

<210> SEQ ID NO 178
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 178
auuucaugaa cguuauuauu u 21

<210> SEQ ID NO 179
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 179
cuguauggga gcuuaacuuu u 21

<210> SEQ ID NO 180
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 180
ugacacuggu aucuuauuau u 21

<210> SEQ ID NO 181
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 181
cugguaucuu auuaaaguau u 21

<210> SEQ ID NO 182
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 182
agaaagauca ugucgccauu u 21

<210> SEQ ID NO 183
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 183
cuuaucauug gguacauuuu u 21

<210> SEQ ID NO 184
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 184
agucauaucu ggucaguucu u 21

<210> SEQ ID NO 185
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 185
gauaauaaag ugagcaucuu u 21

<210> SEQ ID NO 186
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 186
aauagggaua auaaagugau u 21

<210> SEQ ID NO 187
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 187
auuucagaac agguaaaacu u 21

<210> SEQ ID NO 188
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 188
uuuaagaaca uuucagaacu u 21

<210> SEQ ID NO 189
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 189
uaaccacaua cguuggaguu u 21

<210> SEQ ID NO 190
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 190
cagauaacca cauacguugu u 21

<210> SEQ ID NO 191
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 191
augauaaaca cuuaacccau u 21

<210> SEQ ID NO 192
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 192
acauacauag uacauagagu u 21

<210> SEQ ID NO 193
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 193
ucaugaaauc guuacguugu u 21

<210> SEQ ID NO 194
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 194
aauaacguuc augaaaucgu u 21

<210> SEQ ID NO 195
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 195
uaauaacguu caugaaaucu u 21

<210> SEQ ID NO 196
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 196
auaauaacgu ucaugaaauu u 21

<210> SEQ ID NO 197
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 197
aaguuaagcu cccauacagu u 21

<210> SEQ ID NO 198
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 198
uaauaagaua ccagugucau u 21

<210> SEQ ID NO 199
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 199
uacuuuaaua agauaccagu u 21

<210> SEQ ID NO 200
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 200
agaaagatca tgtcgccat 19

<210> SEQ ID NO 201
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 201
cttatcattg ggtacattt 19

<210> SEQ ID NO 202
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:

```
<221> NAME/KEY: source
<223> OTHER INFORMATION: /note="Description of Combined DNA/RNA
      Molecule: Synthetic oligonucleotide"

<400> SEQUENCE: 202

agtcatatct ggtcagttc                                                19


<210> SEQ ID NO 203
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 203

gataataaag tgagcatct                                                19


<210> SEQ ID NO 204
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 204

aatagggata ataaagtga                                                19


<210> SEQ ID NO 205
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 205

atttcagaac aggtaaaac                                                19


<210> SEQ ID NO 206
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 206

tttaagaaca tttcagaac                                                19
```

<210> SEQ ID NO 207
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 207
taaccacata cgttggagt 19

<210> SEQ ID NO 208
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 208
cagataacca catacgttg 19

<210> SEQ ID NO 209
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 209
tcacagataa ccacatacg 19

<210> SEQ ID NO 210
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 210
ttcacagata accacatac 19

<210> SEQ ID NO 211
<211> LENGTH: 19
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 211

aactttcaca gataaccac                                              19


<210> SEQ ID NO 212
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 212

aaacaccagt ttaggaaaa                                              19


<210> SEQ ID NO 213
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 213

aaacacttaa cccagatat                                              19


<210> SEQ ID NO 214
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 214

taaacactta acccagata                                              19


<210> SEQ ID NO 215
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

<400> SEQUENCE: 215
atgataaaca cttaaccca 19

<210> SEQ ID NO 216
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 216
acatagtaca tagagaatg 19

<210> SEQ ID NO 217
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 217
acatacatag tacatagag 19

<210> SEQ ID NO 218
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 218
tcatgaaatc gttacgttg 19

<210> SEQ ID NO 219
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 219
aataacgttc atgaaatcg 19

<210> SEQ ID NO 220

<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 220
taataacgtt catgaaatc 19

<210> SEQ ID NO 221
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 221
ataataacgt tcatgaaat 19

<210> SEQ ID NO 222
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 222
aagttaagct cccatacag 19

<210> SEQ ID NO 223
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 223
taataagata ccagtgtca 19

<210> SEQ ID NO 224
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<220> FEATURE:
<221> NAME/KEY: source
<223> OTHER INFORMATION: /note="Description of Combined DNA/RNA
      Molecule: Synthetic oligonucleotide"

<400> SEQUENCE: 224
tactttaata agataccag 19

<210> SEQ ID NO 225
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 225
atggcgacat gatctttct 19

<210> SEQ ID NO 226
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 226
aaatgtaccc aatgataag 19

<210> SEQ ID NO 227
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 227
gaactgacca gatatgact 19

<210> SEQ ID NO 228
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 228
agatgctcac tttattatc 19

<210> SEQ ID NO 229
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 229
tcactttatt atccctatt 19

<210> SEQ ID NO 230
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 230
gttttacctg ttctgaaat 19

<210> SEQ ID NO 231
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 231
gttctgaaat gttcttaaa 19

<210> SEQ ID NO 232
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 232
actccaacgt atgtggtta 19

<210> SEQ ID NO 233
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 233
caacgtatgt ggttatctg 19

<210> SEQ ID NO 234
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 234
cgtatgtggt tatctgtga 19

<210> SEQ ID NO 235
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 235
gtatgtggtt atctgtgaa 19

<210> SEQ ID NO 236
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 236
gtggttatct gtgaaagtt 19

<210> SEQ ID NO 237
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 237
ttttcctaaa ctggtgttt 19

<210> SEQ ID NO 238
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 238
atatctgggt taagtgttt 19

<210> SEQ ID NO 239
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 239
tatctgggtt aagtgttta 19

<210> SEQ ID NO 240
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 240
tgggttaagt gtttatcat 19

<210> SEQ ID NO 241
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 241
cattctctat gtactatgt 19

-continued

<210> SEQ ID NO 242
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 242
ctctatgtac tatgtatgt 19

<210> SEQ ID NO 243
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 243
caacgtaacg atttcatga 19

<210> SEQ ID NO 244
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 244
cgatttcatg aacgttatt 19

<210> SEQ ID NO 245
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 245
gatttcatga acgttatta 19

<210> SEQ ID NO 246
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 246
atttcatgaa cgttattat 19

<210> SEQ ID NO 247
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 247
ctgtatggga gcttaactt 19

<210> SEQ ID NO 248
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 248
tgacactggt atcttatta 19

<210> SEQ ID NO 249
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 249
ctggtatctt attaaagta 19

<210> SEQ ID NO 250
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 250
agaaagatca tgtcgccatu u 21

<210> SEQ ID NO 251
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 251
cttatcattg ggtacatttu u 21

<210> SEQ ID NO 252
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 252
agtcatatct ggtcagttcu u 21

<210> SEQ ID NO 253
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 253
gataataaag tgagcatctu u 21

<210> SEQ ID NO 254
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 254
aatagggata ataaagtgau u 21

<210> SEQ ID NO 255
<211> LENGTH: 21
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 255
atttcagaac aggtaaaacu u 21

<210> SEQ ID NO 256
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 256
tttaagaaca tttcagaacu u 21

<210> SEQ ID NO 257
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 257
taaccacata cgttggagtu u 21

<210> SEQ ID NO 258
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 258
cagataacca catacgttgu u 21

<210> SEQ ID NO 259
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 259
tcacagataa ccacatacgu u 21

<210> SEQ ID NO 260
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 260
ttcacagata accacatacu u 21

<210> SEQ ID NO 261
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 261
aactttcaca gataaccacu u 21

<210> SEQ ID NO 262
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 262
aaacaccagt ttaggaaaau u 21

<210> SEQ ID NO 263
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 263
aaacacttaa cccagatatu u 21

<210> SEQ ID NO 264
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 264
taaacactta acccagatau u 21

<210> SEQ ID NO 265
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 265
atgataaaca cttaacccau u 21

<210> SEQ ID NO 266
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 266
acatagtaca tagagaatgu u 21

<210> SEQ ID NO 267
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 267
acatacatag tacatagagu u 21

<210> SEQ ID NO 268
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 268
tcatgaaatc gttacgttgu u 21

<210> SEQ ID NO 269
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 269
aataacgttc atgaaatcgu u 21

<210> SEQ ID NO 270
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 270
taataacgtt catgaaatcu u 21

<210> SEQ ID NO 271
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 271
ataataacgt tcatgaaatu u 21

<210> SEQ ID NO 272
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 272
aagttaagct cccatacagu u 21

<210> SEQ ID NO 273
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 273
taataagata ccagtgtcau u 21

<210> SEQ ID NO 274
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 274
tactttaata agataccagu u 21

<210> SEQ ID NO 275
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 275
atggcgacat gatctttctu u 21

<210> SEQ ID NO 276
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 276
aaatgtaccc aatgataagu u 21

<210> SEQ ID NO 277
<211> LENGTH: 21

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 277

gaactgacca gatatgactu u                                              21


<210> SEQ ID NO 278
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 278

agatgctcac tttattatcu u                                              21


<210> SEQ ID NO 279
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 279

tcactttatt atccctattu u                                              21


<210> SEQ ID NO 280
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 280

gttttacctg ttctgaaatu u                                              21


<210> SEQ ID NO 281
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 281

gttctgaaat gttcttaaau u                                          21


<210> SEQ ID NO 282
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 282

actccaacgt atgtggttau u                                          21


<210> SEQ ID NO 283
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 283

caacgtatgt ggttatctgu u                                          21


<210> SEQ ID NO 284
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 284

cgtatgtggt tatctgtgau u                                          21


<210> SEQ ID NO 285
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 285

gtatgtggtt atctgtgaau u                                          21
```

<210> SEQ ID NO 286
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 286
gtggttatct gtgaaagttu u 21

<210> SEQ ID NO 287
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 287
ttttcctaaa ctggtgtttu u 21

<210> SEQ ID NO 288
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 288
atatctgggt taagtgtttu u 21

<210> SEQ ID NO 289
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 289
tatctgggtt aagtgtttau u 21

<210> SEQ ID NO 290
<211> LENGTH: 21
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 290

tgggttaagt gtttatcatu u                                           21


<210> SEQ ID NO 291
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 291

cattctctat gtactatgtu u                                           21


<210> SEQ ID NO 292
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 292

ctctatgtac tatgtatgtu u                                           21


<210> SEQ ID NO 293
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 293

caacgtaacg atttcatgau u                                           21


<210> SEQ ID NO 294
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

<400> SEQUENCE: 294
cgatttcatg aacgttattu u 21

<210> SEQ ID NO 295
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 295
gatttcatga acgttattau u 21

<210> SEQ ID NO 296
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 296
atttcatgaa cgttattatu u 21

<210> SEQ ID NO 297
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 297
ctgtatggga gcttaacttu u 21

<210> SEQ ID NO 298
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 298
tgacactggt atcttattau u 21

<210> SEQ ID NO 299

<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 299
ctggtatctt attaaagtau u 21

<210> SEQ ID NO 300
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 300
ucaugaaauc guuacguugu u 21

<210> SEQ ID NO 301
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 301
caacguaacg auuucaugau u 21

<210> SEQ ID NO 302
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 302
augauaaaca cuuaacccau u 21

<210> SEQ ID NO 303
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 303
ucaugaaauc guuacguuga c 21

<210> SEQ ID NO 304
<211> LENGTH: 21
<212> TYPE: RNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"

<400> SEQUENCE: 304

caacguaacg auuucaugaa c                                            21


<210> SEQ ID NO 305
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305

uggguuaagu guuuaucauu u                                            21
```

UNITED STATES PATENT AND TRADEMARK OFFICE
CERTIFICATE OF CORRECTION

PATENT NO.        : 9,868,949 B2  
APPLICATION NO.   : 14/770765  
DATED             : January 16, 2018  
INVENTOR(S)       : Brian Bettencourt et al.

Page 1 of 1

It is certified that error appears in the above-identified patent and that said Letters Patent is hereby corrected as shown below:

On the Title Page

Item (72) (Inventors), Column 1, Line 5, delete "Heusken" and insert -- Huesken --.

Signed and Sealed this  
Twelfth Day of June, 2018

Andrei Iancu  
*Director of the United States Patent and Trademark Office*